(12) United States Patent
Moodie et al.

(10) Patent No.: US 10,669,333 B2
(45) Date of Patent: *Jun. 2, 2020

(54) METHOD OF TREATING A TUMOR NECROSIS FACTOR α (TNFα)-RELATED DISORDER BY USING AN INDUCTION DOSING REGIMEN OF ADALIMUMAB

(71) Applicant: Fresenius Kabi Deutschland GmbH, Bad Homburg (DE)

(72) Inventors: Rachel Moodie, Hofstetten (CH); Elizabeth Hyland, Neuchatel (CH)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/014,446

(22) Filed: Jun. 21, 2018

(65) Prior Publication Data

US 2018/0291091 A1    Oct. 11, 2018

Related U.S. Application Data

(63) Continuation of application No. 15/564,677, filed as application No. PCT/EP2016/057847 on Apr. 8, 2016, now Pat. No. 10,179,811.

(30) Foreign Application Priority Data

Apr. 10, 2015  (EP) .................................... 15163277
Apr. 15, 2015  (EP) .................................... 15163775

(51) Int. Cl.
*A61K 39/00*    (2006.01)
*C07K 16/24*    (2006.01)

(52) U.S. Cl.
CPC ...... *C07K 16/241* (2013.01); *A61K 2039/505* (2013.01); *A61K 2039/54* (2013.01); *A61K 2039/545* (2013.01); *C07K 2317/21* (2013.01); *C07K 2317/76* (2013.01)

(58) Field of Classification Search
CPC .............. C07K 16/241; C07K 2317/21; C07K 2317/76; A61K 2039/505; A61K 2039/54; A61K 2039/545

See application file for complete search history.

(56) References Cited

U.S. PATENT DOCUMENTS

| | | | |
|---|---|---|---|
| 7,612,181 B2 | 11/2009 | Wu et al. |
| 7,919,264 B2 | 4/2011 | Maksymowych et al. |
| 8,092,998 B2 | 1/2012 | Stuhlmuller et al. |
| 8,216,583 B2 | 7/2012 | Kruase et al. |
| 8,258,268 B2 | 9/2012 | Wu et al. |
| 8,420,081 B2 | 4/2013 | Fraunhofer et al. |
| 8,679,061 B2 | 3/2014 | Julian et al. |
| 8,715,664 B2 | 5/2014 | Hoffman et al. |
| 8,747,854 B2 | 6/2014 | Okun et al. |
| 8,795,670 B2 | 8/2014 | Krause et al. |
| 8,802,100 B2 | 8/2014 | Krause et al. |
| 8,802,101 B2 | 8/2014 | Krause et al. |
| 8,802,102 B2 | 8/2014 | Krause et al. |
| 8,808,700 B1 | 8/2014 | Hoffman et al. |
| 8,821,865 B2 | 9/2014 | Neu et al. |
| 8,846,046 B2 | 9/2014 | Kaymakcalan et al. |
| 8,883,146 B2 | 11/2014 | Fraunhofer et al. |
| 8,889,135 B2 | 11/2014 | Fischkoff et al. |
| 8,889,136 B2 | 11/2014 | Hoffman et al. |
| 8,906,373 B2 | 12/2014 | Banerjee et al. |
| 8,911,737 B2 | 12/2014 | Fischkoff et al. |
| 8,911,741 B2 | 12/2014 | Krause et al. |
| 8,916,157 B2 | 12/2014 | Krause et al. |
| 8,916,158 B2 | 12/2014 | Krause et al. |
| 8,926,975 B2 | 1/2015 | Wong et al. |
| 8,932,591 B2 | 1/2015 | Krause et al. |
| 8,940,305 B2 | 1/2015 | Krause et al. |
| 8,961,973 B2 | 2/2015 | Hoffman et al. |
| 8,961,974 B2 | 2/2015 | Hoffman et al. |
| 8,974,790 B2 | 3/2015 | Fischkoff et al. |
| 8,986,693 B1 | 3/2015 | Hoffman et al. |
| 8,992,926 B2 | 3/2015 | Fischkoff et al. |
| 8,999,337 B2 | 4/2015 | Medich et al. |
| 9,017,680 B2 | 4/2015 | Fischkoff et al. |
| 9,061,005 B2 | 6/2015 | Hoffman et al. |
| 9,067,992 B2 | 6/2015 | Hoffman et al. |
| 9,073,987 B2 | 7/2015 | Fischkoff et al. |
| 9,085,619 B2 | 7/2015 | Fraunhofer et al. |
| 9,085,620 B1 | 7/2015 | Hoffman et al. |

(Continued)

FOREIGN PATENT DOCUMENTS

| WO | WO-2005110452 A2 | 11/2005 |
|---|---|---|
| WO | WO-2007120720 A2 | 10/2007 |

OTHER PUBLICATIONS

Burness CB and Keating GM (Jun. 2013) BioDrugs. 27(3):247-62 (doi: 10.1007/s40259-013-0033-6).*
Aquas M, et al. (Aug. 2012) World J Gastroenterol. 18(32):4391-8 (doi: 10.3748/wjg.v18.i32.4391).*
Bolduc C and Bissonnette R (Jul.-Aug. 2012) J Cutan Med Surg. 16(4):257-60 (doi: 10.1177/120347541201600407).*
Reinisch W, et al. (Jun. 2011) Gut. 60(6):780-7 (doi: 10.1136/gut.2010.221127).*
Peyrin-Biroulet L, et al. (Apr. 28, 2007) World J Gastroenterol. 13(16):2328-32. (doi: 10.3748/wjg.v13.i16.2328).*
Herfarth HH, et al. (Aug. 2010) Inflamm Bowel Dis. 16(8):1421-1430. (doi: 10.1002/ibd.21246).*

(Continued)

*Primary Examiner* — Robert S Landsman
(74) *Attorney, Agent, or Firm* — Goodwin Procter LLP

(57) ABSTRACT

The invention relates to a multiple-variable dose method for treating a disorder in which TNFα activity is detrimental, comprising administering to a subject in need thereof a first induction dose of an anti-TNFα antibody which ranges from 161 to 320 mg such that a threshold level of TNFα inhibitor is achieved within an induction phase; and subsequently administering to the subject at least one treatment dose of the TNFα inhibitor within a treatment phase, such that treatment occurs.

13 Claims, No Drawings
Specification includes a Sequence Listing.

(56) References Cited

U.S. PATENT DOCUMENTS

| | | |
|---|---|---|
| 9,086,418 B2 | 7/2015 | Maksymowych et al. |
| 9,090,689 B1 | 7/2015 | Hoffman et al. |
| 9,114,166 B2 | 8/2015 | Krause et al. |
| 9,187,559 B2 | 11/2015 | Hoffman et al. |
| 9,220,781 B2 | 12/2015 | Krause et al. |
| 9,272,041 B2 | 3/2016 | Krause et al. |
| 9,272,042 B2 | 3/2016 | Krause et al. |
| 9,279,015 B2 | 3/2016 | Wong et al. |
| 9,284,370 B1 | 3/2016 | Medich et al. |
| 9,289,497 B2 | 3/2016 | Krause et al. |
| 9,295,725 B2 | 3/2016 | Krause et al. |
| 9,302,011 B2 | 4/2016 | Krause et al. |
| 9,327,032 B2 | 5/2016 | Krause et al. |
| 9,334,320 B2 | 5/2016 | Okun et al. |
| 9,399,061 B2 | 7/2016 | Kupper et al. |
| 9,452,138 B2 | 9/2016 | Trollsas et al. |
| 9,486,584 B2 | 11/2016 | Julian et al. |
| 9,499,615 B2 | 11/2016 | Hoffman et al. |
| 9,512,216 B2 | 12/2016 | Hoffman et al. |
| 9,546,212 B2 | 1/2017 | Fischkoff et al. |
| 9,572,938 B2 | 2/2017 | Julian et al. |
| 9,605,064 B2 | 3/2017 | Okun et al. |
| 9,624,295 B2 | 4/2017 | Medich et al. |
| 9,669,093 B2 | 6/2017 | Medich et al. |
| 9,732,152 B2 | 8/2017 | Krause et al. |
| 9,738,714 B2 | 8/2017 | Krause et al. |
| 9,750,808 B2 | 9/2017 | Krause et al. |
| 9,950,066 B2 | 4/2018 | Krause et al. |
| 2003/0235585 A1 | 12/2003 | Fischkoff et al. |
| 2004/0033228 A1 | 2/2004 | Krause et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0166111 A1 | 8/2004 | Kaymakcalan et al. |
| 2004/0219142 A1 | 11/2004 | Banerjee et al. |
| 2006/0009385 A1 | 1/2006 | Hoffman et al. |
| 2006/0153846 A1 | 7/2006 | Krause et al. |
| 2007/0041905 A1 | 2/2007 | Hoffman et al. |
| 2007/0071675 A1 | 3/2007 | Wu et al. |
| 2007/0071747 A1 | 3/2007 | Hoffman et al. |
| 2007/0081996 A1 | 4/2007 | Hoffman et al. |
| 2007/0172897 A1 | 7/2007 | Maksymowych et al. |
| 2007/0202104 A1 | 8/2007 | Banerjee et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0123378 A1 | 5/2009 | Wong et al. |
| 2009/0215992 A1 | 8/2009 | Wu et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0021451 A1 | 1/2010 | Wong |
| 2010/0047239 A1 | 2/2010 | Wu et al. |
| 2010/0160894 A1 | 6/2010 | Julian et al. |
| 2010/0278822 A1 | 11/2010 | Fraunhofer et al. |
| 2011/0171227 A1 | 7/2011 | Okun et al. |
| 2011/0300151 A1 | 12/2011 | Okun et al. |
| 2012/0014956 A1 | 1/2012 | Kupper et al. |
| 2012/0039900 A1 | 2/2012 | Stuhlmuller et al. |
| 2012/0107783 A1 | 5/2012 | Julian et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0263731 A1 | 10/2012 | Fraunhofer et al. |
| 2012/0282262 A1 | 11/2012 | Okun et al. |
| 2012/0282270 A1 | 11/2012 | Krause et al. |
| 2013/0004416 A1 | 1/2013 | Wu et al. |
| 2013/0004507 A1 | 1/2013 | Fischkoff et al. |
| 2013/0122011 A1 | 5/2013 | Hoffman et al. |
| 2013/0156760 A1 | 6/2013 | Fraunhofer et al. |
| 2013/0195888 A1 | 8/2013 | Wang et al. |
| 2013/0243763 A1 | 9/2013 | Banerjee et al. |
| 2013/0243786 A1 | 9/2013 | Banerjee et al. |
| 2014/0017174 A1 | 1/2014 | Atreya et al. |
| 2014/0086929 A1 | 3/2014 | Krause et al. |
| 2014/0086930 A1 | 3/2014 | Krause et al. |
| 2014/0086931 A1 | 3/2014 | Krause et al. |
| 2014/0100359 A1 | 4/2014 | Wu et al. |
| 2014/0127222 A1 | 5/2014 | Krause et al. |
| 2014/0141007 A1 | 5/2014 | Fraunhofer et al. |
| 2014/0141008 A1 | 5/2014 | Fraunhofer et al. |
| 2014/0154256 A1 | 6/2014 | Wu et al. |
| 2014/0186368 A1 | 7/2014 | Fischkoff et al. |
| 2014/0186446 A1 | 7/2014 | Trollsas et al. |
| 2014/0200332 A1 | 7/2014 | Kaymakcalan et al. |
| 2014/0212430 A1 | 7/2014 | Hoffman et al. |
| 2014/0213768 A1 | 7/2014 | Wu et al. |
| 2014/0234222 A1 | 8/2014 | Hoffman et al. |
| 2014/0248215 A1 | 9/2014 | Hoffman et al. |
| 2014/0248275 A1 | 9/2014 | Hoffman et al. |
| 2014/0248276 A1 | 9/2014 | Hoffman et al. |
| 2014/0248277 A1 | 9/2014 | Hoffman et al. |
| 2014/0255396 A1 | 9/2014 | Hoffman et al. |
| 2014/0271637 A1 | 9/2014 | Fischkoff et al. |
| 2014/0286867 A1 | 9/2014 | Hoffman et al. |
| 2014/0286939 A1 | 9/2014 | Banerjee et al. |
| 2014/0286940 A1 | 9/2014 | Banerjee et al. |
| 2014/0286941 A1 | 9/2014 | Banerjee et al. |
| 2014/0296493 A1 | 10/2014 | Hoffman et al. |
| 2014/0314781 A1 | 10/2014 | Krause et al. |
| 2014/0322228 A1 | 10/2014 | Krause et al. |
| 2014/0322232 A1 | 10/2014 | Fischkoff et al. |
| 2014/0328855 A1 | 11/2014 | Wong |
| 2014/0341924 A1 | 11/2014 | Krause et al. |
| 2014/0341925 A1 | 11/2014 | Krause et al. |
| 2014/0377275 A1 | 12/2014 | Neu et al. |
| 2014/0377805 A1 | 12/2014 | Wu et al. |
| 2014/0377858 A1 | 12/2014 | Wu et al. |
| 2015/0004167 A1 | 1/2015 | Wu et al. |
| 2015/0017175 A1 | 1/2015 | Fischkoff et al. |
| 2015/0023977 A1 | 1/2015 | Fraunhofer et al. |
| 2015/0023982 A1 | 1/2015 | Fischkoff et al. |
| 2015/0037772 A1 | 2/2015 | Julian et al. |
| 2015/0050216 A1 | 2/2015 | Willian et al. |
| 2015/0056202 A1 | 2/2015 | Wu et al. |
| 2015/0056212 A1 | 2/2015 | Kupper et al. |
| 2015/0064194 A1 | 3/2015 | Kupper et al. |
| 2015/0064195 A1 | 3/2015 | Kupper et al. |
| 2015/0071938 A1 | 3/2015 | Hoffman et al. |
| 2015/0071939 A1 | 3/2015 | Fischkoff et al. |
| 2015/0071945 A1 | 3/2015 | Fischkoff et al. |
| 2015/0079101 A1 | 3/2015 | Fischkoff et al. |
| 2015/0086554 A1 | 3/2015 | Wu et al. |
| 2015/0086569 A1 | 3/2015 | Hoffman et al. |
| 2015/0093394 A1 | 4/2015 | Krause et al. |
| 2015/0147327 A1 | 5/2015 | Wu et al. |
| 2015/0147335 A1 | 5/2015 | Okun et al. |
| 2015/0165023 A1 | 6/2015 | Fischkoff et al. |
| 2015/0175690 A1 | 6/2015 | Hoffman et al. |
| 2015/0175691 A1 | 6/2015 | Fischkoff et al. |
| 2015/0218268 A1 | 8/2015 | Hoffman et al. |
| 2015/0218269 A1 | 8/2015 | Hoffman et al. |
| 2015/0246968 A1 | 9/2015 | Fischkoff et al. |
| 2015/0306224 A1 | 10/2015 | Krause et al. |
| 2015/0343065 A1 | 12/2015 | Krause et al. |
| 2015/0344560 A1 | 12/2015 | Krause et al. |
| 2015/0344561 A1 | 12/2015 | Krause et al. |
| 2015/0344562 A1 | 12/2015 | Krause et al. |
| 2015/0344563 A1 | 12/2015 | Krause et al. |
| 2015/0361170 A1 | 12/2015 | Fraunhofer et al. |
| 2015/0368335 A1 | 12/2015 | Banerjee et al. |
| 2016/0017030 A1 | 1/2016 | Neu et al. |

(56) References Cited

U.S. PATENT DOCUMENTS

| | | |
|---|---|---|
| 2016/0030578 A1 | 2/2016 | Krause et al. |
| 2016/0060336 A1 | 3/2016 | Medich et al. |
| 2016/0089495 A1 | 3/2016 | Julian et al. |
| 2016/0151488 A1 | 6/2016 | Medich et al. |
| 2016/0176957 A1 | 6/2016 | Hoffman et al. |
| 2016/0185849 A1 | 6/2016 | Hoffman et al. |
| 2016/0200809 A1 | 7/2016 | Willian et al. |
| 2016/0222101 A1 | 8/2016 | Fraunhofer et al. |
| 2016/0251424 A1 | 9/2016 | Wong et al. |
| 2016/0272704 A1 | 9/2016 | Hoffman et al. |
| 2016/0280776 A1 | 9/2016 | Medich et al. |
| 2016/0280777 A1 | 9/2016 | Fischkoff et al. |
| 2016/0297879 A1 | 10/2016 | Hoffman et al. |
| 2016/0376360 A9 | 12/2016 | Hoffman et al. |
| 2017/0022271 A1 | 1/2017 | Hoffman et al. |
| 2017/0042816 A1 | 2/2017 | Trollsas et al. |
| 2017/0044249 A1 | 2/2017 | Hoffman et al. |
| 2017/0056498 A1 | 3/2017 | Krause et al. |
| 2017/0101465 A1 | 4/2017 | Okun et al. |
| 2017/0143828 A1 | 5/2017 | Fraunhofer et al. |
| 2017/0145087 A1 | 5/2017 | Krause et al. |
| 2017/0151329 A1 | 6/2017 | Krause et al. |
| 2017/0157249 A1 | 6/2017 | Kupper et al. |
| 2017/0158759 A1 | 6/2017 | Krause et al. |
| 2017/0203041 A1 | 7/2017 | Julian et al. |
| 2017/0210795 A1 | 7/2017 | Medich et al. |
| 2017/0313786 A1 | 11/2017 | Wu et al. |
| 2018/0036407 A1 | 2/2018 | Wan et al. |
| 2018/0044414 A1 | 2/2018 | Okun et al. |
| 2018/0110854 A1 | 4/2018 | Medich et al. |

OTHER PUBLICATIONS

Colombel et al. "Adalimumab Induces and Maintains Clinical Response and Remission in Patients With Active Crohn's Disease: Results of the CHARM Trial", Gastroenterology, Elsevier, Philadelphia, PA, vol. 131, No. 3, Sep. 1, 2006 (1 page).

Hanauer et al. "Human Anti-Tumor Necrosis Factor Monoclonal Antibody (Adalimumab) in Crohn's Disease: the CLASSIC-I Trial", Gastroenterology, Elsevier, Philadelphia, PA., vol. 130, No. 2, Feb. 1, 2006 (11 pages).

Panaccione et al. "Adalimumab sustains clinical remission and overall clinical benefit after 2 years of therapy for Crohn's disease", Alimentary Pharmacology & Therapeutics, vol. 31, No. 12, Mar. 18, 2010 (14 pages).

Rutgeerts et al. "Infliximab for Induction and Maintenance Therapy for Ulcerative Colitis background", Boston (B.E.S.) N Engl. J MED, vol. 353, No. 23, Dec. 8, 2005 (15 pages).

Sandborn et al. "Adalimumab for maintenance treatment of Crohn's disease: results of the CLASSIC II Trial", GUT, vol. 56, No. 9, Apr. 5, 2007 (8 pages).

International Search Report for International Patent Application No. PCT/EP2016/057847 dated Jun. 15, 2016 (5 pages).

Written Opinion for International Patent Application No. PCT/EP2016/057847 dated Jun. 15, 2016 (7 pages).

Mellstedt, Clinical considerations for biosimilar antibodies, EJC Supplements II, No. 3, 2013, (11 pages).

European Search Report and Search Opinion for European Patent Application No. 15163755.8 dated Oct. 14, 2015 (10 pages).

The IBD Center of the Academic Medical Center in Amsterdam, Listing of Sponsor Initiated Studies "Recruiting Studies for Ulcerative Colitis" accessed Jun. 15, 2018, at <http://www.ibd-amc.com/sponsor-initiated-studies/active-ulcerative-colitis/>(4 pages).

The European Medicines Agency Committee for Medicinal Products for Human Use (CHMP) Minutes of Meeting on Jan. 22-25, 2018 (131 pages).

"Study to Evaluate Efficacy and Safety of Two Drug Regimens in Subjects with Moderate to Severe Crohn's Disease" Study No. NCT02065570 dated Feb. 17, 2014 published by <http://www.clinicaltrials.gov>.

"Study to Evaluate efficacy and Safety of Two Drug Regimens in Subjects with Moderate to Severe Crohn's Disease" Study No. NCT02065570 dated Apr. 10, 2014 published by <http://www.clinicaltrials.gov>.

"Study to Evaluate efficacy and Safety of Two Drug Regimens in Subjects with Moderate to Severe Crohn's Disease" Study No. NCT02065570 dated Jan. 27, 2016 published by <http://www.clinicaltrials.gov>.

"Study to Evaluate efficacy and Safety of Two Drug Regimens in Subjects with Moderate to Severe Crohn's Disease" Study No. NCT02065570 dated Jun. 1, 2018 published by <http://www.clinicaltrials.gov>.

"Study to Evaluate efficacy and Safety of Two Drug Regimens in Subjects with Moderate to Severe Ulcerative Colitis" Study No. NCT02065622 dated Feb. 17, 2014 published by http://www.clinicaltrials.gov.

"Study to Evaluate efficacy and Safety of Two Drug Regimens in Subjects with Moderate to Severe Ulcerative Colitis" Study No. NCT02065622 dated Apr. 11, 2014 published by http://www.clinicaltrials.gov.

"Study to Evaluate efficacy and Safety of Two Drug Regimens in Subjects with Moderate to Severe Ulcerative Colitis" Study No. NCT02065622 dated Jan. 26, 2015 published by http://www.clinicaltrials.gov.

"Study to Evaluate efficacy and Safety of Two Drug Regimens in Subjects with Moderate to Severe Ulcerative Colitis" Study No. NCT02065622 dated May 8, 2018 published by http://www.clinicaltrials.gov.

HUMIRA® treatment protocol (Sep. 2012). Abbott. <https://www.accessdata.fda>gov/drugsatfda_docs/label/2012/125057s2321bl.pdf.

Westhovens et al., (2006), "A phase I study assessing the safety, clinical response, and pharmacokinetics of an experimental infliximab formulation for subcutaneous or intramuscular administration in patients with rheumatoid arthritis," *J. Rheumatology*, 33(5):847-853.

HUMIRA® "Highlights of Prescribing Information," Nov. 23, 2015, Abbvie Inc., North Chicago, IL. (Accessed from <https://www.accessdata.fda.gov/drugsatfda_docs/label/2015/125057s394lbl.pdf> on Sep. 11, 2019).

* cited by examiner

SEQUENCE LISTING

<160> NUMBER OF SEQ ID NOS: 10

<210> SEQ ID NO 1
<211> LENGTH: 107
<212> TYPE: PRT
<213> ORGANISM: Artificial Sequence
<220> FEATURE:
<223> OTHER INFORMATION: D2E7 light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: D2E7 heavy chain variabe region

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser

```
                 115                 120

<210> SEQ ID NO 3
<211> LENGTH: 9
<212> TYPE: PRT
<213> ORGANISM: Artificial Sequence
<220> FEATURE:
<223> OTHER INFORMATION: D2E7 light chain variable region CDR3
<220> FEATURE:
<221> NAME/KEY: misc_feature
<222> LOCATION: (9)..(9)
<223> OTHER INFORMATION: Xaa can be any naturally occurring amino acid

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: D2E7 heavy chain variable region CDR3
<220> FEATURE:
<221> NAME/KEY: misc_feature
<222> LOCATION: (12)..(12)
<223> OTHER INFORMATION: Xaa can be any naturally occurring amino acid

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: D2E7 light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: D2E7 heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: D2E7 light chain variable region CDR1

<400> SEQUENCE: 7

Arg Ala Ser Gln Gly Ile Arg Asn Tyr Leu Ala
1               5                   10

<210> SEQ ID NO 8
```

```
-continued

<211> LENGTH: 5
<212> TYPE: PRT
<213> ORGANISM: Artificial Sequence
<220> FEATURE:
<223> OTHER INFORMATION: D2E7 heavy chain variable region CDR1

<400> SEQUENCE: 8

Asp Tyr Ala Met His
1               5

<210> SEQ ID NO 9
<211> LENGTH: 321
<212> TYPE: DNA
<213> ORGANISM: Artificial Sequence
<220> FEATURE:
<223> OTHER INFORMATION: D2E7 light chain variable region

<400> SEQUENCE: 9
gacatccaga tgacccagtc tccatcctcc ctgtctgcat ctgtagggga cagagtcacc        60
atcacttgtc gggcaagtca gggcatcaga aattacttag cctggtatca gcaaaaacca       120
gggaaagccc ctaagctcct gatctatgct gcatccactt tgcaatcagg ggtcccatct       180
cggttcagtg gcagtggatc tgggacagat ttcactctca ccatcagcag cctacagcct       240
gaagatgttg caacttatta ctgtcaaagg tataaccgtg caccgtatac ttttggccag       300
gggaccaagg tggaaatcaa a                                                 321

<210> SEQ ID NO 10
<211> LENGTH: 363
<212> TYPE: DNA
<213> ORGANISM: Artificial Sequence
<220> FEATURE:
<223> OTHER INFORMATION: D2E7 heavy chain variable region

<400> SEQUENCE: 10
gaggtgcagc tggtggagtc tgggggaggc ttggtacagc ccggcaggtc cctgagactc        60
tcctgtgcgg cctctggatt cacctttgat gattatgcca tgcactgggt ccggcaagct       120
ccagggaagg gcctggaatg ggtctcagct atcacttgga atagtggtca catagactat       180
gcggactctg tgagggccg attcaccatc tccagagaca cgccaagaa ctccctgtat        240 ctgcaaatga acagtctgag agctgaggat acggccgtat attactgtgc gaaagtctcg       300
taccttagca ccgcgtcctc ccttgactat tggggccaag taccctggt caccgtctcg       360 agt                                                                     363
```

US 10,669,333 B2

METHOD OF TREATING A TUMOR NECROSIS FACTOR α (TNFα)-RELATED DISORDER BY USING AN INDUCTION DOSING REGIMEN OF ADALIMUMAB

CROSS-REFERENCE TO RELATED APPLICATIONS

This application is a continuation of U.S. patent application Ser. No. 15/564,677, filed Oct. 5, 2017, now U.S. Pat. No. 10,179,811, which is a U.S. National Stage Application filed under 35 U.S.C. § 371 of International Patent Application No. PCT/EP2016/057847, filed Apr. 8, 2016, which claims priority to and the benefit of European Patent Application No. 15163277.5, filed Apr. 10, 2015, and European Patent Application No. 15163775.8, filed Apr. 15, 2015, the entire disclosures of each of which are incorporated by reference herein in their entireties.

BACKGROUND OF THE INVENTION

Cytokines, such as interleukin-1 (IL-1) and tumor necrosis factor α (TNFα) are molecules produced by a variety of cells, such as monocytes and macrophages, which have been identified as mediators of inflammatory processes. Cytokines, including TNF, regulate the intensity and duration of the inflammatory response which occurs as the result of an injury or infection. Elevated levels of TNF play an important role in pathologic inflammation. TNF also referred to as (TNFα) has been implicated in the pathophysiology of a variety of human diseases and disorders, including sepsis, infections, autoimmune diseases, transplant rejection and graft-versus-host disease (see e. g., Moeller et al. (1990) Cytokine 2: 162; U.S. Pat. No. 5,231,024 to Moeller et al.; European Patent Publication No. 260 610 BI by Moeller, A. et al.; Vasilli (1992) Annu. Rev. Immunol. 10: 411; Tracey and Cerami (1994) Annu. Rev. Med. 45:491).

TNF has been implicated in psoriasis. Expression of TNF-induced proteins and the presence of activated T lymphocytes in psoriatic plaques but not uninvolved skin, suggest their involvement in the pathogenesis of the disease. There are several types of psoriasis according to cutaneous manifestations: plaque psoriasis, guttate psoriasis, erythrodermic psoriasis, generalized pustular and localized pustular psoriasis. Plaque psoriasis is the most common type, however. Treatment of psoriasis depends on the extent of the disease. Topical corticosteroids are commonly used for mild to moderate localized cases. Keratolytic agents and coal tar are also used as topical medications, and phototherapy is commonly used for more widespread disease. Other systemic therapy, such as methotrexate cyclosporine and synthetic retinoids are effective, but are often administered in rotation due to their possible cumulative toxic effect.

TNF has also been implicated in Crohn's disease. Crohn's is diagnosed on the basis of clinical, endoscopic, radiographic, and histologic criteria. The treatment of Crohn's disease is challenging. Treatment is based on location, extent, and severity of disease. Current compounds and regimens do not completely abate the inflammatory process and have significant side effects.

The goal of medical treatment for Crohn's disease includes improving patients' quality of life while reducing the need for hospitalization and surgery. The current medical armamentarium includes 5-aminosalicylates, corticosteroids, immunomodulators, and biologic agents, such as anti-TNFα treatments including infliximab (disclsoed in EP0610201), etanercept (disclosed in U.S. Pat. No. 8,722, 631) and adalimumab (disclosed in WO2005110452). In the prior art, response to treatment has been measured by clinical improvement in symptoms; however, achieving mucosal healing is more challenging. Mucosal healing, or endoscopic remission, is associated with increased rates of clinical remission, fewer hospitalizations, and fewer abdominal surgeries.

It is known to treat TNFα-related disorders with a liquid formulation containing 50 mg/ml Humira® (adalimumab). Of this formulation, 0.8 ml is subcutaenously injected into a subject such that a dose of 40 mg adalimumab is delivered. In order to deliver a higher dose of adalimumab, the subject must recevie multiple subcutaneous injections. Thus, there is a need in the art for an improved adalimumab treatment regimen to treat TNFα-related disorders which includes a reduced number of subcutaenous injections to be delivered to a subject as compared to a prior art treatment with adalimumab.

SUMMARY OF THE INVENTION

There is a need for an improved treatment regimen to treat TNFα-related disorders which includes a reduced number of subcutaenous injections as compared to the prior art treatment regimens with adalimumab. Furthermore, there is a need for an improved treatment regimen that can achieve mucosal healing in patients with Crohn's disease and ulcerative colitis. The present invention includes multiple-variable dose methods for improved treatment of TNFα-related disorders where TNFα activity is detrimental. In particular, the invention includes improved dosing regimens that achieves mucosal healing in patients with Crohn's disease and ulcerative colitis, wherein a reduced number of subcutaneous injections are delivered to the patient.

The invention describes a multiple-variable dose method for treating a disorder in which TNFα activity is detrimental, comprising administering to a subject in need thereof a first induction dose of an anti-TNFα antibody, such as adalimumab or a biosimilar thereof which ranges from 161 to 320 mg such that a threshold level of TNFα inhibitor is achieved within an induction phase; and subsequently administering to the subject at least one treatment dose of the TNFα inhibitor within a treatment phase, such that treatment occurs.

The invention also describes a multiple-variable dose method for treating Crohn's disease, comprising administering to a subject in need thereof a first induction dose of an anti-TNFα antibody, such as adalimumab or a biosimilar thereof which ranges from 161 to 320 mg such that a threshold level of TNFα inhibitor is achieved within an induction phase; and subsequently administering to the subject at least one treatment dose of the TNFα inhibitor within a treatment phase, such that treatment occurs. The multiple-variable dose method of the invention can also be used to treat ulcerative colitis or psoriasis. In another embodiment, multiple-variable dose method of the invention is used to treat as psoriasis in combination with psoriatic arthritis.

The invention includes a multiple-variable dose method of inducing remission of Crohn's disease or ulcerative colitis, comprising administering to a subject in need thereof a first induction dose of an anti-TNFα antibody, such as adalimumab or a biosimilar thereof which ranges from 161 to 320 mg such that a threshold level of TNFα inhibitor is achieved within an induction phase; and subsequently administering to the subject at least one treatment dose of the TNFα inhibitor within a treatment phase, such that treatment occurs. Said treatment regimen causing mucosal healing in the subject.

Prefereably, the dose amounts are delivered as a single dose, or alternatively are delivered as multiple doses.

Preferably the dose of an anti-TNFα antibody is delivered in one or more subcutaneous injections of a formulation containing 50 mg/ml of the anti-TNFα antibody. Preferably the anti-TNFα antibody is delivered as a single dose (i.e., a single 20 mg dose of 20 mg in 0.4 mL; a single 40 mg dose of 40 mg in 0.8 mL; a single 50 mg dose of 50 mg in 1.0 mL a single 80 mg dose of 80 mg in 1.2 mL). Alternatively the anti-TNFα antibody is delivered as multiple doses (i.e., an 80 mg dose as two×40 mg doses of 40 mg in 0.8 mL; a 100 mg dose as 2×50 mg doses of 50 mg in 1.0 mL, a 150 mg dose as 3×50 mg doses of 50 mg in 1.0 mL, a 160 mg dose as four×40 mg doses of 40 mg in 0.8 mL; a 200 mg dose as five×40 mg doses of 40 mg in 0.8 mL; a 200 mg dose as 4×50 mg doses of 50 mg in 1.0 mL, a 240 mg dose as six×40 mg doses of 40 mg in 0.8 mL; a 250 mg dose as 5×50 mg doses of 50 mg in 1.0 mL, a 280 mg dose as 7×40 mg doses of 40 mg in 0.8 mL; a 300 mg dose as 6×50 mg doses of 50 mg in 1.0 mL, or a 360 mg dose as eight×40 mg doses of 40 mg in 0.8 mL).

Preferably the dose of an anti-TNFα antibody is delivered in one or more subcutaneous injections of 0.8 ml of a formulation containing 100 mg/ml of the anti-TNFα antibody (i.e. the subcutaneous injection contains 80 mg anti-TNFα antibody), wherein the dose is selected from the group consisting of: the first induction dose, the second induction dose and the treatment dose.

Alternatively the dose of an anti-TNFα antibody is delivered in one or more subcutaneous injections of a formulation containing 100 mg/ml of the anti-TNFα antibody. Preferably, the dose is delivered as a single dose (e.g., a single 20 mg dose of 20 mg in 0.2 mL; a single 40 mg dose of 40 mg in 0.4 mL; a 50 mg dose as 1×50 mg doses of 50 mg in 0.5 mL a single 80 mg dose of 80 mg in 0.8 mL, a 100 mg dose as 1×100 mg doses of 100 mg in 1.0 mL). Alternatively, the dose is delivered as multiple doses (e.g., a 160 mg dose as two×80 mg doses of 80 mg in 0.8 mL; a 180 mg dose as as 2×90 mg doses of 90 mg in 0.9 mL; a 200 mg dose as 2×100 mg doses of 100 mg in 1.0 mL, a 240 mg dose as three×80 mg doses of 80 mg in 0.8 mL; a 300 mg dose as 3×100 mg doses of 100 mg in 1.0 mL or a 360 mg dose as four×80 mg doses of 80 mg in 0.8 mL).

Alernatively, the dose of an anti-TNFα antibody is delivered in one or more subcutaneous injections of 1.0 ml of a formulation containing 100 mg/ml of the anti-TNFα antibody (i.e. the subcutaneous injection contains 100 mg anti-TNFα antibody), wherein the dose is selected from the group consisting of: the first induction dose, the second induction dose and the treatment dose.

The invention includes a multiple-variable dose method of inducing remission of TNFα-related disorders selected from rheumatoid arthritis, plaque psoriasis, Uvetis, Axial Spondyloarthritis, Behcet's disease, spondyloarthritis, hidradenitis suppurativa, and giant cell arteritis. The method comprising administering to a subject in need thereof a first induction dose of an anti-TNFα antibody, such as adalimumab or a biosimilar thereof which ranges from 161 to 320 mg such that a threshold level of TNFα inhibitor is achieved within an induction phase; and subsequently administering to the subject at least one treatment dose of the TNFα inhibitor within a treatment phase, such that treatment occurs.

The invention includes a multiple-variable dose method of reducing psoriatic plaques comprising administering to a subject in need thereof a first induction dose of an anti-TNFα antibody, such as adalimumab or a biosimilar thereof which ranges from 81 to 160 mg such that a threshold level of TNFα inhibitor is achieved within an induction phase; and subsequently administering to the subject at least one treatment dose of the TNFα inhibitor within a treatment phase, such that treatment occurs.

The invention includes a multiple-variable dose method of inducing remission of TNFα-related disorders selected from rheumatoid arthritis, Crohn's disease, ulcerative colitis, Uvetis, Axial Spondyloarthritis, Behcet's disease, spondyloarthritis, hidradenitis suppurativa, and giant cell arteritis. The method comprising administering to a subject in need thereof a first induction dose of an anti-TNFα antibody, such as adalimumab or a biosimilar thereof which ranges from 81 to 160 mg such that a threshold level of TNFα inhibitor is achieved within an induction phase; and subsequently administering to the subject at least one treatment dose of the TNFα inhibitor within a treatment phase, such that treatment occurs.

The methods of the invention can be used to treat a TNFα-related disorder selected from the group consisting of an autoimmune disease, an infectious disease, transplant rejection or graft-versus-host disease, malignancy, a pulmonary disorder, an intestinal disorder, a cardiac disorder, sepsis, a spondyloarthropathy, a metabolic disorder, anemia, pain, a hepatic disorder, a skin disorder, a nail disorder, and vasculitis.

In one embodiment, the autoimmune disorder is selected from the group consisting of rheumatoid arthritis, rheumatoid spondylitis, osteoarthritis, gouty arthritis, allergy, multiple sclerosis, autoimmune diabetes, autoimmune uveitis, and nephrotic syndrome.

In one embodiment, the autoimmune disorder is selected from the group consisting of rheumatoid arthritis, Crohn's disease, ulcerative colitis and rheumatoid arthritis. Preferably, the disorder is selected from Crohn's disease and ulcerative colitis. Ideally the disorder is Crohn's disease.

In another embodiment, the TNFα-related disorder is selected from the group consisting of inflammatory bone disorders, bone resorption disease, alcoholic hepatitis, viral hepatitis, fulminant hepatitis, coagulation disturbances, burns, reperfusion injury, keloid formation, scar tissue formation, pyrexia, periodontal disease, obesity, and radiation toxicity. In still another embodiment, the TNFα-related disorder is selected from the group consisting of Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriatic arthritis, and chronic plaque psoriasis.

In one embodiment of the invention, the TNFα-related disorder is Crohn's disease. In another embodiment, the disorder is ulcerative colitis. In still another embodiment, the disorder is psoriasis. In still another embodiment, the disorder is psoriasis in combination with psoriatic arthritis (PsA). In still another embodiment, the TNFα-related disorder is rheumatoid arthritis.

In one embodiment, the method comprises administration of a second induction dose, subsequent to said first induction dose, which second induction dose is 40% to 60% of said first induction dose. In one embodiment the second induction dose ranges from 81 to 160 mg.

In one embodiment, the treatment dose is 40-60% of the first or second induction dose.

In one embodiment, the treatment dose used in the multiple variable dose regimen of the invention ranges from 41 to 160 mg.

In one embodiment of the invention, the first induction dose comprises 200 mg.

In another embodiment, the treatment dose comprises 80 mg.

In one embodiment, the treatment dose is administered 2 weeks following the induction dose and thereafter the treatment dose is administered biweekly i.e., every other week.

In one embodiment, the anti-TNFα antibody, such as adalimumab or a biosimilar thereof is administered subcutaneously. In another embodiment, the anti-TNFα antibody, such as adalimumab or a biosimilar thereof is administered in combination with methotrexate. The methotrexate can be administered, for example, in a dose of between 2.5 mg and 30 mg.

In one embodiment, the threshold level of a multiple dose method of treatment of Crohn's disease is determined by a reduction in the subject's Crohn's Disease Activity Index (CDAI) score. In another embodiment, the threshold level of a multiple dose method of treatment of Crohn's disease is determined by mucosal healing in a subject having Crohn's Disease.

In one embodiment, the threshold level of a multiple dose method of treatment of psoriasis is determined as a therapeutic effect selected from the group consisting of a reduction in psoriatic plaques, an improvement in the subject's Psoriatic Area Severity Index (PASI), and an improvement in the subject's Physician's Global Assessment (PGA) score.

The invention describes a multiple-variable dose method of inducing remission of Crohn's disease, comprising administering to a subject in need thereof at least one induction dose of of an anti-TNFα antibody, such as adalimumab or a biosimilar thereof which ranges from 161 to 320 mg such that a threshold level of TNFα inhibitor is achieved within an induction phase; and subsequently administering to the subject at least one treatment dose of the anti-TNFα antibody within a treatment phase, such that treatment occurs.

In another embodiment, the invention includes a multiple-variable dose method of reducing psoriatic plaques comprising: administering to a subject in need thereof at least one induction dose of an anti-TNFα antibody, such as adalimumab or a biosimilar thereof which ranges from 81 to 160 mg such that a threshold level of TNFα inhibitor is achieved within an induction phase; and subsequently administering to the subject at least one treatment dose of the anti-TNFα antibody within a treatment phase, such that treatment occurs.

The invention includes a multiple-variable dose method for treating Crohn's disease or ulcerative colitis, comprising administering to a subject in need thereof a first induction dose of 200 mg of adalimumab or a biosimilar thereof, followed by a second induction dose of 100 mg of the antibody two weeks later, followed by, two weeks later, administration of a treatment does of 20, 40, 50, 60, 70, 80, 90, 100, 110, 120 or 160 mg.

In one embodiment, the method is for the treatment of Crohn's disease and the treatment dose is 40 mg or wherein is for the treatment ulcerative colitis and the treatment dose is 50 mg.

In one embodiment more than one treatment dose is administered every other week. The present invention also relates to the following embodiments:

1. An anti-TNFα antibody for use in the treatment of a disorder in which TNFα activity is detrimental, wherein the treatment is to be carried out with a multiple-variable dose comprising a first induction dose of an anti-TNFα antibody which ranges from 161 to 320 mg for administration to a subject in need thereof such that a threshold level of TNFα inhibitor is achieved within an induction phase; and at least one treatment dose of the TNFα inhibitor for subsequent administration within a treatment phase, such that treatment occurs.

2. The anti-TNFα antibody for use according to item 1, wherein said TNFα-related disorder selected from the group consisting of an autoimmune disease, an infectious disease, transplant rejection or graft-versus-host disease, malignancy, a pulmonary disorder, an intestinal disorder, a cardiac disorder, sepsis, a spondyloarthropathy, a metabolic disorder, anemia, pain, a hepatic disorder, a skin disorder, a nail disorder, and vasculitis, optionally wherein the autoimmune disorder is selected from the group consisting of rheumatoid arthritis, rheumatoid spondylitis, osteoarthritis, gouty arthritis, allergy, multiple sclerosis, autoimmune diabetes, autoimmune uveitis, and nephrotic syndrome, alternativey wherein said TNFα-related disorder is selected from the group consisting of inflammatory bone disorders, bone resorption disease, alcoholic hepatitis, viral hepatitis, fulminant hepatitis, coagulation disturbances, burns, reperfusion injury, keloid formation, scar tissue formation, pyrexia, periodontal disease, obesity, and radiation toxicity, alternatively wherein the TNFα-related disorder is selected from the group consisting of Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriatic arthritis, and chronic plaque psoriasis, further alternatively wherein said TNFα-related disorder is Crohn's disease, alternatively wherein the disorder is ulcerative colitis, alternatively wherein, alternatively, wherein the disorder is psoriasis, alternatively wherein the disorder is psoriasis in combination with psoriatic arthritis (PsA), alternatively wherein the TNFα-related disorder is rheumatoid arthritis.

3. The anti-TNFα antibody for use according to item 1 or item 2, wherein said multiple variable dose comprises a second induction dose, for administration subsequent to said first induction dose, optionally which second induction dose is 40% to 60% of said first induction dose.

4 The anti-TNFα antibody for use according to item 3, wherein said second induction dose ranges from 80 to 160 mg.

5. The anti-TNFα antibody for use according to any one of items 1 to 4, wherein said treatment dose is 40-60% of the first or second induction dose.

6. The anti-TNFα antibody for use according to any one of items 1 to 5, wherein said treatment dose ranges from 20 to 160 mg.

7. The anti-TNFα antibody for use according to any one of items 1 to 6, wherein said treatment dose comprises 80 mg.

8. The anti-TNFα antibody for use according to any one of items 1 to 7, wherein said first induction dose comprises 200 mg.

9. The anti-TNFα antibody for use according to any one of items 1 to 8, wherein said treatment dose is for administration 2 weeks following the induction dose.

10. The anti-TNFα antibody for use according to any one of items 1 to 9, wherein said anti-TNFα antibody is for subcutaneous administration.

11. The anti-TNFα antibody for use according to any one of items 1 to 10, wherein said anti-TNFα antibody is adalimumab or a biosimilar thereof.

12. The anti-TNFα antibody for use according to any one of items 1 to 11, wherein said anti-TNFα antibody is for administration in combination with methotrexate.

13. Adalimumab or a biosimilar thereof for use in the treatment of Crohn's disease or ulcerative colitis, wherein the treatment comprises a multiple-variable dose comprising a first induction dose of 200 mg of adalimumab or a biosimilar thereof for administration to a subject in need thereof, followed by a second induction dose of 100 mg of the adalimumab or biosimilar thereof for administration to the subject in need thereof two weeks later, followed by a treatment does of 20, 40, 50, 60, 70, 80, 90, 100, 110, 120 or 160 mg of the adalimumab or biosimilar thereof for administration, two weeks later, to the subject in need thereof.

14. The adalimumab or biosimilar thereof for use according to item 13, wherein the adalimumab or biosimilar thereof is for use in the treatment of Crohn's disease and the treatment dose is 40 mg or wherein the adalimumab or biosimilar thereof is for use in the treatment ulcerative colitis and the treatment dose is 50 mg.

15. The adalimumab or biosimilar thereof for use according to items 13 or 14, wherein the treatment dose is for administration on a biweekly dosing regimen.

16. The anti-TNFα antibody for use according to any one of items 1 to 12 or the adalimumab or biosimilar thereof for use according to any one of items 13 to 15, wherein said anti-TNFα antibody or said adalimumab or biosimilar thereof is for subcutaneous administration in a liquid formulation containing 100 mg/ml of said anti-TNFα antibody or adalimumab or biosimilar thereof.

Further, the present invention relates to the following embodiments:

17. An anti-TNFα antibody for use in the treatment of a disorder in which TNFα activity is detrimental, wherein the treatment is to be carried out with a multiple-variable dose comprising a first induction dose of an anti-TNFα antibody which ranges from 161 to 320 mg for administration to a subject in need thereof such that a threshold level of TNFα inhibitor is achieved within an induction phase; and at least one treatment dose of the TNFα inhibitor for subsequent administration within a treatment phase, such that treatment occurs; and wherein said anti-TNFα antibody or said adalimumab becomes injected through a needle with an outer diameter between 0.1 and 5 mm.

18. The anti-TNFα antibody for use according to item 17, wherein said TNFα-related disorder selected from the group consisting of an autoimmune disease, an infectious disease, transplant rejection or graft-versus-host disease, malignancy, a pulmonary disorder, an intestinal disorder, a cardiac disorder, sepsis, a spondyloarthropathy, a metabolic disorder, anemia, pain, a hepatic disorder, a skin disorder, a nail disorder, vasculitis, rheumatoid arthritis, rheumatoid spondylitis, osteoarthritis, gouty arthritis, allergy, multiple sclerosis, autoimmune diabetes, autoimmune uveitis, nephrotic syndrome, inflammatory bone disorders, bone resorption disease, alcoholic hepatitis, viral hepatitis, fulminant hepatitis, coagulation disturbances, burns, reperfusion injury, keloid formation, scar tissue formation, pyrexia, periodontal disease, obesity, radiation toxicity, Behcet's disease, ankylosing spondylitis, asthma, chronic obstructive pulmonary disorder (COPD), idiopathic pulmonary fibrosis (IPF), restenosis, diabetes, a Crohn's disease-related disorder, juvenile rheumatoid arthritis (JRA), a hepatitis C virus infection, psoriatic arthritis, chronic plaque psoriasis, Crohn's disease, ulcerative colitis, psoriasis, psoriasis in combination with psoriatic arthritis (PsA) and rheumatoid arthritis.

19. The anti-TNFα antibody for use according to item 17 or item 18, wherein said multiple variable dose comprises a second induction dose, for administration subsequent to said first induction dose, optionally which second induction dose is 40% to 60% of said first induction dose.

20. The anti-TNFα antibody for use according to item 19, wherein said second induction dose ranges from 80 to 160 mg.

21. The anti-TNFα antibody for use according to any one of items 17 to 20, wherein said treatment dose is 40-60% of the first or second induction dose.

22. The anti-TNFα antibody for use according to any one of items 17 to 21, wherein said treatment dose ranges from 20 to 160 mg.

23. The anti-TNFα antibody for use according to any one of items 17 to 22, wherein said treatment dose comprises 80 mg.

24. The anti-TNFα antibody for use according to any one of items 17 to 23, wherein said first induction dose comprises 200 mg.

25. The anti-TNFα antibody for use according to any one of items 17 to 24, wherein said treatment dose is for administration 2 weeks following the induction dose.

26. The anti-TNFα antibody for use according to any one of items 17 to 25, wherein said anti-TNFα antibody is for subcutaneous administration.

27. The anti-TNFα antibody for use according to any one of items 17 to 26, wherein said anti-TNFα antibody is adalimumab.

28. The anti-TNFα antibody for use according to any one of items 17 to 27, wherein said anti-TNFα antibody is for administration in combination with methotrexate.

29. Adalimumab for use in the treatment of Crohn's disease or ulcerative colitis, wherein the treatment comprises a multiple-variable dose comprising a first induction dose of 200 mg of adalimumab for administration to a subject in need thereof, followed by a second induction dose of 100 mg of the adalimumab for administration to the subject in need thereof two weeks later, followed by a treatment does of 20, 40, 50, 60, 70, 80, 90, 100, 110, 120 or 160 mg of the adalimumab for administration, two weeks later, to the subject in need thereof; and wherein said anti-TNFα antibody or said adalimumab becomes injected through a needle with an outer diameter between 0.1 and 5 mm.

30. The adalimumab for use according to item 29, wherein the adalimumab is for use in the treatment of Crohn's disease and the treatment dose is 40 mg or wherein the adalimumab is for use in the treatment ulcerative colitis and the treatment dose is 50 mg.

31. The adalimumab for use according to items 29 or 30, wherein the treatment dose is for administration on a biweekly dosing regimen.

32. The anti-TNFα antibody for use according to any one of items 17 to 28 or the adalimumab for use according to any one of items 29 to 31, wherein said anti-TNFα antibody or said adalimumab is for subcutaneous administration in a liquid formulation containing 100 mg/ml of said anti-TNFα antibody or adalimumab.

33. The anti-TNFα antibody or the adalimumab for use according to any of the preceding items, wherein said anti-TNFα antibody or said adalimumab becomes injected through a needle with an outer diameter between 0.25 and 0.5 mm.

DETAILED DESCRIPTION OF THE INVENTION

I. Definitions

In order that the present invention may be more readily understood, certain terms are first defined.

The term "human TNF-alpha" (abbreviated herein as hTNF-alpha, TNFα, or simply hTNF), as used herein, is intended to refer to a human cytokine that exists as a 17 kDa secreted form and a 26 kDa membrane associated form, the biologically active form of which is composed of a trimer of noncovalently bound 17 kDa molecules. The structure of hTNF-alpha is described further in, for example, Pennica, D., et al. (1984) Nature 312:724-729; Davis, J. M., et al. (1987) Biochem 26: 1322-1326; and Jones, E. Y., et al. (1989) Nature 338:225-228. The term human TNF-alpha is intended to include recombinant human TNF-alpha (rhTNF-alpha), which can be prepared by standard recombinant expression methods or purchased commercially (R & D Systems, Catalog No. 210-TA, Minneapolis, Minn.).

The term "anti-TNFα antibody" is intended to refer to an isolated human antibody or an antigen-binding portion thereof. Preferably the human anti-TNFα antibody, or an antigen-binding portion thereof, comprises the CDRs corresponding to adalimumab (also referred to as Humira®, adalimumab, or D2E7; Abbott Laboratories). More preferably the human antibody is adalimumab, or a biosimilar thereof.

The term "antibody," as used herein, is intended to refer to immunoglobulin molecules comprised of four polypeptide chains, two heavy (H) chains and two light (L) chains inter-connected by disulfide bonds. Other naturally occurring antibodies of altered structure, such as, for example, camelid antibodies, are also included in this definition. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In one embodiment of the invention, the formulation contains an antibody with CDR1, CDR2, and CDR3 sequences like those described in U.S. Pat. Nos. 6,090,382 and 6,258, 562, each incorporated by reference herein. In certain embodiments, the formulation contains an antibody as claimed in U.S. Pat. Nos. 6,090,382 and 6,258,562. As used herein, the term "CDR" refers to the complementarity determining region within a antibody variable sequence. There are three CDRs in each of the variable regions of the heavy chain and the light chain, which are designated CDR1, CDR2 and CDR3, for each of the heavy and light chain variable regions. The exact boundaries of these CDRs have been defined differently according to different systems. The system described by Kabat (Id.) not only provides an unambiguous residue numbering system applicable to any variable region of an antibody, but also provides precise residue boundaries defining the three CDRs. These CDRs may be referred to as Kabat CDRs. Chothia et al. found that certain sub-portions within Kabat CDRs adopt nearly identical peptide backbone conformations, despite having great diversity at the level of amino acid sequence (Chothia et al. (1987) Mol. Biol. 196:901-917; Chothia et al. (1989) Nature 342:877-883) These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (1995) FASEB J. 9: 133-139 and MacCallum (1996) J. Mol. Biol. 262(5):732-45. Still other CDR boundary definitions may not strictly follow one of the herein described systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs. In one embodiment, the antibody used in the methods and compositions of the invention includes the six CDRs from the antibody adalimumab.

The term "antigen-binding portion" of an antibody (or simply "antibody portion"), as used herein, refers to one or more fragments of an antibody that retain the ability to specifically bind to an antigen {e.g., hTNF-alpha). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2: 1121-1123). In one embodiment of the invention, the formulation contains an antigen-binding portions described in U.S. Pat. Nos. 6,090,382 and 6,258,562, each incorporated by reference herein.

The phrase "recombinant antibody" refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal {e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of particular immunoglobulin gene sequences (such as human immunoglobulin gene sequences) to other DNA sequences. Examples of recombinant antibodies include recombinant human, chimeric, CDR-grafted and humanized antibodies.

The term "human antibody," as used herein, is intended to include antibodies having variable and constant regions derived from human germline immunoglobulin sequences. The human antibodies used in the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

An "isolated antibody," as used herein, is intended to refer to an antibody that is substantially free of other antibodies having different antigenic specificities (e.g., an isolated antibody that specifically binds hTNF-alpha is substantially free of antibodies that specifically bind antigens other than hTNF-alpha). An isolated antibody that specifically binds hTNF-alpha may, however, have cross-reactivity to other antigens, such as TNF-alpha molecules from other species. Moreover, an isolated antibody may be substantially free of other cellular material and/or chemicals.

A "neutralizing antibody," as used herein (or an "antibody that neutralized hTNF-alpha activity"), is intended to refer to an antibody whose binding to hTNF-alpha results in inhibition of the biological activity of hTNF-alpha. This inhibition of the biological activity of hTNF-alpha can be assessed by measuring one or more indicators of hTNF-alpha biological activity, such as hTNF-alpha-induced cytotoxicity (either in vitro or in vivo), hTNF-alpha-induced cellular activation and hTNF-alpha binding to hTNF-alpha receptors. These indicators of hTNF-alpha biological activity can be assessed by one or more of several standard in vitro or in vivo assays known in the art, and described in U.S. Pat. Nos. 6,090,382 and 6,258,562, each incorporated by reference herein. In one embodiment, the ability of an antibody to neutralize hTNF-alpha activity is assessed by inhibition of hTNF-alpha-induced cytotoxicity of L929 cells. As an additional or alternative parameter of hTNF-alpha activity, the ability of an antibody to inhibit hTNF-alpha-induced expression of ELAM-1 on HUVEC, as a measure of hTNF-alpha-induced cellular activation, can be assessed.

The term "surface plasmon resonance," as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51: 19-26; Jonsson, U., et al. (1991) Biotechniques 11:620-627; Johnsson, B., et al. (1995) J. Mol. Recognit. 8: 125-131; and Johnnson, B., et al. (1991) Anal. Biochem. 198: 268-277.

The term "$K_{on}$," as used herein, is intended to refer to the on rate constant for association of a binding protein (e.g., an antibody) to the antigen to form the, e.g., antibody/antigen complex as is known in the art.

The term "$K_{off}$" as used herein, is intended to refer to the off rate constant for dissociation of an antibody from the antibody/antigen complex.

The term "$K_d$" as used herein, is intended to refer to the dissociation constant of a particular antibody-antigen interaction and refers to the value obtained in a titration measurement at equilibrium, or by dividing the dissociation rate constant ($K_{off}$) by the association rate constant ($K_{on}$).

As used herein, "biosimilar" (of an approved reference product/biological drug, such as a protein therapeutic, antibody, etc.) refers to a biologic product that is similar to the reference product based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biological product. In one embodiment, the biosimilar biological product and reference product utilize the same mechanism or mechanisms of action for the condition or conditions of use prescribed, recommended, or suggested in the proposed labeling, but only to the extent the mechanism or mechanisms of action are known for the reference product. In one embodiment, the condition or conditions of use prescribed, recommended, or suggested in the labeling proposed for the biological product have been previously approved for the reference product. In one embodiment, the route of administration, the dosage form, and/or the strength of the biological product are the same as those of the reference product. In one embodiment, the facility in which the biological product is manufactured, processed, packed, or held meets standards designed to assure that the biological product continues to be safe, pure, and potent. The reference product may be approved in at least one of the U.S., Europe, or Japan.

The term "dose" as used herein, refers to an amount of TNFα inhibitor which is administered to a subject.

The term "multiple-variable dose" includes different doses of a TNFα inhibitor which are administered to a subject for therapeutic treatment. "Multiple-variable dose regimen" or "multiple-variable dose therapy" describe a treatment schedule which is based on administering different amounts of TNFα inhibitor at various time points throughout the course of treatment. In one embodiment, the invention describes a multiple-variable dose method of treatment comprising an induction phase and a treatment phase, wherein a TNFα inhibitor is administered at a higher dose during the induction phase than the treatment phase.

The term "induction phase" or "loading phase", as used herein, refers to a period of treatment comprising administration of a TNFα inhibitor to a subject in order to attain a threshold level. During the induction phase, at least one induction dose of TNFα inhibitor is administered to a subject suffering from a disorder in which TNFα is detrimental.

The term "threshold level", as used herein, refers to a therapeutically effective level of a TNFα inhibitor in a subject. A threshold level is achieved by administering at least one induction dose during the induction phase of treatment. Any number of induction doses may be administered to achieve a threshold level of TNFα inhibitor.

Once a threshold level is achieved, the treatment phase is initiated.

The term "induction dose" or "loading dose" used interchangeably herein, refers to the first dose of TNFα inhibitor, which is larger in comparison to the maintenance or treatment dose. The induction dose can be a single dose or, alternatively, a set of doses.

The induction dose is often used to bring the drug in the body to a steady state amount, and may be used to which to achieve maintenance drug levels quickly. An induction dose is subsequently followed by administration of smaller doses of TNFα inhibitor, i.e., the treatment dose. The induction dose is administered during the induction phase of therapy. In one embodiment of the invention, the induction dose is at least twice the given amount of the treatment dose.

The term "treatment phase" or "maintenance phase", as used herein, refers to a period of treatment comprising administration of a TNFα inhibitor to a subject in order to maintain a desired therapeutic effect. The treatment phase follows the induction phase, and, therefore, is initiated once a threshold level is achieved.

The term "treatment dose" or "maintenance dose" is the amount of TNFα inhibitor taken by a subject to maintain or continue a desired therapeutic effect. A treatment dose is administered subsequent to the induction dose. A treatment dose can be a single dose or, alternatively, a set of doses. A treatment dose is administered during the treatment phase of therapy. Treatment doses are smaller than the induction dose and can be equal to each other when administered in succession. In still another embodiment, the treatment dose is administered at least two weeks following the induction dose.

A "dosage regimen" or "dosing regimen" includes a treatment regimen based on a determined set of doses. In one embodiment, the invention describes a dosage regimen for the treatment of Crohn's disease, wherein adalimumab is first administered as an induction dose and then administered in treatment doses which are lower than that of the induction dose.

The term "dosing", as used herein, refers to the administration of a substance (e. g., an anti-TNFα antibody) to achieve a therapeutic objective (e. g., the treatment of a TNFα-associated disorder).

The terms "biweekly dosing regimen", "biweekly dosing", and "biweekly administration", as used herein, refer to the time course of administering a substance (e. g., an anti-TNFα antibody) to a subject to achieve a therapeutic objective (e.g., the treatment of a TNFα-associated disorder). The biweekly dosing regimen is not intended to include a weekly dosing regimen. Preferably, the substance is administered every 9-19 days, more preferably, every 11-17 days, even more preferably, every 13-15 days, and most preferably, every 14 days.

The terms "monthly dosing regimen", "monthly dosing", and "monthly administration", as used herein, refer to a certain time course (or periodicity) of administering a substance (e.g., an anti-TNFα antibody) to a subject to achieve a therapeutic objective (e.g., the treatment of a TNFα-associated disorder). In one embodiment, a monthly dosing regimen means that the antibody, or antigen-binding portion thereof, is administered every 28-31 days. In another embodiment, a monthly dosing regimen means that the antibody, or antigen-binding portion thereof, is administered once a month, e.g. on the same day each month, such as, for example, the first day of each month.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g. human).

The term "combination therapy", as used herein, refers to the administration of two or more therapeutic substances, e. g., an anti-TNFα antibody and another drug, such as a DMARD or NSAID. The other drug (s) be administered concomitant with, prior to, or following the administration of an anti-TNFα antibody.

The term "TNFα-mediated condition" or "TNFα-related disorder" refers to a local and/or systemic physiological disorder where TNFα is a primary mediator leading to the manifestation of the disorder.

The term "kit" as used herein refers to a packaged product comprising components with which to administer the TNFα antibody of the invention for treatment of a TNFα-related disorder. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering the TNFα antibody of the invention. In one embodiment the kit of the invention includes the formulation comprising the human antibody adalimumab, as described in PCT/IB03/04502 and U.S. application Ser. No. 10/222,140.

Various aspects of the invention are described in further detail herein.

II. Antibodies for Use in the Invention

This invention provides a multiple-variable dose method of treating a TNFα related disorder in which the administration of a TNFα inhibitor is beneficial.

The methods of the invention include an antibody, or antigen binding portion thereof, particularly an anti-TNFα antibody, or antigen binding portion or fragment thereof. Examples of antibodies that may be used in the invention include chimeric antibodies, non-human antibodies, isolated human antibodies, humanized antibodies, and domain antibodies (dAbs). All antibodies described herein may be used in the methods of the invention as well.

In one embodiment, the methods of the invention include an antibody, or antigen-binding portion thereof, which binds human TNFα, including, for example, adalimumab (also referred to as Humira, adalimumab, or D2E7; Abbott Laboratories) or a biosimilar thereof. In a further embodiment, the the methods include an antibody that binds the same epitope as adalimumab, such as, but not limited to, an adalimumab biosimilar antibody. In one embodiment, the antibody is a human IgGI antibody having six CDRs corresponding to those of the light and heavy chain of adalimumab.

References herein to "adalimumab" include the originator drug substance (as commercially available under the name Humira), adalimumab as defined in WO97/29131 (BASF) (particularly D2E7 therein) and elsewhere in the art, and also biosimilars thereof.

In one embodiment, the invention uses an isolated human antibody, or antigen-binding portion thereof, that binds to human TNF-alpha with high affinity and a low off rate, and also has a high neutralizing capacity. In one embodiment, the human antibodies used in the invention are recombinant, neutralizing human anti-hTNF-alpha antibodies.

In one aspect, the invention pertains to adalimumab antibodies and antibody portions, adalimumab-related antibodies and antibody portions, and other human antibodies and antibody portions with equivalent properties to adalimumab, such as high affinity binding to hTNFα with low dissociation kinetics and high neutralizing capacity. In one embodiment, the antibody, or antigen-binding fragment thereof, is defined according to dissociation and binding characteristics similar to adalimumab. For example, the formulation may include a human antibody that dissociates from human TNFα with a $K_d$ of $1\times10^{-8}$ M or less, and a $K_{off}$ rate constant of $1\times10^{-3}$ s$^{-1}$ or less, both determined by surface plasmon resonance. In another embodiment, the human antibody that dissociates from human TNFα with a $K_d$ of $1\times10^{-9}$ M or less.

In one embodiment, the antibody, or antigen-binding fragment thereof, is a human antibody that dissociates from human TNFα with a $K_d$ of $1\times10^{-8}$ M or less, and a $k_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less. Examples and methods for making human, neutralizing antibodies which have a high affinity for human TNFα, including sequences of the antibodies, are described in U.S. Pat. No. 6,090,382 (referred to as D2E7), incorporated by reference herein. The amino sequences of D2E7 as described in U.S. Pat. No. 6,090,382 are incorporated in their entirety herein.

In one embodiment, the antibody used in the methods of the invention is D2E7, also referred to as HUMIRA™ or adalimumab (the amino acid sequence of the D2E7 VL region is shown in SEQ ID NO: 1; the amino acid sequence of the D2E7 VH region is shown in SEQ ID NO: 2). The properties of D2E7 (adalimumab/HUMIRA®) have been described in Salfeld et al., U.S. Pat. Nos. 6,090,382, 6,258,562, and 6,509,015, which are each incorporated by reference herein. In one embodiment, the antibody used in the methods of the invention is a biosimilar of adalimumab.

In one embodiment, the human anti-TNF-alpha antibody, or an antigen-binding portion thereof, dissociates from human TNF-alpha with a $K_d$ of $1\times10^{-8}$ M or less and a $k_{off}$ rate constant of $1\times10^{-3}$ s$^{-1}$ or less, both determined by surface plasmon resonance, and neutralizes human TNF-alpha cytotoxicity in a standard in vitro L929 assay with an IC$_{50}$ of $1\times10^{-7}$ M or less. In one embodiment, the isolated human antibody, or antigen-binding portion thereof, dissociates from human TNF-alpha with a $k_{off}$ of $5\times10^{-4}$ s$^{-1}$ or less; or, in one embodiment, with a $k_{off}$ Of $1\times10^{-4}$ s$^{-1}$ or less. In one embodiment, the isolated human antibody, or antigen-binding portion thereof, neutralizes human TNF-alpha cytotoxicity in a standard in vitro L929 assay with an IC$_{50}$ of $1\times10^{-8}$ M or less; or, in one embodiment, with an IC$_{50}$ of $1\times10^{-9}$ M or less; or, in one embodiment, with an IC$_{50}$ of $1\times10^{-10}$ M or less. In one embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the antibody used in the methods of the invention has slow dissociation kinetics for association with hTNF-alpha and has light and heavy chain CDR3 domains that structurally are identical to or related to those of adalimumab. Position 9 of the adalimumab VL CDR3 can be occupied by Ala or Thr without substantially affecting the Koff. Accordingly, a consensus motif for the adalimumab VL CDR3 comprises the amino acid sequence: Q-R-Y-N-R-A-P-Y-(T/A) (SEQ ID NO: 3). Additionally, position 12 of the adalimumab VH CDR3 can be occupied by Tyr or Asn, without substantially affecting the Koff. Accordingly, a consensus motif for the adalimumab VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the adalimumab heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $k_{off}$. Still further, the skilled artisan will appreciate that, given the amenability of the adalimumab VL and VH CDR3 domains to substitutions by alanine, substitution of other amino acids within the CDR3 domains may be possible while still retaining the low off rate constant of the antibody, in particular substitutions with conservative amino acids. In one embodiment, no more than one to five conservative amino acid substitutions are made within the adalimumab VL and/or VH CDR3 domains. In one embodiment, no more than one to three conservative amino acid substitutions are made within the adalimumab VL and/or VH CDR3 domains.

Additionally, conservative amino acid substitutions should not be made at amino acid positions critical for binding to hTNF alpha. Positions 2 and 5 of the adalimumab VL CDR3 and positions 1 and 7 of the adalimumab VH CDR3 appear to be critical for interaction with hTNF alpha, and thus, conservative amino acid substitutions preferably are not made at these positions (although an alanine substitution at position 5 of the adalimumab VL CDR3 is acceptable, as described above) (see U.S. Pat. No. 6,090,382).

Accordingly, in one embodiment, the antibody or antigen-binding portion thereof, used in the formulation of the invention contains the following characteristics: a) dissociates from human TNFα with a koff rate constant of $1\times10^{-3}$ $s^{-1}$ or less, as determined by surface plasmon resonance; b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9; c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In certain embodiments, the antibody or antigen-binding portion thereof, dissociates from human TNF-alpha with a koff of $5\times10^{-4}$ $s^{-1}$ or less. In certain embodiments, the antibody or antigen-binding portion thereof, dissociates from human TNF-alpha with a $k_{off}$ of $1\times10^{-4}$ $s^{-1}$ or less.

In yet another embodiment, the antibody or antigen-binding portion thereof contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. In one embodiment, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). In one embodiment, the LCVR further has CDR1 domain comprising the amino acid sequence of SEQ ID NO: 7 (i.e. the D2E7 VL CDR1) and the HCVR has a CDR1 domain comprising the amino acid sequence of SEQ ID NO: 8 (i.e. the D2E7 VH CDR1). The framework regions for VL may be from the VKI human germline family, or from the A20 human germline Vk gene, or from the adalimumab VL framework sequences shown in FIGS. 1A and 1B of U.S. Pat. No. 6,090,382. The framework regions for VH may be from the VH3 human germline family, or from the DP-31 human germline VH gene, or from the D2E7 VH framework sequences shown in FIGS. 2A and 2B of U.S. Pat. No. 6,090,382. Nucleic acid sequences corresponding to the adalimumab light and heavy variable regions are described in SEQ ID NOs: 36 and 37, respectively. Accordingly, in another embodiment, the antibody or antigen-binding portion thereof contains a light chain variable region (LCVR) comprising the amino acid sequence of SEQ ID NO: 1 (i.e., the adalimumab VL) and a heavy chain variable region (HCVR) comprising the amino acid sequence of SEQ ID NO: 2 (i.e., the adalimumab VH). In certain embodiments, the antibody comprises a heavy chain constant region, such as an IgGI, IgG2, IgG3, IgG4, IgA, IgE, IgM or IgD constant region. In certain embodiments, the heavy chain constant region is an IgGI heavy chain constant region or an IgG4 heavy chain constant region. Furthermore, the antibody can comprise a light chain constant region, either a kappa light chain constant region or a lambda light chain constant region. In one embodiment, the antibody comprises a kappa light chain constant region. Alternatively, the antibody portion can be, for example, a Fab fragment or a single chain Fv fragment.

An antibody, or antibody portion, used in the methods and compositions of the invention, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al. To express an anti-TNFa antibody, e.g., adalimumab (D2E7) or an adalimumab (D2E7)-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals Fifty Groups of VH Segments with Different Hypervariable Loops" J. Mol. Biol. 227:776-798; and Cox, J. P. L. et al. (1994) "A Directory of Human Germ-line V78 Segments Reveals a Strong Bias in their Usage" Eur. J. Immunol. 24:827-836; the contents of each of which are expressly incorporated herein by reference). For example, to obtain a DNA fragment encoding the heavy chain variable region of D2E7, or a D2E7-related antibody, a member of the VH3 family of human germline VH genes is amplified by standard PCR. In certain embodiments, the DP-31 VH germline sequence is amplified. To obtain a DNA fragment encoding the light chain variable region of D2E7, or a D2E7-related antibody, a member of the VKI family of human germline VL genes is amplified by standard PCR. In certain embodiments, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the anti-TNFa antibody amino acid sequences disclosed herein. The amino acid sequences encoded by the germline VH and VL DNA sequences are first compared to the anti-TNFa antibody VH and VL amino acid sequences to identify amino acid residues in the anti-TNFa antibody sequence that differ from germline.

Then, the appropriate nucleotides of the germline DNA sequences are mutated such that the mutated germline sequence encodes the anti-TNFa antibody amino acid sequence, using the genetic code to determine which nucleotide changes should be made.

Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Moreover, it should be noted that if the "germline" sequences obtained by PCR amplification encode amino acid differences in the framework regions from the true germline configuration (i.e. differences in the amplified sequence as compared to the true germline sequence, for example as a result of somatic mutation), it may be desirable to change these amino acid differences back to the true germline sequences (i.e. "backmutation" of framework residues to the germline configuration).

Once DNA fragments encoding the anti-TNFa antibody VH and VL segments are obtained (e.g. by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame. The isolated DNA encoding the VH region can be converted to a full-length heavy chain gene by operatively linking the VH-encoding DNA to another DNA molecule encoding heavy chain constant regions (CHI, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgGI, IgG2, IgG3, IgG4, IgA, IgE, IgM or IgD constant region, but most preferably is an IgGI or IgG4 constant region. For a Fab fragment heavy chain gene, the VH-encoding DNA can be operatively linked to another DNA molecule encoding only the heavy chain CHI constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. In one embodiment, the light chain constant region is a kappa constant region.

To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al, Nature (1990) 348:552-554).

To express the antibodies, or antibody portions used in the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the anti-TNFa antibody light or heavy chain sequences, the expression vector may already carry antibody constant region sequences. For example, one approach to converting the anti-TNFa antibody VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e. a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g. polyadenylation signals) that control the transcription or translation of the antibody chain genes. Such regulatory sequences are described, for example, in Goeddel; Gene Expression Technology: Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc.

Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors used in the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr– host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies is preferably in eukaryotic cells. In one embodiment, mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6: 12-13).

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 160:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more, in one embodiment, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNF alpha. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNF alpha by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. In view of the foregoing, nucleic acid, vector and host cell compositions that can be used for recombinant expression of the antibodies and antibody portions used in the invention include nucleic acids, and vectors comprising said nucleic acids, comprising the human TNF alpha antibody adalimumab (D2E7). The nucleotide sequence encoding the D2E7 light chain variable region is shown in SEQ ID NO: 36. The CDRI domain of the LCVR encompasses nucleotides 70-102, the CDR2 domain encompasses nucleotides 148-168 and the CDR3 domain encompasses nucleotides 265-291. The nucleotide sequence encoding the D2E7 heavy chain variable region is shown in SEQ ID NO: 37. The CDRI domain of the HCVR encompasses nucleotides 91-105, the CDR2 domain encompasses nucleotides 148-198 and the CDR3 domain encompasses nucleotides 295-330. It will be appreciated by the skilled artisan that nucleotide sequences encoding D2E7-related antibodies, or portions thereof (e.g., a CDR domain, such as a CDR3 domain), can be derived from the nucleotide sequences encoding the D2E7 LCVR and HCVR using the genetic code and standard molecular biology techniques.

In one embodiment, the antibody comprises a human TNF alpha antibody, or antigen-binding portion thereof, that is a bioequivalent or biosimilar to the antibody adalimumab. In one embodiment, a biosimilar antibody is an antibody which shows no clinically meaningful difference when compared to a reference antibody, e.g., adalimumab. A biosimilar antibody has equivalent safety, purity, and potency as a reference antibody, e.g., adalimumab.

III. Methods of the Invention

The invention provides a multiple-variable dose method for inhibiting TNFα activity in a subject suffering from a disorder in which TNFα activity is detrimental.

TNFα has been implicated in the pathophysiology of a wide variety of disorders (see e. g., Moeller, A., et al. (1990) Cytokine 2:162-169; U.S. Pat. No. 5,231,024 to Moeller et al.; European Patent Publication No. 260 610 B1 by Moeller, A.). TNFα has been implicated in the pathophysiology of a wide variety of a TNFα-related disorders including sepsis, infections, autoimmune diseases, transplant rejection and graft-versushost disease (see e.g., Moeller, A., et al. (1990) Cytokine 2: 162-169; U.S. Pat. No. 5,231,024 to Moeller et al.; European Patent Publication No. 260 610 B by Moeller, A., et al. Vasilli, P. (1992) Annu. Rev. Immunol. 10:411-452; Tracey, K. J. and Cerami, A. (1994) Annu. Rev. Med. 45:491-503). The invention provides multiple-variable dose methods for inhibiting TNFα activity in a subject suffering from a TNFα-related disorder, which method comprises administering to a subject an initial induction dose and subsequently administering a treatment dose of an anti TNFα antibody or antibody portion, such that TNFα activity is inhibited. Preferably, the TNFα is human TNFα and the subject is a human subject. In one embodiment, the TNFα inhibitor is adalimumab, also referred to as HUMIRA or D2E7, or a biosimilar thereof.

As used herein, the term "a disorder in which TNFα activity is detrimental" is intended to include diseases and other disorders in which the presence of TNFα in a subject suffering from the disorder has been shown to be or is suspected of being either responsible for the pathophysiology of the disorder or a factor that contributes to a worsening of the disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e. g., an increase in the concentration of TNFα in serum, plasma, synovial fluid, etc. of the subject), which can be detected, for example, using an anti-TNFα antibody as described above. There are numerous examples of disorders in which TNFα activity is detrimental. The use of TNFα inhibitors, including antibodies and antibody portions, of the invention in the treatment of specific disorders using a multiple-variable dose therapy is discussed further below:

A. Sepsis

The methods of the invention may be used to treat subjects having sepsis. Tumor necrosis factor has an established role in the pathophysiology of sepsis, with biological effects that include hypotension, myocardial suppression, vascular leakage syndrome, organ necrosis, stimulation of the release of toxic secondary mediators and activation of the clotting cascade (see e. g., Moeller, A., et al. (1990) Cytokine 2:162-169; U.S. Pat. No. 5,231,024 to Moeller et al.; European Patent Publication No. 260 610 B1 by Moeller, A.; Tracey, K. J. and Cerami, A. (1994) Annu. Rev. Med. 45: 491-503; Russell, D and Thompson, R. C. (1993) Curr. Opin. Biotech. 714-721). The multiple-variable dose methods of the invention can be used to treat sepsis in any of its clinical settings, including septic shock, endotoxic shock, gram negative sepsis and toxic shock syndrome.

Furthermore, to treat sepsis, an anti-hTNFα antibody, or antibody portion, of the invention can be coadministered with one or more additional therapeutic agents that may further alleviate sepsis, such as an interleukin-1 inhibitor (such as those described in PCT Publication Nos. WO 92/16221 and WO 92/17583), the cytokine interleukin-6 (see e. g., PCT Publication No. WO 93/11793) or an antagonist of platelet activating factor (see e. g., European Patent Application Publication No. EP 374 510). Other combination therapies including multiple-variable dose therapies for the treatment of sepsis are discussed further in subsection IV. In a preferred embodiment, an anti-TNFα antibody or antibody portion is administered to a human subject within a subgroup of sepsis patients having a serum or plasma concentration of IL-6 above 500 pg/ml, and more preferably 1000 pg/ml, at the time of treatment (see PCT Publication No. WO 95/20978 by Daum, L, et al.).

B. Autoimmune Diseases

The methods of the invention may be used to treat subjects having an autoimmune disease.

The formulations and methods of the invention may be used to treat subjects having an autoimmune disease. Tumor necrosis factor has been implicated in playing a role in the pathophysiology of a variety of autoimmune diseases. For example, TNF-alpha has been implicated in activating tissue inflammation and causing joint destruction in rheumatoid arthritis (see e.g., Tracey and Cerami, supra; Arend, W. P. and Dayer, J-M. (1995) Arth. Rheum. 38: 151-160; Fava, R. A., et al. (1993) Clin. Exp. Immunol. 94:261-266). TNF-alpha also has been implicated in promoting the death of islet cells and in mediating insulin resistance in diabetes (see e.g., Tracey and Cerami, supra; PCT Publication No. WO 94/08609). TNF-alpha also has been implicated in mediating cytotoxicity to oligodendrocytes and induction of inflammatory plaques in multiple sclerosis (see e.g., Tracey and Cerami, supra). Also included in autoimmune diseases that may be treated using the formulations and methods of the invention is juvenile idiopathic arthritis (JIA) (also referred to as juvenile rheumatoid arthritis) (see Grom et al. (1996) Arthritis Rheum. 39: 1703; Mangge et al. (1995) Arthritis Rheum. 8:211).

The methods of the invention can be used to treat autoimmune diseases, in particular those associated with inflammation, including rheumatoid arthritis, rheumatoid spondylitis (also referred to as ankylosing spondylitis), osteoarthritis and gouty arthritis, allergy, multiple sclerosis, autoimmune diabetes, autoimmune uveitis, juvenile idiopathic arthritis (also referred to as juvenile rheumatoid arthritis), and nephrotic syndrome.

Another autoimmune disease which can be treated using the multiple-variable dose treatment of the invention is Crohn's disease, which is described in more detail below in the Intestinal Disorders Section.

C. Infectious Diseases

The methods of the invention may be used to treat subjects having an infectious disease. Tumor necrosis factor has been implicated in mediating biological effects observed in a variety of infectious diseases. For example, TNFα has been implicated in mediating brain inflammation and capillary thrombosis and infarction in malaria. TNFα also has been implicated in mediating brain inflammation, inducing breakdown of the blood-brain barrier, triggering septic shock syndrome and activating venous infarction in meningitis. TNFα also has been implicated in inducing cachexia, stimulating viral proliferation and mediating central nervous system injury in acquired immune deficiency syndrome (AIDS). Accordingly, antibodies, and antibody portions, directed against TNF, can be used in multiple-variable dose treatment of infectious diseases, including bacterial meningitis (see e.g., European Patent Application Publication No. EP 585 705), cerebral malaria, AIDS and AIDS-related complex (ARC) (see e.g., European Patent Application Publication No. EP 230 574), as well as cytomegalovirus infection secondary to transplantation (see e.g., Fietze et al. (1994) Transplantation 58:675). The antibodies, and antibody portions, of the invention, also can be used to alleviate symptoms associated with infectious diseases, including fever and myalgias due to infection (such as influenza) and cachexia secondary to infection (e.g., secondary to AIDS or ARC).

D. Transplantation

The methods of the invention may be used to treat subjects having a transplantation. Tumor necrosis factor has been implicated as a key mediator of allograft rejection and graft versus host disease (GVHD) and in mediating an adverse reaction that has been observed when the rat antibody OKT3, directed against the T cell receptor CD3 complex, is used to inhibit rejection of renal transplants (see e. g., Eason et al. (1995) Transplantation 59: 300; Suthanthiran and Strom (1994) New Engl. J. Med. 331:365). Accordingly, the antibodies, and antibody portions, of the invention, can be used to inhibit transplant rejection using multiple-variable dose treatment, including rejections of allografts and xenografts and to inhibit GVHD. Although the antibody or antibody portion may be used alone, more preferably it is used in combination with one or more other agents that inhibit the immune response against the allograft or inhibit GVHD. For example, in one embodiment, an antibody or antibody portion of the invention is used in combination with OKT3 to inhibit OKT3-induced reactions. In another embodiment, an antibody or antibody portion of the invention is used in combination with one or more antibodies directed at other targets involved in regulating immune responses, such as the cell surface molecules CD25 (interleukin-2 receptor-a), CD11a (LFA-1), CD54 (ICAM-1), CD4, CD45, CD28/CTLA4, CD80 (B7-1) and/or CD86 (B7-2). In yet another embodiment, an antibody or antibody portion of the invention is used in combination with one or more general immunosuppressive agents, such as cyclosporin A or FK506.

E. Malignancy

The methods of the invention may be used to treat subjects having cancer or a malignant tumor. Tumor necrosis factor has been implicated in inducing cachexia, stimulating tumor growth, enhancing metastatic potential and mediating cytotoxicity in malignancies. Accordingly, antibodies, and antibody portions, which directed against TNF, can be used in the multiple-variable dose treatment of malignancies, wherein treatment inhibits tumor growth or metastasis and/or alleviates cachexia secondary to malignancy. The antibody, or antibody portion, may be administered systemically or locally to the tumor site.

F. Pulmonary Disorders

The methods of the invention may be used to treat subjects having a pulmonary disease. Tumor necrosis factor has been implicated in the pathophysiology of adult respiratory distress syndrome (ARDS), including stimulating leukocyte-endothelial activation, directing cytotoxicity to pneumocytes and inducing vascular leakage syndrome. The multiple-variable dose methods of the invention can be used to treat various pulmonary disorders, including adult respiratory distress syndrome, using multiple-variable dose treatment (see e. g., PCT Publication No. WO 91/04054), shock lung, chronic pulmonary inflammatory disease, pulmonary sarcoidosis, pulmonary fibrosis and silicosis. The antibody, or antibody portion, may be administered systemically or locally to the lung surface, for example as an aerosol. An antibody, or antibody portion, also can be administered with one or more additional therapeutic agents useful in the multiple-variable dose treatment of pulmonary disorders, as discussed further in subsection IV.

Other examples of pulmonary disorders in which TNFα has been implicated in the pathophysiology include idiopathic interstitial lung disease and chronic obstructive airway disorders (see e. g., Piquet et al. (1989) J Exp Med. 170: 655; Whyte et al. (2000) Am J Respir Crit Care Med. 162: 755; Anticevich et al. (1995) Eur J Pharmacol. 284: 221). The invention further provides methods for treating TNFα activity in a subject suffering from such a pulmonary disorder, which method comprises administering to the subject an antibody, antibody portion, or other TNFα inhibitor using a multiple variable dose regimen such that TNFα activity in the subject suffering from idiopathic interstitial lung disease or a chronic obstructive airway disorder is inhibited. Examples of idiopathic interstitial lung diseases and chronic obstructive airway disorders in which TNFα activity is detrimental are discussed further below.

1. Idiopathic Interstitial Lung Disease

In one embodiment, the TNFα antibody of the invention is used in multiplevariable dose treatment regimen to treat subjects who have an idiopathic interstitial lung disease. The term "idiopathic pulmonary fibrosis" or "IPF" refers to a group of disorders characterized by inflammation and eventually scarring of the deep lung tissues, leading to shortness of breath. The scarring of the alveoli (air sacs) and their supporting structures (the interstitium) in IPF eventually leads to a loss of the functional alveolar units and a reduction of the transfer of oxygen from air to blood. IPF is also referred to as diffuse parenchymal lung disease; alveolitis; cryptogenic fibrosing alveolitis (CFA); idiopathic pulmonary pneumonitis (IPP); and usual interstitial pneumonitis (UIP). IPF is often used synonymously with UIP ("IPF/UIP") because UIP is the most common cellular pattern seen in the pathologic diagnosis of IPF.

Idiopathic interstitial lung diseases affect the lungs in three ways: first, the lung tissue is damaged in some known or unknown way; second, the walls of the air sacs in the lung become inflamed; and finally, scarring (or fibrosis) begins in the interstitium (or tissue between the air sacs), and the lung becomes stiff. Examples of idiopathic interstitial lung diseases include idiopathic pulmonary fibrosis (IPF). Tumor necrosis factor has been implicated in the pathophysiology of idiopathic pulmonary fibrosis (IPF) (see Piquet et al. (1989) J Exp Med. 170: 655; Whyte et al. (2000) Am J Respir Crit Care. Med 162: 755 Corbett et al. (2002) Am J Respir Crit Care Med. 165: 690). For example, it has been found that IPF patients have increased levels of TNF expressiojn in macrophages and in type II epithelial cells (Piquet et al. (1993) Am J Pathol 143:651; Nash et al. (1993) Histopathology 22: 343; Zhang et al. (1993) J Immunol 150: 4188).

Certain genetic polymorphisms are also associated with increased TNF expression, and are implicated in playing a role in IPF and silicosis (Whyte et al., supra; Corbett et al., supra)-Patients with IPF often exhibit certain symptoms, including a dry cough, chest pain, and/or shortness of breath. Commonly used drugs for the treatment of IPF are prednisone and cytoxan, although only a fraction of patients improve with continued use of these drugs (American Thoracic Society (2000) Am. J. Respir. Crit. Care Med. 161: 646). Oxygen administration and transplantation of the lung are other choices for treatment. In one embodiment, antibodies used in the multiple-variable dose methods of the invention may be used in combination with another therapeutic agent, for example oxygen, for the treatment of idiopathic pulmonary fibrosis.

Examples of animal models used to study idiopathic interstitial lung disease and chronic obstructive airway disorders include ovalbumin (OVA) induced allergic asthma mice and cigarette smoke induced chronic obstructive pulmonary disease mice (see Hessel et al. (1995) Eur J Pharmacol. 293: 401; Keast et al. (1981) J. Pathol. 135:249).

2. Chronic Obstructive Airway Disorder

In one embodiment, a TNFα antibody is used in multiple-variable dose treatment regimen to treat a subject who has a chronic obstructive airflow disorder. In these diseases, airflow obstruction may be chronic and persistent or episodic and recurrent.

Airflow obstruction is usually determined by forced expiratory spirometry, which is the recording of exhaled volume against time during a maximal expiration. In a subject who does not have an obstructed airflow, a full forced expiration usually takes between 3 and 4 seconds. In a patient with chronic obstructive airflow disorder, wherein airflow is obstructed, it usually takes up to 15 to 20 seconds and may be limited by breath-holding time. The normal forced expiratory volume in the first second of expiration (FEV I) is easily measured and accurately predicted on the basis of age, sex, and height. The ratio of FEV1 to forced vital capacity (FEVI/FVC) normally exceeds 0.75. Recording airflow against volume during forced expiration and a subsequent forced inspiration—the flow-volume loop—is also useful, mainly for distinguishing upper from lower airway narrowing.

Examples of chronic obstructive airway disorders are described below.

a. Asthma

The methods of the invention may be used to treat subjects having asthma. Tumor necrosis factor has been implicated in the pathophysiology of asthma, (Anticevich et al. (1995) Eur J Pharmacol. 284: 221; Thomas et al. 1995. Am J Respir Crit Care Med. 152:76; Thomas and Heywood (2002) Thorax. 57: 774). For example, acute asthma attacks have been found to be associated with pulmonary neutrophilia and elevated BAL TNF levels (Ordonez et al. (2000) Am J Respir Crit Care Med 161:1185).

It has been found that the severity of asthma symptoms correlates with endotoxin levels in house dust. In rats, anti-TNF antibodies reduced endotoxin-induced airway changes (Kips et al. (1992) Am Rev Respir Dis 145:332).

The term "asthma" as used herein, refers to a disorder in which inflammation of the airways causes airflow into and out of the lungs to be restricted. Asthma is also referred to as bronchial asthma, exercise induced asthma—bronchial, and reactive airways disease (RAD). In some instances, asthma is associated with allergies and/or is familial. Asthma includes a condition which is characterized by widespread fluctuations in the diameter or caliber of bronchial airways over short periods of time, resulting in changes in lung function. The resulting increased resistance to air flow produces symptoms in the affected subject, including breathlessness (dyspnea), chest constriction or "tightness" and wheezing.

Patients with asthma are characterized according to NIH guidelines, are described as mild intermittent, mild persistent, moderate persistent, and severe persistent (see NAEPP Expert Panel Report Guidelines for the Diagnosis and Management of Asthma-Update on Selected Topics 2002. JACI 2002; 110: S141-S209; Guidelines for the Diagnosis and Management of Asthma. NIH Publication 97-4051, July 1997). Patients diagnosed with moderate persistent asthma are often treated with inhaled corticosteroids.

Patients diagnosed with severe persistent asthma are often treated with high dose inhaled corticosteroids and p. o. corticosteroids. b. Chronic obstructive pulmonary disease (COPD) Tumor necrosis factor has been implicated in the pathophysiology of chronic obstructive pulmonary disease, (Keatings (2000) Chest. 118:971; Sakao et al. (2001) Am J Respir Crit Care Med. 163: 420; Sakao et al. (2002) Chest. 122: 416). The term "chronic obstructive pulmonary disease" or "COPD" as used interchangeably herein, refers to a group of lung diseases characterized by limited airflow with variable degrees of air sack enlargement and lung tissue destruction. The term COPD includes chronic bronchitis (mucous hypersecretion with goblet cell submucosal gland hyperplasia), chronic obstructive bronchitis, or emphysema (destruction of airway parenchyma), or combinations of these conditions. Emphysema and chronic bronchitis are the most common forms of chronic obstructive pulmonary disease. COPD is defined by irreversible airflow obstruction.

In COPD, chronic inflammation leads to fixed narrowing of small airways and lung parenchyma and alveolar wall destruction (emphysema). This is characterized by increased numbers of alveolar macrophages, neutrophils, and cytotoxic T lymphocytes, and the release of multiple inflammatory mediators (lipids, chemokines, cytokines, growth factors). This inflammation leads to fibrosis with a narrowing of the small airways and lung parenchymal destruction. There is also a high level of oxidative stress, which may amplify this inflammation.

G. Intestinal Disorders

The methods of the invention may be used to treat subjects having an intestinal disorder. Tumor necrosis factor has been implicated in the pathophysiology of inflammatory bowel disorders including Crohn's disease (see e. g., Tracy et al. (1986) Science 234:470; Sun et al. (1988) J Clin. Invest. 81:1328; MacDonald et al. (1990) Clin. Exp. Immunol. 81:301). Chimeric murine anti-hTNFα antibodies have undergone clinical testing for treatment of Crohn's disease (van Dullemen et al. (1995) Gastroenterology 109: 129). WO2005110452 teaches the treatment of intestinal disorders with adalimumab. The present invention includes a multiple-variable dose regimen comprising administering a TNFα inhibitor to treat intestinal disorders, such as idiopathic inflammatory bowel disease, using human antibodies, or antigen-binding fragments thereof.

Idiopathic inflammatory bowel disease includes two syndromes, Crohn's disease and ulcerative colitis. In one embodiment, the multiple-variable dose regimen of the invention is also used to treat disorders often associated with IBD and Crohn's disease. The term "inflammatory bowel disorder (IBD)-related disorder" or "Crohn's disease-related disorder," as used interchangeably herein, is used to describe conditions and complications commonly associated with IBD and Crohn's disease.

The invention includes a multiple-variable dose regimen comprising administering a TNFα inhibitor to treat Crohn's disease, in particular to cause mucosal healing in a subject having Crohn's disease. The treatment of Crohn's disease is based on location, extent, and severity of disease. Pharmacologic interventions include anti-inflammatory agents (aminosalicylates and corticosteroids) and immunomodulatory agents (azathioprine and 6-mercaptopurine [6-MP], cyclosporine, methotrexate [MTX], antibiotic agents, and biologic agents). C-reactive protein (CRP) and erythrocyte sedimentation rate (ESR) levels reflect non-specific acute phase reactions. Endoscopy is a primary means of diagnosing Crohn's disease. Radiologic features of Crohn's disease are shown by barium examination includes mucosal edema, aphthous and linear ulcerations, asymmetrical narrowing and strictures, and separation of adjacent loops of bowel caused by mesenteric thickening. Abnormalities are focal and asymmetric. The primary histologic lesion is an aphthous ulcer. Subjects with Crohn's disease can be evaluated using the Crohn's Disease Activity Index (CDAI), which is a standard measure of the severity of the disease with higher scores indicating more severe disease activity.

Examples of Crohn's disease-related disorders which can be treated using the methods of the invention include fistulas in the bladder, vagina, and skin; bowel obstructions; abscesses; nutritional deficiencies; complications from corticosteroid use; inflammation of the joints; erythem nodosum; pyoderma gangrenosum; and lesions of the eye. Other disorders commonly associated with Crohn's disease include Crohn's related arthralgias, fistulizing Crohn's, indeterminate colitis, and pouchitis.

H. Cardiac Disorders

The multiple-variable dose methods of the invention also can be used to treat in of various cardiac or coronary disorders, including ischemia of the heart (see e.g., European Patent Application Publication No. EP 453 898) and heart insufficiency (weakness of the heart muscle)(see e. g., PCT Publication No. WO 94/20139). TNFα has also been implicated in the pathophysiology of restenosis (see e. g., Clausell et al. (1994), supra; Medall et al. (1997) Heart 78:273).

As used herein, the term "a cardiac disorder in which TNFα activity is detrimental" is intended to include coronary and cardiovascular diseases in which the presence of TNFα in a subject suffering from the disorder has been shown to be or is suspected of being either responsible for the pathophysiology of the disorder or a factor that contributes to a worsening of the disorder, including cardiovascular disorders, e.g., restenosis. The term "cardiovascular disorder" or "coronary disorder" as used interchangeably herein, refers to any disease, disorder, or state involving the cardiovascular system, e. g., the heart, the blood vessels, and/or the blood. A coronary disorder is generally characterized by a narrowing of the blood vessels that supply blood and oxygen to the heart (coronary arteries). Coronary disease may result from the build up of fatty material and plaque. As the coronary arteries narrow, the flow of blood to the heart can slow or stop. Coronary disorders of the invention can apply to any abnormality of an artery, whether structural, histological, biochemical or any other abnormality. An example of coronary heart disease is restenosis. In one embodiment, a coronary disorder refers to any disease, disorder, or state involving the cardiovascular system excluding ischemia of the heart and heart insufficiency.

Coronary disorders in which TNFα activity is detrimental often result from a blockage in an artery. Such a blockage can be caused by a clot, which usually forms in a coronary artery that has been previously narrowed from changes usually related to atherosclerosis. For example, if the atherosclerotic plaque inside the arterial wall cracks, it can trigger the formation of a thrombus, or clot. Such disorders may be evidenced, for example, by an increase in the concentration of TNFα in a biological fluid of a subject suffering from the disorder (e. g., an increase in the concentration of TNFα in serum, plasma, synovial fluid, etc. of the subject), which can be detected, for example, using an anti-TNFα antibody as described above. A coronary disorder can be also caused by an imbalance in arterial pressure, a malfunction of the heart, or an occlusion of a blood vessel, e. g., by a thrombus. Coronary disorders includes both coronary artery disease and peripheral vascular disease.

There are numerous examples of cardiac disorders in which TNFα activity is detrimental, including restenosis. The use of the antibodies, antibody portions, and other TNFα inhibitors in multiple-variable dose regimens for treatment of specific coronary disorders is discussed further below. In certain embodiments, a antibody, antibody portion, or other TNFα inhibitor is administered to the subject in combination with another therapeutic agent, as described below.

The invention provides a multiple-variable dose method for inhibiting TNFα activity in a subject with a cardiac disorder. The invention provides multiple-variable dose methods for inhibiting or decreasing TNFα activity in a subject with a coronary disorder, comprising administering to the subject an antibody, or antibody portion, or other TNFα inhibitor of the invention such that TNFα activity in the subject is inhibited or decreased. Preferably, the TNFα is human TNFα and the subject is a human subject.

Alternatively, the subject can be a mammal expressing a TNFα with which an antibody of the invention cross-reacts. Still further the subject can be a mammal into which has been introduced hTNFα (e. g., by administration of hTNFα or by expression of an hTNFα transgene). An antibody of the invention can be administered to a human subject for therapeutic purposes.

Moreover, an antibody of the invention can be administered to a non-human mammal expressing a TNFα with which the antibody cross-reacts (e. g., a primate, pig or mouse) for veterinary purposes or as an animal model of human disease. Regarding the latter, such animal models may be useful for evaluating the multiple-variable dose therapeutic efficacy (e. g., testing of dosages and time courses of administration).

Commonly used animal models for studying coronary disorders, including restenosis, include the rat or mouse carotid artery ligation model and the carotid artery injury model (Ferns et al. (1991) Science 253: 1129; Clowes et al. (1983) Lab. Invest. 49: 208; Lindner et al. (1993) Circ Res. 73:792). In the carotid artery ligation model, arterial blood flow is disrupted by ligation of the vessel near the distal bifurnation. As described in Clowes et al., the carotid artery injury model is performed such that the common carotid artery is denuded of endothelium by the intraluminal passage of a balloon catheter introduced through the external carotid artery. At 2 weeks, the carotid artery is markedly narrowed due to smooth muscle cell constriction, but between 2 and 12 weeks the intimal doubles in thickness leading to a decrease in luminal size. Any of these models can be used to determine the potential therapeutic action of the TNFα antibodies of the invention in the prevention and treatment of restenosis in humans.

The invention includes multiple-variable dose regimen for treatment of cardiovascular disorders in which TNFα activity is detrimental, wherein inhibition of TNFα activity is expected to alleviate the symptoms and/or progression of the coronary disease or to prevent the coronary disease. Subjects suffering from or at risk of developing coronary disorders can be identified through clinical symptoms. Clinical symptoms in coronary disease often include chest pain, shortness of breath, weakness, fainting spells, alterations in consciousness, extremity pain, paroxysmal nocturnal dyspnea, transient ischemic attacks and other such phenomena experienced by the patient. Clinical signs of coronary disease can also include EKG abnormalities, altered peripheral pulses, arterial bruits, abnormal heart sounds, rates and wheezes, jugular venous distention, neurological alterations and other such findings discerned by the clinician. Coronary disorders may also be evidenced, for example, by an increase in the concentration of TNFα in a biological fluid of a subject suffering from the disorder (e.g., an increase in the concentration of TNFα in serum, plasma, synovial fluid, etc. of the subject).

Examples of a cardiovascular disorder include, but are not limited to, coronary artery disease, angina pectoris, myocardial infarction, cardiovascular tissue damage caused by cardiac arrest, cardiovascular tissue damage caused by cardiac bypass, cardiogenic shock, and hypertension, atherosclerosis, coronary artery spasm, coronary artery disease, valvular disease, arrhythmias, and cardiomyopathies. The use of the antibodies, antibody portions, and other TNFα inhibitors in multiple-variable dose regimens for treatment of specific cardiovascular-diseases are discussed further below.

In certain embodiments, the antibody, antibody portion, or other TNFα inhibitor is administered to the subject in combination with another therapeutic agent, as described below in.

1. Restenosis

The methods of the invention may be used to treat subjects having restenosis. The term "restenosis" as used herein refers to the recurrence of stenosis, which is the narrowing or constriction of an artery. Restenosis often occurs as a preocclusive lesion that develops following a reconstructive procedure in a diseased blood vessel.

The term is not only applied to the recurrence of a pre-existing stenosis, but also to previously normal vessels that become partially occluded following vascular bypass. In another embodiment, the invention provides a method of treating restenosis comprising administering the antibody, or antigen binding portion thereof, of the invention to a subject who has or is at risk of developing restenosis.

TNFα has been implicated in the pathophysiology of restenosis (see Zhou et al. (2002) Atherosclerosis. 161:153; Javed et al. (2002) Exp and Mol Pathol 73:104). For example, in the murine wire carotid model, TNF−/−mice demonstrated a seven-fold reduction in initial hyperplasia compared to wild type mice (Zimmerman et al. (2002) Am J Phsiol Regul Integr Comp Physiol 283:R505). Restenosis can occur as the result of any type of vascular reconstruction, whether in the coronary vasculature or in the periphery (Colburn and Moore (1998) Myointimal Hyperplasia pp. 690-709 in Vascular Surgery: A Comprehensive Review Philadelphia: Saunders). For example, studies have reported symptomatic restenosis rates of 30-50% following coronary angioplasties (see Berk and Harris (1995) Adv. Intern. Med. 40: 455). After carotid endarterectomies, as a further example, 20% of patients studied had a luminal narrowing greater than 50% (Clagett et al. (1986) J. Vasc. Surg. 3:10). Restenosis is evidenced in different degrees of symptomatology which accompany preocclusive lesions in different anatomical locations, due to a combination of factors including the nature of the vessels involved, the extent of residual disease, and local hemodynamics.

"Stenosis" as used herein refers to a narrowing of an artery as seen in occlusive disorder or in restenosis. Stenosis can be accompanied by those symptoms reflecting a decrease in blood flow past the narrowed arterial segment, in which case the disorder giving rise to the stenosis is termed a disease (i. e., occlusive disease or restenosis disease). Stenosis can exist asymptomatically in a vessel, to be detected only by a diagnostic intervention such as an angiography or a vascular lab study.

The multiple-variable dose method of the invention can be used to treat a subject suffering from or at risk of developing restenosis. A subject at risk of developing restenosis includes a subject who has undergone PTCA. The subject may have also had a stent inserted to prevent restenosis. The TNFα antibody can be used alone or in combination with a stent to prevent the re-occurrence of stenosis in a subject suffering from cardiovascular disease.

2. Congestive Heart Failure

The methods of the invention may be used to treat subjects having congestive heart failure. TNFα has been implicated in the pathophysiology of congestive heart failure (see Zhou et al. (2002) Atherosclerosis 161: 153). Serum levels of TNFα are elevated in patients with congestive heart failure in a manner which is directly proportional to the severity of the disease (Levine et al. (1990) N Engl J Med 323: 236; Torre-Amione et al. (1996) J Am Coil Cardiol 27:1201). In addition, inhibitors of TNFα have also been shown to improve congestive heart failure symptoms (Chung et al. (2003) Circulation 107: 3133).

As used herein, the term "congestive heart failure" includes a condition characterized by a diminished capacity of the heart to supply the oxygen demands of the body. Symptoms and signs of congestive heart failure include diminished blood flow to the various tissues of the body, accumulation of excess blood in the various organs, e.g., when the heart is unable to pump out the blood returned to it by the great veins, exertional dyspnea, fatigue, and/or peripheral edema, e. g., peripheral edema resulting from left ventricular dysfunction.

Congestive heart failure may be acute or chronic. The manifestation of congestive heart failure usually occurs secondary to a variety of cardiac or systemic disorders that share a temporal or permanent loss of cardiac function.

Examples of such disorders include hypertension, coronary artery disease, valvular disease, and cardiomyopathies, e.g., hypertrophic, dilative, or restrictive cardiomyopathies.

A "subject who has or is suffering from congestive heart failure" is a subject who has a disorder involving a clinical syndrome of diverse etiologies linked by the common denominator of impaired heart pumping in which the heart cannot pump blood commensurate with the requirements of the metabolizing tissues, or can do so only from an elevated filling pressure. A "subject at risk of developing congestive heart failure" is a subject who has a propensity of developing congestive heart failure because of certain factors affecting the cardiovascular system of the subject. It is desirable to reduce the risk of or prevent the development of congestive heart failure in these subjects. The phrase "with congestive heart failure" includes patients who are at risk of suffering from this condition relative to the general population, even though they may not have suffered from it yet, by virtue of exhibiting risk factors. For example, a patient with untreated hypertension may not have suffered from congestive heart failure, but is at risk because of his or her hypertensive condition. In one embodiment of the invention, the antibody D2E7 is used to treat a subject at risk of developing congestive heart failure using multiple-variable dose treatment.

3. Acute Coronary Syndromes

The methods of the invention may be used to treat subjects having an acute coronary syndromes. TNFα has been implicated in the pathophysiology of acute coronary syndromes (see Libby (1995) Circulation 91:2844). Acute coronary syndromes include those disorders wherein the subject experiences pain due to a blood flow restriction resulting in not enough oxygen reaching the heart. Studies have found that TNFα plays a role in acute coronary syndromes. For example, in a novel rat heterotropic cardiac transplantation-coronary ligation model capable of inducing myocardial infarction in the absence of downstream hemodynamic effects, administration of chimeric soluble TNF receptor (sTNFR) abolished transient LV remodeling and dysfunction (Nakamura, et al. (2003) J Cardiol. 41:41). It was also found that direct injection of an sTNFR expression plasmid to the myocardium, resulted in a reduction in the infarction size in acute myocardial infarction (AMI) experimental rats (Sugano et al. (2002) FASEB J 16: 1421).

In one embodiment, a TNFα antibody is used in a multiple-variable dose method for the treatment or prevention of an acute coronary syndrome in a subject, wherein the acute coronary syndrome is a myocardial infarction or angina.

As used herein, the term "myocardial infarction" or "MI" refers to a heart attack.

A myocardial infarction involves the necorsis or permanent damage of a region of the heart due to an inadequate supply of oxygen to that area. This necrosis is typically caused by an obstruction in a coronary artery from either atherosclerosis or an embolis.

MIs which are treated by the TNFα antibody of the invention include both Q-wave and non-Q-wave myocardial infarction. Most heart attacks are caused by a clot that blocks one of the coronary arteries (the blood vessels that bring blood and oxygen to the heart muscle). For example, a clot in the coronary artery interrupts the flow of blood and oxygen to the heart muscle, leading to the death of heart cells in that area. The damaged heart muscle permanently loses its ability to contract, and the remaining heart muscle needs to compensate for it. An MI can also be caused by overwhelming stress in the individual.

The term "angina" refers to spasmodic, choking, or suffocative pain, and especially as denoting angina pectoris which is a paroxysmal thoracic pain due, most often, to anoxia of the myocardium. Angina includes both variant angina and exertional angina. A subject having angina has ischemic heart disease which is manifested by sudden, severe, pressing substernal pain that often radiates to the left shoulder and along the left arm. TNFα has been implicated in angina, as TNFα levels are upregulated in patients with both MI and stable angina (Balbay et al. (2001) Angiology 52109).

4. Artherosclerosis

The methods of the invention may be used to treat subjects having atherosclerosis. "Atherosclerosis" as used herein refers to a condition in which fatty material is deposited along the walls of arteries. This fatty material thickens, hardens, and may eventually block the arteries. Atherosclerosis is also referred to arteriosclerosis, hardening of the arteries, and arterial plaque buildup. Polyclonal antibodies directed against TNFα have been shown to be effective at neutralizing TNFα activity resulting in inflammation and restenosis in the rabbit atherosclerotic model (Zhou et al., supra).

Accordingly, a TNFα antibody can be used to treat or prevent subjects afflicted with or at risk of having atherosclerosis using the multiple-variable dose method of the invention.

5. Cardiomyopathy

The methods of the invention may be used to treat subjects having a cardiomyopath. The term "cardiomyopathy" as used herein is used to define diseases of the myocardium wherein the heart muscle or myocardium is weakened, usually resulting in inadequate heart pumping. Cardiomyopathy can be caused by viral infections, heart attacks, alcoholism, long-term, severe hypertension (high blood pressure), or by autoimmune causes.

In approximately 75-80% of heart failure patients coronary artery disease is the underlying cause of the cardiomyopathy and is designated "ischemic cardiomyopathy." Ischemic cardiomyopathy is caused by heart attacks, which leave scars in the heart muscle or myocardium. The affected myocardium is then unable to contribute to the heart pumping function. The larger the scars or the more numerous the heart attacks, the higher the chance there is of developing ischemic cardiomyopathy.

Cardiomyopathies that are not attributed to underlying coronary artery disease, and are designated "non-ischemic cardiomyopathies." Non-ischemic cardiomyopathies include, but are not limited to idiopathic cardiomyopathy, hypertrophic cardiomyopathy, alcoholic cardiomyopathy, dilated cardiomyopathy, peripartum cardiomyopathy, and restrictive cardiomyopathy.

I. Spondyloarthropathies

The methods of the invention may also be used to treat subjects who have a spondyloarthropathy. TNFα has been implicated in the pathophysiology of a wide variety of disorders, including inflammatory diseases such as spondyloarthopathies (see e.g., Moeller et al. (1990) Cytokine 2:162; U.S. Pat. No. 5,231,024; European Patent Publication No. 260 610). The invention provides multiple-variable dose methods for inhibiting TNFα activity in a subject suffering from a spondyloarthropathy, which method comprises administering to the subject an antibody, antibody portion, or other TNFα inhibitor initially in an induction dose, followed by a treatment dose, such that TNFα activity in the subject suffering from a spondyloarthropathy is inhibited.

As used herein, the term "spondyloarthropathy" or "spondyloarthropathies" is used to refer to any one of several diseases affecting the joints of the spine, wherein such diseases share common clinical, radiological, and histological features. A number of spondyloarthropathies share genetic characteristics, i. e. they are associated with the HLA-B27 allele. In one embodiment, the term spondyloarthropathy is used to refer to any one of several diseases affecting the joints of the spine, excluding ankylosing spondylitis, wherein such diseases share common clinical, radiological, and histological features. Examples of spondyloarthropathies include ankylosing spondylitis, psoriatic arthritis/spondylitis, enteropathic arthritis, reactive arthritis or Reiter's syndrome, and undifferentiated spondyloarthropathies. Examples of animal models used to study spondyloarthropathies include anklank transgenic mice, HLA-B27 transgenic rats (see Taurog et al. (1998) The Spondylarthritides. Oxford:Oxford University Press).

The multiple-variable dose methods of the invention can also be used to treat subjects who are at risk of developing a spondyloarthropathy using multiple-variable dose methods. Examples of subjects who are at risk of having spondyloarthropathies include humans suffering from arthritis. Spondyloarthropathies can be associated with other forms of arthritis, including rheumatoid arthritis. In one embodiment of the invention, antibodies are used in multiple-variable dose methods to treat a subject who suffers from a spondyloarthropathy associated with rheumatoid arthritis. Examples of spondyloarthropathies which can be treated with a TNFα antibody using the multiple-variable dose method of the invention are described below:

1. Ankylosing Spondylitis (AS)

The methods of the invention may be used to treat subjects having ankylosing spondylitis. Tumor necrosis factor has been implicated in the pathophysiology of ankylosing spondylitis (see Verjans et al. (1991) Arthritis Rheum. 34: 486; Verjans et al. (1994) Clin Exp Immunol. 97:45; Kaijtzel et al. (1999) Hum Immunol. 60:140). Ankylosing spondylitis (AS) is an inflammatory disorder involving inflammation of one or more vertebrae. AS is a chronic inflammatory disease that affects the axial skeleton and/or peripheral joints, including joints between the vertebrae of the spine and sacroiliac joints and the joints between the spine and the pelvis. AS can eventually cause the affected vertebrae to fuse or grow together. Spondyarthropathies, including AS, can be associated with psoriatic arthritis (PsA)

and/or inflammatory bowel disease (IBD), including ulcerative colitis and Crohn's disease.

Early manifestations of AS can be determined by radiographic tests, including CT scans and MRI scans. Early manifestations of AS often include scroiliitis and changes in the sacroliac joints as evidenced by the blurring of the cortical margins of the subchrondral bone, followed by erosions and sclerosis. Fatigue has also been noted as a common symptom of AS (Duffy et al. (2002) ACR 66th Annual Scientific Meeting Abstract). Accordingly, multiple-variable dose methods comprising administering an antibody, or antigen-binding fragment thereof, of the invention can be used to treat AS.

In one embodiment, the multiple-variable dose method of the invention is used to treat a spondyloarthropathy associated with IBD, including AS. AS is often treated with nonsteroidal anti-inflammatory medications (NSAIDs), such as aspirin or indomethacin.

Accordingly, a TNFα antibody used in the multiple-variable dose method of the invention may also be administered in combination with agents commonly used to reduce inflammation and pain commonly associated with ankylosing spondylitis.

2. Psoriatic Arthritis

The methods of the invention may also be used to treat subjects who have psoriatic arthritis. Tumor necrosis factor has been implicated in the pathophysiology of psoriatic arthritis (PsA) (Partsch et al. (1998) Ann Rheum Dis. 57:691; Ritchlin et al. (1998) J Rheumatol. 25:1544). As referred to herein, psoriatic arthritis or psoriasis associated with the skin, refers to chronic inflammatory arthritis which is associated with psoriasis, which is a common chronic skin condition that causes red patches on the body. 1 in 20 individuals with psoriasis will develop arthritis along with the skin condition, and in 75% of cases, psoriasis precedes the arthritis. PsA exhibits itself in a variety of ways, ranging from mild to severe arthritis, wherein the arthritis usually affects the fingers and the spine. When the spine is affected, the symptoms are similar to those of ankylosing spondylitis, as described above. The TNFα antibody, or antigen-binding fragment thereof, of the invention can be used in multiple-variable dose treatment of PsA.

PsA is sometimes associated with arthritis mutilans. Arthritis mutilans refers to a disorder which is characterized by excessive bone erosion resulting in a gross, erosive deformity which mutilates the joint. In one embodiment, the multiple-variable dose method of the invention can be used to treat arthritis mutilans.

3. Reactive Arthritis/Reiter's Syndrome

The methods of the invention may also be used to treat subjects who have Reactive arthritis/Reiter's syndrome. Tumor necrosis factor has been implicated in the pathophysiology of reactive arthritis, which is also referred to as Reiter's syndrome (Braun et al. (1999) Arthritis Rheum. 42 (10):2039). arthritis (ReA) refers to arthritis which complicates an infection elsewhere in the body, often following enteric or urogenital infections. ReA is often characterized by certain clinical symptoms, including inflammation of the joints (arthritis), urethritis, conjunctivitis, and lesions of the skin and mucous membranes. In addition, ReA can occurs following infection with a sexually transmitted disease or dysenteric infection, including *chlamydia, campylobacter, salmonella,* or *yersinia.*

Accordingly, the multiple-variable dose method of the invention can be used to treat ReA using the multiple-variable dose method of the invention.

4. Undifferentiated Spondyloarthropathies

In one embodiment, multiple-variable dose methods of the invention of the invention are used to treat subjects suffering from undifferentiated spondyloarthropathies (see Zeidler et al. (1992) Rheum Dis Clin North Am. 18:187). Other terms used to describe undifferentiated spondyloarthropathies include seronegative oligoarthritis and undifferentiated oligoarthritis. Undifferentiated spondyloarthropathies, as used herein, refers to a disorder wherein the subject demonstrates only some of the symptoms associated with a spondyloarthropathy. This condition is usually observed in young adults who do not have IBD, psoriasis, or the classic symptoms of AS or Reiter's syndrome. In some instances, undifferentiated spondyloarthropathies may be an early indication of AS. In one embodiment, the multiple-variable dose method of the invention comprises administering different doses of a TNFα antibody, or antigen binding fragment thereof, to treat undifferentiated spondyloarthropathies.

J. Metabolic Disorders

The formulations and methods of the invention may be used to treat a metabolic disease. TNFα has been implicated in the pathophysiology of a wide variety of disorders, including metabolic disorders, such as diabetes and obesity (Spiegelman and Hotamisligil (1993) Cell 73: 625; Chu et al. (2000) Int J Obes Relat Metab Disord. 24: 1085; Ishii et al. (2000) Metabolism. 49: 1616). The term "metabolic disorder," as used herein, refers to diseases or disorders which affect how the body processes substances needed to carry out physiological functions. Examples of metabolic disorders include, but are not limited to, diabetes and obesity. In one embodiment of the invention, the term "metabolic disorder" is used to refer to disorders which affect how the body processes substances needed to carry out physiological functions, excluding autoimmune diabetes.

The invention provides multiple-variable dose methods for inhibiting TNFα activity in a subject suffering from such a metabolic disorder, which method comprises administering to the subject an induction dose followed by a treatment dose of an antibody, antibody portion, or other TNFα inhibitor such that TNFα activity in the subject suffering from a metabolic disorder is inhibited. TNFα antibodies can also be used to treat subjects who are at risk of developing a metabolic disorder using the multiple-variable dose regimen of the invention.

Metabolic disorders are often associated with arthritis, including rheumatoid arthritis. In one embodiment, a TNFα inhibitor, such as an antibody, is used in a multiple-variable dose regimen in a subject who suffers from a metabolic disorder associated with rheumatoid arthritis. In another embodiment, the multiple-variable dose treatment of the invention comprises administering a TNFα antibody to treat disorders associated with diabetes or obesity.

Examples of animal models for evaluating the efficacy of a multiple-variable dose regimen using a TNFα antibody for the treatment of a metabolic disorder include NOD transgenic mice, Akita mice, NSY transgenic mice and oblob mice (see Baeder et al. (1992) Clin Exp Immunol. 89:174; Haseyama et al. (2002) Tohoku J Exp Med. 198: 233; Makino et al. (1980): Exp. Anim. 29:1; Kolb (1987) Diabetes/Metabolism Reviews 3:751; Hamada et al. (2001) Metabolism. 50: 1282; Coleman, (1978) Diabetologia, 14: 141; Bailey et al. (1982) Int. J. Obesity 6:11). Examples of animal models used to study vasculitis includes the mouse HSV model (Behcet's disease), the mouse *L. casei* model (Kawasaki's disease), and the mouse ANCA model (Kawasaki's disease). Other models of vasculitis include the McH5-Ipr/Ipr strain (Nose et al. (1996) Am. J. Path. 149: 1763) and the SCG/Kj strain of mice (Kinjoh et al. (1993)

Proc. Natl. Acad. Sci., USA 90: 3413). These mice strains spontaneously develop crescentic glomerulonephritis and necrotizing vasculitis of the small arteries and arterioles of the spleen, stomach, heart, uterus and ovaries. These animals develop hypergammaglobulinemia and ANCA autoantibodies that react with myeloperoxidase (MPO). Additionally, immunization of rats with human MPO results in ANCA-associated necrotizing crescentic glomerulonephritis (Brouwer et al. (1993) J. Exp. Med. 177: 905).

Metabolic disorders affect how the body processes substances needed to carry out physiological functions. A number of metabolic disorders of the invention share certain characteristics, i. e. they are associated the insulin resistance, lack of ability to regulate blood sugar, weight gain, and increase in body mass index. Examples of metabolic disorders include diabetes and obesity. Examples of diabetes include type 1 diabetes mellitus, type 2 diabetes mellitus, diabetic neuropathy, peripheral neuropathy, diabetic retinopathy, diabetic ulcerations, retinopathy ulcerations, diabetic macrovasculopathy, and obesity. Examples of metabolic disorders which can be treated using multiplevariable dose methods comprising administration of a TNFα antibody are described in more detail below:

1. Diabetes

The methods of the invention may be used to treat subjects having diabetes. Tumor necrosis factor has been implicated in the pathophysiology of diabetes. (see e. g., Navarro et al. (2003) Am J Kidney Dis. 42: 53; Daimon et al. (2003) Diabetes Care. 26: 2015; Zhang et al. (1999) J Tongji Med Univ. 19: 203; Barbieri et al. (2003) Am J Hypertens. 16: 537) For example, TNFα is implicated in the pathophysiology for insulin resistance. It has been found that serum TNF levels in patients with gastrointestinal cancer correlates with insulin resistance (see e.g., McCall et at. (1992) Br. J Surg. 79:1361).

The term "diabetes" or "diabetic disorder" or "diabetes mellitus" as used interchangeably herein, refers to a disease which is marked by elevated levels of sugar (glucose) in the blood. Diabetes can be caused by too little insulin (a chemical produced by the pancreas to regulate blood sugar), resistance to insulin, or both. Diabetes includes the two most common types of the disorder, namely type I diabetes and type II diabetes, which both result from the body's inability to regulate insulin. Insulin is a hormone released by the pancreas in response to increased levels of blood sugar (glucose) in the blood.

The term "type 1 diabetes" as used herein, refers to a chronic disease that occurs when the pancreas produces too little insulin to regulate blood sugar levels appropriately.

Type 1 diabetes is also referred to as insulin-dependent diabetes mellitus, IDMM, juvenile onset diabetes, and diabetes—type I. Type 1 diabetes represents is the result of a progressive autoimmune destruction of the pancreatic (3-cells with subsequent insulin deficiency.

The term "type 2 diabetes" refers to a chronic disease that occurs when the pancreas does not make enough insulin to keep blood glucose levels normal, often because the body does not respond well to the insulin. Type 2 diabetes is also referred to as noninsulin-dependent diabetes mellitus, NDDM, and diabetes—type II Diabetes is can be diagnosed by the administration of a glucose tolerance test.

Clinically, diabetes is often divided into several basic categories. Primary examples of these categories include, autoimmune diabetes mellitus, non-insulin-dependent diabetes mellitus (type 1 NDDM), insulin-dependant diabetes mellitus (type 2 IDDM), non-autoimmune diabetes mellitus, non-insulin-dependant diabetes mellitus (type 2 NIDDM), and maturity-onset diabetes of the young (MODY). A further category, often referred to as secondary, refers to diabetes brought by some identifiable condition which causes or allows a diabetic syndrome to develop. Examples of secondary categories include, diabetes caused by pancreatic disease, hormonal abnormalities, drug- or chemical-induced diabetes, diabetes caused by insulin receptor abnormalities, diabetes associated with genetic syndromes, and diabetes of other causes. (see e. g., Harrison's (1996) 14th ed., New York, McGraw-Hill).

Diabetes is often treated with diet, insulin dosages, and various medications described herein. Accordingly, a TNFα antibody may also be administered in combination with agents commonly used to treat metabolic disorders and pain commonly associated with diabetes in the multiple-variable dose method of the invention.

In addition, the phrase "disorders associated with diabetes" as used herein, refers to conditions and other diseases which are commonly associated with or related to diabetes. Example of disorders associated with diabetes include, for example, hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, coronary heart disease, hypertension, angina pectoris, myocardial infarction, stroke, skin and connective tissue disorders, foot ulcerations, metabolic acidosis, arthritis, and osteoporosis. In one embodiment the multiple-variable dose methods of the invention can be used to treat disorders associated with diabetes.

Diabetes manifests itself in the foregoing categories and can cause several complications that are discussed in the following sections. Accordingly, the antibody, or antigen-binding fragment thereof, of the invention can be used to treat diabetes. In one embodiment, a TNFα antibody, or antigen-binding fragment thereof, is used to treat diabetes associated with the above identified catagories using the multiple-variable dose method of the invention. In another embodiment, the invention includes multiplevariable dose regimens comprising administering a TNFα antibody to treat disorders associated with diabetes. Diabetes manifests itself in many complications and conditions associated with diabetes, including the following catagories: a. Diabetic Neuropathy and Peripheral NeuropathyTumor necrosis factor has been implicated in the pathophysiology of diabetic neuropathy and peripheral neuropathy. (See Benjafield et al. (2001) Diabetes Care. 24: 753; Qiang et al. (1998) Diabetologia. 41:1321; Pfeiffer et al. (1997) Horm Metab Res. 29: 111).

The term "neuropathy" also referred to as nerve damage-diabetic, as used herein, refers to a common complication of diabetes in which nerves are damaged as a result of hyperglycemia (high blood sugar levels). A variety of diabetic neuropathies are recognized, such as distal sensorimotror polyneuropathy, focal motor neuropathy, and autonomic neuropathy.

The term "peripheral neuropathy" also known as peripheral neuritis and diabetic neuropathy, as used herein, refers to the failure of the nerves to carry information to and from the brain and spinal cord. Peripheral neuropathy produces symptoms such as pain, loss of sensation, and the inability to control muscles. In some cases, the failure of nerves to control blood vessels, intestinal function, and other organs results in abnormal blood pressure, digestion, and loss of other basic involuntary processes. Peripheral neuropathy may involve damage to a single nerve or nerve group (mononeuropathy) or may affect multiple nerves (polyneuropathy).

Neuropathies that affect small myelinated and umnyelinated fibers of the sympathetic and parasympathetic nerves are known as "peripheral neuropathies." Furthermore, the related disorder of peripheral neuropathy, also known as peripheral neuritis and diabetic neuropathy, refers to the failure of the nerves to carry information to and from the brain and spinal cord. This produces symptoms such as pain, loss of sensation, and the inability to control muscles. In some cases, failure of nerves controlling blood vessels, intestinal function, and other organs results in abnormal blood pressure, digestion, and loss of other basic involuntary processes. Peripheral neuropathy may involve damage to a single nerve or nerve group (mononeuropathy) or may affect multiple nerves (polyneuropathy).

The term "diabetic neuropathy" refers to a common complication of diabetes in which nerves are damaged as a result of hyperglycemia (high blood sugar levels).

Diabetic neuropathy is also referred to as neuropathy and nerve damage-diabetic. A variety of diabetic neuropathies are recognized, such as distal sensorimotror polyneuropathy, focal motor neuropathy, and autonomic neuropathy. b. Diabetic Retinopathy Tumor necrosis factor has been implicated in the pathophysiology of diabetic retinopthy (Scholz et al. (2003) Trends Microbiol. 11: 171). The term "diabetic retinopathy" as used herein, refers to progressive damage to the eye's retina caused by long-term diabetes. Diabetic retinopathy, includes proliferative retinopathy.

Proliferative neuropathy in turn includes includes neovascularization, pertinal hemmorrhave and retinal detachement.

In advanced retinopathy, small vessels proliferate on the surface of the retina.

These blood vessels are fragile, tend to bleed and can cause peretinal hemorrhages. The hemorrhage can obscure vision, and as the hemorrhage is resorbed fibrous tissue forms predisposing to retinal detachments and loss of vision. In addition, diabetic retinopathy includes prolferative retinopathy which includes neovascularization, pertinal hemmorrhave and retinal detachement. Daibetic retinopathy also includes "background retinopathy" which involves changes occuring with the layers of the retina. c. Diabetic Ulcerations and Retinopathy Ulcerations. Tumor necrosis factor has been implicated in the pathophysiology of diabetic ulcerations, (see Lee et al. (2003) Hum Immunol. 64: 614; Navarro et al. (2003) Am J Kidney Dis. 42: 53; Daimon et al (2003) Diabetes Care. 26: 2015; Zhang et al. (1999) J Tongji Med Univ. 19: 203; Barbieri et al. (2003) Am J Hypertens. 16: 537; Venn et al. (1993) Arthritis Rheum. 36:819; Westacott et al. (1994) J Rheumatol. 21:1710).

The term "diabetic ulcerations" as used herein, refers to an ulcer which results as a complication of diabetes. An ulcer is a crater-like lesion on the skin or mucous membrane caused by an inflammatory, infectious, malignant condition, or metabolic disorder. Typically diabetic ulcers can be found on limbs and extremeties, more typically the feet. These ulcers, caused by diabetic conditions, such as neuropathy and a vacualr insuffciency, can lead to ischemia and poor wound healing. More extensive ulcerations may progress to ostemyelitis. Once ostemyelitis develops, it may be dificult to eradicate with antibotics alone and amputation maybe necessary.

The term "retinopathy ulcerations" as used herein refers to an ulcer which causes or results in damages to the eye and the eye's retina. Retinopathy ulcerations may include conditions such has retinoathic hemmorages.

d. Diabetic Macrovasculopathy

The methods of the invention may be used to treat subjects having diabetic macrovasculopathy. Tumor necrosis factor has been implicated in the pathophysiology of diabetic macrovasculopathy (Devaraj et al. (2000) Circulation. 102: 191; Hattori et al. (2000) Cardiovasc Res. 46:188; Clausell et al. (1999) Cardiovasc Pathol. 8:145). The term "diabetic macrovasculopathy" also referred to as "macrovascular disease," as used herein, refers to a disease of the blood vessels that results from diabetes. Diabetic macrovasculopathy complication occurs when, for example, fat and blood clots build up in the large blood vessels and stick to the vessel walls. Diabetic macrovasculopathies include diseases such as coronary disease, cerebrovascular disease, and peripheral vascular disease, hyperglycaemia and cardiovascular disease, and strokes.

2. Obesity

The methods of the invention may be used to treat subjects suffering from obesity. Tumor necrosis factor has been implicated in the pathophysiology of obesity (see e. g., Pihlajamaki J et al. (2003) Obes Res. 11:912; Barbieri et al. (2003) Am J Hypertens. 16: 537; Tsuda et al. (2003) J Nutr. 133: 2125). The term "obesity" as used herein, refers to a condition in which the subject has an excess of body fat relative to lean body mass. In one embodiment, obesity refers to a condition in which an individual weighs at least 20% or more over the maximum desirable for their height. When an adult is more than 100 pounds overweight, he or she is considered to be "morbidly obese" In another embodiment, obesity is defined as a BMI (body mass index) over 30 kg/m2. Obesity increases a person's risk of illness and death due to diabetes, stroke, coronary artery disease, hypertension, high cholesterol, and kidney and gallbladder disorders. Obesity may also increase the risk for some types of cancer, and may be a risk factor for the development of osteoarthritis and sleep apnea. Obesity can be treated using the multiple-variable dose methods of the invention.

K. Anemia

The methods of the invention may be used to treat subjects having an anemia. TNFα has been implicated in the pathophysiology of a wide variety of anemias (see e.g., Jongen-Lavrencic et al. (1997) J. Rheumatol. 24:1504; Demeter et al. (2002) Ann Hematol. 81: 566; DiCato (2003) The Oncologist 8 (suppl 1):19). The invention provides multiple-variable dose methods for inhibiting TNFα activity in a subject suffering from anemia, which method comprises administering to the subject an induction dose followed by a treatment dose of a TNFα inhibitor, wherein the TNFα inhibitor is an antibody, antibody portion, such that TNFα activity in the subject suffering from anemia is inhibited. In one embodiment, the anemia is associated with rheumatoid arthritis.

The term "anemia" as used herein, refers to an abnormally low number of circulating red cells or a decreased concentration of hemoglobin in the blood. Examples of anemia related to rheumatoid arthritis include, for example, anemia of chronic disease, iron deficiency anemia, and autoimmune hemolytic anemia. In one embodiment, the invention provides a method of treating anemias related to, for example, anemias related to rheumatoid arthritis, anemias of infection and chronic inflammatory diseases, iron deficiency anemia, autoimmune hemolytic anemia, myelophthisic anemia, aplastic anemia, hypoplastic anemia, pure red cell aplasia and anemia associated with renal failure or endocrine disorders, megaloblastic anemias, defects in heme or globin synthesis, anemia caused by a structural defect in red bloodcells, e. g., sickle-cell anemia, and anemias of unknown origins such as sideroblasticanemia, anemia associated with chronic infections such as malaria, trypanosomiasis, HIV, hepatitis virus or other viruses, and myelophthisic anemias caused by marrow deficiencies.

Examples of animal models used to study anemia include rats inoculated with peptidolglycan-polysaccharide polymers (see Coccia et al., (2001) Exp Hematology. 29: 1201-1209). Examples of animal models used to study pain are well known in the art, and include the rat sciatic nerve ligation model, and the rat segmental spinal nerve ligation model (see Bennett and Zie, (1988) Pain. 33:87-107; Kim and Chung, (1992) Pain 50:355-363).

L. Pain

The methods of the invention may be used to treat subjects having a pain diorder. TNFα has been implicated in the pathophysiology of a wide variety of pain syndromes (see e.g., Sorkin et al. (1997) Neuroscience. 81:255; Huygen et al. (2002) Mediators Inflamm.—11: 47; Parada et al. (2003) Eur J Neurosci. 17:1847). The term"pain" as used herein, refers to all types of pain. The term shall refer to acute and chronic pains, such as neuropathic pain and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis. The term also includes nociceptive pain or nociception.

The invention provides multiple-variable dose methods for inhibiting TNFα activity in a subject suffering from such a pain disorder, which method comprises administering to the subject an induction dose followed by a treatment dose of an antibody, antibody portion, or other TNFα inhibitor such that TNFα activity in the subject suffering from pain is inhibited. Pain has been defined in a variety of ways, including nociceptive pain and neuropathic pain. The most commonly experienced form of pain may be defined as the effect of a stimulus on nerve endings, which results in the transmission of impulses to the cerebrum. Pain is also commonly associated with inflammatory disorders, including, for example, rheumatoid arthritis. In one embodiment, the antibody of the invention is used to treat a subject who suffers from pain associated with rheumatoid arthritis. Examples of pain disorders in which TNFα activity is detrimental are discussed further below.

1. Neuropathic Pain

The methods of the invention may be used to treat neuropathic pain. Tumor necrosis factor has been implicated in the pathophysiology of neuropathic pain (see Sommer (1999) Schmerz. 13: 315; Empl et al., (2001) Neurology. 56:1371; Schafers et al. (2003) J Neurosci. 23: 3028). As used herein the term "neuropathic pain" refers to pain that results from injury to a nerve, spinal cord, or brain, and often involves neural supersensitivity. Examples of neuropathic pain include chronic lower back pain, pain associated with arthritis, cancer-associated pain, herpes neuralgia, phantom limb pain, central pain, opioid resistant neuropathic pain, bone injury pain, and pain during labor and delivery. Other examples of neuropathic pain include post-operative pain, cluster headaches, dental pain, surgical pain, pain resulting from severe, for example third degree, burns, post partum pain, angina pain, genitourinary tract related pain, and including cystitis.

Neuropathic pain is distinguished from nociceptive pain. Pain involving a nociceptive mechanism usually is limited in duration to the period of tissue repair and generally is alleviated by available analgesic agents or opioids (Myers (1995) Regional Anesthesia 20:173). Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Unlike nociceptive pain, neuropathic pain generally is resistant to opioid therapy (Myers, supra, 1995). Accordingly, the multiple-variable dose methods of the invention can be used to treat neuropathic pain.

2. Nociceptive Pain

The methods of the invention may be used to treat nociceptive pain. As used herein the term "nociceptive pain" refers to pain that is transmitted across intact neuronal pathways, i. e., pain caused by injury to the body. Nociceptive pain includes somatic sensation and normal function of pain, and informs the subject of impending tissue damage. The nociceptive pathway exists for protection of the subject, e. g., the pain experienced in response to a bum). Nociceptive pain includes bone pain, visceral pain, and pain associated with soft tissue.

Tumor necrosis factor has been implicated in the pathophysiology of visceral pain (see Coelho et al. (2000) Am J Physiol Gastrointest Liver Physiol. 279:G781; Coelho et al. (2000) Brain Res Bull. 52: 223). Visceral pain is used to refer to nociceptive pain that is mediated by receptors on A-delta and C nerve fibers. A-delta and C-nerve fibers are which are located in skin, bone, connective tissue, muscle and viscera. Visceral pain can be vague in distribution, spasmodic in nature and is usually described as deep, aching, squeezing and colicky in nature. Examples of visceral pain include pain associated with a heart attack, wherein the visceral pain can be felt in the arm, neck and/or back, and liver capsule pain, wherein the visceral pain can be felt in the back and/or right shoulder. Accordingly, the multiple-variable dose methods of the invention can be used to treat visceral pain.

M. Hepatic Disorders

The methods of the invention may be used to treat subjects having a hepatic disorder. TNFα has been implicated in the pathophysiology of a wide variety of hepatic disorders (see e. g., Colletti et al. (1990) J Clin Invest. 85:1936; Tiegs (1997) Acta Gastroenterol Belg. 60:176; Fernandez et al. (2000) J Endotoxin Res. 6:321). The invention provides multiple-variable dose methods for inhibiting TNFα activity in a subject suffering from such a hepatic disorder.

As used herein, the term "a hepatic disorder in which TNFα activity is detrimental" is intended to include diseases and other disorders of the liver or conditions associated with hepatocellular injury or a biliary tract disorders in which the presence of TNFα in a subject suffering from the disorder has been shown to be or is suspected of being either responsible for the pathophysiology of the disorder or a factor that contributes to a worsening of the disorder. Accordingly, a hepatic disorder in which TNFα activity is detrimental is a disorder in which inhibition of TNFα activity is expected to alleviate the symptoms and/or progression of the hepatic disorder. In one embodiment, hepatic disorders refers to a human liver disease or condition associated with hepatocellular injury or a biliary tract disorder excluding hepatitis, alcoholic hepatitis, and viral hepatitis.

Examples of animal models used for evaluating the therapeutic efficacy of an agent for treating a hepatic disorder using multiple-variable dose methods include the chimpanzee hepatitis C virus model (see Shimizu et al. (1990) Proc Natl Acad Sci. USA 87:6441). Examples of animal models used to study skin and nail disorder disorders include, for example, the severe combined immunodeficient (SCID) mouse model (psoriasis) and the Smith line (SL) chicken and depigmenting mouse (vitiligo) (see Nickoloff (2000) Investig Dermatol Symp Proc. 5:67; Austin et al. (1995) Am J Pathol. 146: 1529; Lerner et al. (1986) J Invest Dermatol. 87:299).

Hepatic disorders include many diseases and disorders wherein the liver functions improperly or ceases to function. Hepatocellular injuries can include alcoholic cirrhosis, al antitypsin deficiency, autoimmune cirrhosis, cryptogenic cirrhosis, fulminant hepatitis, hepatitis B and C, and steatohepatitis. Examples of biliary tract disorders include cystic fibrosis, primary biliary cirrhosis, sclerosing cholangitis and biliary obstruction (Wiesner (1996) "Current Indications, Contra Indications and Timing for Liver Transplantation" in Transplantation of the Liver, Saunders (publ.); Busuttil and Klintmalm (eds.) Chapter 6; Klein (1998) Partial Hypertension: The Role of Liver Transplantation, Musby (publ.) in Current Surgical Therapy 6. sup.th Ed. Cameron, J. (ed).

The term "hepatitis" refers to inflammation of the liver. Hepatitis can be caused by infections with various organisms, including bacteria, viruses (Hepatitis A, B, C, etc.), or parasites. Chemical toxins such as alcohol, drugs, or poisonous mushrooms can also damage the liver and cause it to become inflamed. A rare but extremely dangerous cause of hepatitis results from overdose of acetaminophen (Tylenol), which can be deadly. In addition, immune cells in the body may attack the liver and cause autoimmune hepatitis. Hepatitis may resolve quickly (acute hepatitis), or cause long-term disease (chronic hepatitis). In some instances, progressive liver damage or liver failure may result. The incidence and severity of hepatitis vary depending on many factors, including the cause of the liver damage and any underlying illnesses in a patient.

In one embodiment, the invention features multiple-variable methods for treating a hepatic disorder in which TNFα activity is detrimental, comprising administering to a subject an effective amount of a TNFα inhibitor in an induction dose and subsequently in a treatment dose, such that said disorder is treated. In one embodiment, the hepatic disorder is selected from the group consisting of hepatitis C virus, autoimmune hepatitis, fatty-liver disease, hepatitis B virus, hepatotoxicity, and non-alcoholic hepatitis, including non-alcoholic steatohepatitis (NASH). Examples of hepatic disorders are further described below.

1. Hepatitis C Virus (HCV)

The methods of the invention may be used to treat subjects having a hepatitis C virus. Tumor necrosis factor has been implicated in the pathophysiology of the hepatitis C virus (see Gonzalez-Amaro. (1994) J Exp Med. 179: 841; Nelson et al. (1997) Dig Dis Sci 42: 2487; Kallinowski et al. (1998) Clin Exp Immunol. 111:269). The term "hepatitis C virus" or "HCV" is used to describe the hepatitis virus which is the causative agent of non-A, non-B hepatitis. Hepatitis C virus causes an inflammation of the liver. HCV infection causes hepatitis C. Hepatitis C in the acute stage is, in general, milder than hepatitis B, but a greater proportion of such infections become chronic. HCV is a major cause of acute hepatitis and chronic liver disease, including cirrhosis and liver cancer.

HCV is one of the viruses (A, B, C, D, and E), which together account for the vast majority of cases of viral hepatitis. It is an enveloped RNA virus in the flaviviridae family which appears to have a narrow host range. An important feature of the virus is the relative mutability of its genome, which in turn is probably related to the high propensity (80%) of inducing chronic infection. HCV is clustered into several distinct genotypes which may be important in determining the severity of the disease and the response to treatment. In one embodiment, the invention provides a multiple-variable dose method for treating HCV.

2. Autoimmune Hepatitis (AIH)

The methods of the invention may be used to treat subjects having autoimmune hepatitis. Tumor necrosis factor has been implicated in the pathophysiology of autoimmune hepatitis (see Cookson et al., (1999) Hepatology 30:851; Jazrawi et al., (2003) Liver Transpl. 9: 377). As used herein, "autoimmune hepatitis" refers to a hepatic disorder characterized by inflammation of the liver caused by rogue immune cells that mistake the liver's normal cells for a foreign tissue or pathogen (disease-causing agent).

Autoimmune hepatitis is often responsible for a progressive destruction of the hepatic parenchyma with a high mortality if left untreated (Johnson et al. (1993) Hepatology, 18:998). One of the characteristics of autoimmune hepatitis is the presence of circulating autoantibodies in almost 90% of patients' sera. Such antibodies can be used to identify subjects who have autoimmune hepatitis.

Clinical and serological differences between patients have lead to the classification of AIH into two types. Type 1 is characterized by the presence of anti-smooth muscle (SMA) and/or anti-nuclear antibodies (ANA) in patients' sera, while sera from Type II patients show anti-liver kidney microsomal antibodies type 1 (LKM1) (Homberg et al., (1987) Hepatology, 7:1333; Maggiore et al. (1993) J. Pediatr. Gastroenterol Nutr. 17:376). A serological marker, anti-liver cytosol type I antibodies (LC1), has been identified in 30% of patients with an AIH type II. In addition, LC1 proved to be the only serological marker in 10% of patients tested (Martini et al. (1988) Hepatology, 8:1662). In one embodiment, the multiple-variable dose method of the invention is used to treat AIH.

3. Fatty-Liver Disease

The methods of the invention may be used to treat subjects having fatty liver disease. Tumor necrosis factor has been implicated in the pathophysiology of fatty-liver disease (see Valenti et al., (2002) Gastroenerology 122: 274; Li et al., (2003) Hepatology 37: 343). Fatty-liver disease refers to a disease wherein fat (hepatocytes) is excessively accumulated in the liver. Fatty liver disease is believed to be caused by supernutrition, hyperingestion of alcohol, diabetes and side effects due to administration of pharmaceuticals. Fatty liver disease can cause severe diseases such as chronic hepatitis and hepatic cirrhosis. In patients with fatty liver disease, lipids, particularly neutral fat, accumulate in hepatocytes to the extent that the amount exceeds the physiologically permissible range. From a biochemical point of view, a standard for judgment of fatty liver is that the weight of neutral fat is 10% (100 mg/g wet weight) or more of the wet weight of hepatic tissue. In one embodiment, the multiple-variable dose method of the invention is used to treat fatty liver disease.

4. Hepatitis B Virus (HBV)

The methods of the invention may be used to treat subjects having hepatitis B virus. Tumor necrosis factor has been implicated in the pathophysiology of hepatitis B virus (see Kasahara et al., (2003) J Virol. 77:2469; Wang (2003) World J Gastroenterol. 9:641; Biermer et al. (2003) J Virol. 77: 4033). The term "hepatitis B virus" (HBV) is used to describe the virus (serum hepatitis virus) which produces viral hepatitis type B in humans. This is a viral disease with a long incubation period (50 to 160 days) in contrast to hepatitis A virus (infectious hepatitis virus) which has a short incubation period. The hepatitis B virus is usually transmitted by injection of infected blood or blood derivatives or merely by use of contaminated needles, lancets or other instruments.

Clinically and pathologically, the disease is similar to viral hepatitis type A; however, there is no cross-protective immunity. Viral antigen (HBAg) is found in the serum after infection.

Hepatitis B virus infects humans at a very high rate. Most people who become infected with Hepatitis B get rid of the virus within 6 months, wherein a short infection is known as an "acute" case of Hepatitis B. It is estimated that at least 300 million people are chronic carriers of HBV. Infection with the virus results in a range of clinical symptoms including minor flu-like symptoms to death. In one embodiment, the multiplevariable dose method of the invention is used to treat HBV infection.

5. Hepatotoxicity

Tumor necrosis factor has been implicated in the pathophysiology of hepatotoxicity (see Bruccoleri et al. (1997) Hepatology 25:133; Luster et al. (2000) Ann NY Acad Sci. 919:214; Simeonova et al. (2001) Toxicol Appl Pharmacol. 177:112). The term hepatotoxicity refers to liver damage caused by medications and other chemicals or drugs. The best indicator for identifying liver toxicity in a subject is the elevation of certain enzyme measurements in the blood, such as AST (aspartate aminotransferase), ALT (alanine aminotransferase), and GOT (glutamate oxalacetate transaminase).

Hepatotoxicity can cause permanent injury and death. Initial symptoms of hepatotoxicity can include acute gastrointestinal symptoms, e.g., severe diarrhea. The second phase of hepatotoxicity is characterized by abatement of symptoms. During this apparent subsidence, biochemical evidence of hepatic injury appears. Oliguria (decreased urine output) is usual during the second phase. The third phase, that of overt hepatic damage, becomes clinically apparent 3 to 5 days after ingestion of the chemical, with the appearance of jaundice. Renal failure may also occur. The symptoms of chemically-induced (drug-induced) hepatitis are similar to that of infectious hepatitis. In one embodiment, the multiple-variable dose method of the invention is used to treat hepatotoxicity.

6. Liver Failure (e. g. Chronic Liver Failure)

The methods of the invention may be used to treat subjects having liver failure. Tumor necrosis factor has been implicated in the pathophysiology of liver failure (e. g. chronic liver failure) (see Takenaka et al., (1998) Dig Dis Sci. 43: 887; Nagaki et al. (1999) J Hepatol. 31:997; Streetz et al., (2000) Gastroenterology. 119:446. Liver failure, including chronic liver failure, usually develops over a period of years and is caused by a repeated insult to the liver (such as alcohol abuse or infection with hepatitis virus) which slowly damages the organ. Less commonly, liver failure is acute, and occurs over a period of days or weeks. Causes of acute liver failure include hepatitis virus infections, drugs, pregnancy, autoimmune disease, and sudden low blood flow to the liver: In one embodiment, the multiple-variable dose method of the invention is used to treat liver failure.

7. Non-Alcoholic Hepatitis, Including NASH

The methods of the invention may be used to treat subjects having a non-alcoholic hepatitis. Tumor necrosis factor has been implicated in the pathophysiology of non-alcoholic hepatitis, including nonalcoholic steatohepatitis (see Crespo et al., (2001) Hepatology. 34: 1158; Pessayre et al. (2002) 282(2):GI 93). The term "nonalcoholic steatohepatitis" or "NASH" refers to the development of histologic changes in the liver that are comparable to those induced by excessive alcohol intake, but in the absence of alcohol abuse. NASH is characterized by macrovesicular and/or microvesicular steatosis, lobular and portal inflammation, and occasionally Mallory bodies with fibrosis and cirrhosis. NASH is also commonly associated with hyperlipidemia, obesity, and type II diabetes mellitus.

Additional clinical conditions which characterize hepatic steatosis and inflammation include excessive fasting, jejunoileal bypass, total parental nutrition, chronic hepatitis C, Wilson's disease, and adverse drug effects such as those from corticosteroids, calcium channel blockers, high dose synthetic estrogens, methotrexate and amiodarone. Thus, the term "nonalcoholic steatohepatitis" can be used to describe those patients who exhibit these biopsy findings, coupled with the absence of (a) significant alcohol consumption, (b) previous surgery for weight loss, (c) history of drug use associated with steatohepatitis, (d) evidence of genetic liver disease or (e) chronic hepatitis C infection (see, e. g., Ludwig et al., (1980) Mayo Clin. Proc. 55: 434; Powell et al. (1990) Hepatol. 11:74). In one embodiment, the multiple-variable dose method of the invention is used to treat NASH.

N. Skin and Nail Disorders

The methods of the invention may be used to treat subjects having a skin or nail disorder. Tumor necrosis factor has been implicated in the pathophysiology of skin and nail disorders. In one embodiment, the multiple-variable dose method of the invention comprising administering an induction dose of a TNFα antibody followed by a subsequent treatment dose, can be used to treat skin and nail disorders. The term "skin disorder" or "skin disease" as used interchangeably herein, refers to abnormalities, other than injury wounds, of the skin which have induced a state of inflammation. In one embodiment, the skin disorder of the invention is an inflammatory skin disorder, wherein the skin is characterized by capillary dilatation, leukocytic infiltration, redness, heat, and/or pain. Examples of skin disorders include, but are not limited to, psoriasis, pemphigus vulgaris, scleroderma, atopic dermatitis, sarcoidosis, erythema nodosum, hidradenitis suppurative, lichen planus, Sweet's syndrome, and vitiligo. As used herein, the term "skin and nail disorder in which TNFα activity is detrimental" is intended to include skin and/or nail disorders and other disorders in which the presence of TNFα in a subject suffering from the disorder has been shown to be or is suspected of being either responsible for the pathophysiology of the disorder or a factor that contributes to a worsening of the disorder, e. g., psoriasis. Accordingly, skin and nail disorders in which TNFα activity is detrimental are disorders in which inhibition of TNFα activity is expected to alleviate the symptoms and/or progression of the disorder. The use of the antibodies, antibody portions, and other TNFα inhibitors of the invention in the treatment of specific skin and nail disorders is discussed further below. In certain embodiments, the treatment method of the invention is performed in combination with another therapeutic agent, as described below in Section IV. In one embodiment, the multiple-variable dose method of the invention comprising administering a TNFα. antibody in combination with another therapeutic agent is used for the treatment of psoriasis and the treatment of psoriasis associated with arthritis.

1. Psoriasis

WO2004009776 teaches the treatment of psoriaisis with Adalimumab.

The methods of the invention may be used to treat subjects having Psoriasis. Tumor necrosis factor has been implicated in the pathophysiology of psoriasis (Takematsu et al. (1989) Arch Dermatol Res. 281:398; Victor and Gottlieb (2002) J Drugs Dermatol. 1:264). The term "psoriasis" as used herein, refers to skin disorders associated with epidermal hyperplasia. Example of psoriasis include, but are not limited to, chronic plaque psoriasis, guttate psoriasis, inverse psoriasis, pustular psoriasis, psoriasis vulgaris, and erythrodermic psoriasis. Psoriasis can also be associated with other inflammatory disorders, including inflammatory bowel disease (IBD) and rheumatoid arthritis (RA).

Psoriasis is described as a skin inflammation (irritation and redness) characterized by frequent episodes of redness, itching, and thick, dry, silvery scales on the skin. In particular, lesions are formed which involve primary and secondary alterations in epidermal proliferation, inflammatory responses of the skin, and an expression of regulatory molecules such as lymphokines and inflammatory factors.

Psoriatic skin is morphologically characterized by an increased turnover of epidermal cells, thickened epidermis, abnormal keratinization, inflammatory cell infiltrates into the epidermis and polymorphonuclear leukocyte and lymphocyte infiltration into the epidermis layer resulting in an increase in the basal cell cycle. Psoriasis often involves the nails, which frequently exhibit pitting, separation of the nail, thickening, and discoloration. Psoriasis is often associated with other inflammatory disorders, for example arthritis, including rheumatoid arthritis, inflammatory bowel disease (IBD), and Crohn's disease. Approximately one thrid of subjects with psoriasis also have psoriatic arthritis (PsA) which, as described above, causes stiffness, swelling of the joints, pain, and reducd range of motion (Greaves et al. (1995) N. Eng. J Med. 332:581).

Evidence of psoriasis is most commonly seen on the trunk, elbows, knees, scalp, skin folds, or fingernails, but it may affect any or all parts of the skin. Normally, it takes a month for new skin cells to move up from the lower layers to the surface. In psoriasis, this process takes only a few days, resulting in a build-up of dead skin cells and formation of thick scales. Symptoms of psoriasis include: skin patches, that are dry or red, covered with silvery scales, raised patches of skin, accompanied by red borders, that may crack and become painful, and that are usually located on the elbows, knees, trunk, scalp, and hands; skin lesions, including pustules, cracking of the skin, and skin redness; joint pain or aching which may be associated with of arthritis, e. g., psoriatic arthritis.

Treatment for psoriasis often includes a topical corticosteroids, vitamin D analogs, and topical or oral retinoids, or combinations thereof. In one embodiment, the TNFα inhibitor of the invention is administered in combination with or the presence of one of these common treatments. Additional therapeutic agents which can also be combined with the TNFα inhibitor of the invention for treatment of psoriasis are described in more detail in Section IV.

The diagnosis of psoriasis is usually based on the appearance of the skin.

Additionally a skin biopsy, or scraping and culture of skin patches may be needed to rule out other skin disorders. An x-ray may be used to check for psoriatic arthritis if joint pain is present and persistent.

Improvements in psoriasis in a subject can be monitored by the subject's Psoriasis Area and Severity Index Score (PASI). The method for determining the PASI has been described in Fredriksson and Pettersson (1978) Dermatologica 157: 238 and Marks et al. (1989) Arch Dermatol 125:235. Briefly, the index is based on evaluation of four anatomic sites, including the head, upper extremities, trunk, and lower extremities, for erythema, induration, and desquamation using a 5 point scale (0=no symptoms; 1=slight; 2=moderate; 3=marked; 4=very marked). Based on the extent of lesions in a given anatomic site, the area affected is assigned a numerical value (0=0; 1=<10%; 2=10-29%; 3=30-49%; 4=50-69%; 5=70=89%; 6=90-100%). The PASI score is then calculated, wherein the possible range of PASI score is 0.0 to 72.0 with the highest score representing complete erythroderma of the severest degree.

In one embodiment of the invention, a TNFα inhibitor is used in multiple-variable dose treatment for psoriasis, including chronic plaque psoriasis, guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). In another embodiment, a TNFα inhibitor, such as D2E7, is used in a multiple variable dose regimen to treat subjects who have psoriasis in combination with PsA. Specific types of psoriasis included in the treatment methods of the invention are described in detail below:

a. Chronic Plaque Psoriasis

The methods of the invention may be used to treat subjects having a chronic plaque psoriasis. Tumor necrosis factor has been implicated in the pathophysiology of chronic plaque psoriasis (Asadullah et al. (1999) Br J Dermatol. 141:94). Chronic plaque psoriasis (also referred to as psoriasis vulgaris) is the most common form of psoriasis.

Chronic plaque psoriasis is characterized by raised reddened patches of skin, ranging from coin-sized to much larger. In chronic plaque psoriasis, the plaques may be single or multiple, they may vary in size from a few millimeters to several centimeters. The plaques are usually red with a scaly surface, and reflect light when gently scratched, creating a "silvery" effect. Lesions (which are often symmetrical) from chronic plaque psoriasis occur all over body, but with predilection for extensor surfaces, including the knees, elbows, lumbosacral regions, scalp, and nails. Occasionally chronic plaque psoriasis can occur on the penis, vulva and flexures, but scaling is usually absent.

Diagnosis of patients with chronic plaque psoriasis is usually based on the clinical features described above. In particular, the distribution, color and typical silvery scaling of the lesion in chronic plaque psoriasis are characteristic of chronic plaque psoriasis.

b. Guttate Psoriasis

The methods of the invention may be used to treat subjects having Guttate psoriasis. Guttate psoriasis refers to a form of psoriasis with characteristic water drop shaped scaly plaques. Flares of guttate psoriasis generally follow an infection, most notably a streptococcal throat infection. Diagnosis of guttate psoriasis is usually based on the appearance of the skin, and the fact that there is often a history of recent sore throat.

c. Inverse Psoriasis

The methods of the invention may be used to treat subjects having inverse psoriasis. Inverse psoriasis is a form of psoriasis in which the patient has smooth, usually moist areas of skin that are red and inflammed, which is unlike the scaling associated with plaque psoriasis. Inverse psoriasis is also referred to as intertiginous psoriasis or flexural psoriasis. Inverse psoriasis occurs mostly in the armpits, groin, under the breasts and in other skin folds around the genitals and buttocks, and, as a result of the locations of presentation, rubbing and sweating can irritate the affected areas.

d. Pustular Psoriasis

The methods of the invention may be used to treat subjects having pustular psoriasis. Pustular psoriasis, also referred to as palmar plantar psoriasis, is a form of psoriasis that causes pus-filled blisters that vary in size and location, but often occur on the hands and feet. The blisters may be localized, or spread over large areas of the body.

Pustular psoriasis can be both tender and painful, can cause fevers.

e. Other Psoriasis Disorders

Other examples of psoriatic disorders which can be treated with the TNFα antibody of the invention include erythrodermic psoriasis, vulgaris, psoriasis associated with IBD, and psoriasis associated with arthritis, including rheumatoid arthritis.

2. Pemphigus Vulgaris

The methods of the invention may be used to treat subjects having pemphigus vulgaris. Pemphigus vulgaris is a serious autoimmune systemic dermatologic disease that often affects the oral mucous membrane and skin. The pathogenesis of pemphigus vulgaris is thought to be an autoimmune process that is directed at skin and oral mucous membrane desmosomes. Consequentially, cells do not adhere to each other. The disorder manifests as large fluid-filled, rupture-prone bullae, and has a distinctive histologic appearance. Anti-inflammatory agents are the only effective therapy for this disease which has a high mortality rate. Complications that arise in patients suffering from pemphigus vulgaris are intractable pain, interference with nutrition and fluid loss, and infections.

3. Atopic Dermatitis/Eczema

The methods of the invention may be used to treat subjects having an atopic dermatitis. Atopic dermatitis (also referred to as eczema) is a chronic skin disorder categorized by scaly and itching plaques. People with eczema often have a family history of allergic conditions like asthma, hay fever, or eczema. Atopic dermatitis is a hypersensitivity reaction (similar to an allergy) which occurs in the skin, causing chronic inflammation. The inflammation causes the skin to become itchy and scaly. Chronic irritation and scratching can cause the skin to thicken and become leathery-textured.

Exposure to environmental irritants can worsen symptoms, as can dryness of the skin, exposure to water, temperature changes, and stress.

Subjects with atopic dermatitis can be identified by certain symptoms, which often include intense itching, blisters with oozing and crusting, skin redness or inflammation around the blisters, rash, dry, leathery skin areas, raw areas of the skin from scratching, and ear discharges/bleeding.

4. Sarcoidosis

The methods of the invention may be used to treat subjects having sarcoidosis. Sarcoidosis is a disease in which granulomatous inflammation occurs in the lymph nodes, lungs, liver, eyes, skin, and/or other tissues. Sarcoidosis includes cutaneous sarcoidosis (sarcoidosis of the skin) and nodular sarcoidosis (sarcoidosis of the lymph nodes). Patients with sarcoidosis can be identified by the symptoms, which often include general discomfort, uneasiness, or an ill feeling; fever; skin lesions.

5. Erythema Nodosum

The methods of the invention may be used to treat subjects having Erythema nodosum. Erythema nodosum refers to an inflammatory disorder that is characterized by tender, red nodules under the skin, typically on the anterior lower legs. Lesions associated with erythema nodosum often begin as flat, but firm, hot red painful lumps (approximately an inch across). Within a few days the lesions may become purplish, and then over several weeks fade to a brownish flat patch.

In some instances, erythema nodosum may be associated with infections including, *streptococcus*, coccidioidomycosis, tuberculosis, hepatitis B, syphilis, cat scratch disease, tularemia, *yersinia*, leptospirosis psittacosis, histoplasmosis, mononucleosis (EBV). In other instances, erythema nodosum may be associated with sensitivity to certain medications including, oralcontraceptives, penicillin, sulfonamides, sulfones, barbiturates, hydantoin, phenacetin, salicylates, iodides, and progestin.

Erythema nodosum is often associated with other disorders including, leukemia, sarcoidosis, rheumatic fever, and ulcerative colitis.

Symptoms of erythema nodosum usually present themselves on the shins, but lesions may also occur on other areas of the body, including the buttocks, calves, ankles, thighs and upper extremities. Other symptoms in subjects with erythema nodosum can include fever and malaise.

6. Hidradenitis Suppurative

The methods of the invention may be used to treat subjects having hidradentis suppurative. Hidradenitis suppurativa refers to a skin disorder in which swollen, painful, inflamed lesions or lumps develop in the groin and sometimes under the arms and under the breasts. Hidradenitis suppurativa occurs when apocrine gland outlets become blocked by perspiration or are unable to drain normally because of incomplete gland, development. Secretions trapped in the glands force perspiration and bacteria into surrounding tissue, causing subcutaneous induration, inflammation, and infection.

Hidradenitis suppurativa is confined to areas of the body that contain apocrine glands.

These areas are the axillae, areola of the nipple, groin, perineum, circumanal, and periumbilical regions.

7. Lichen Planus

The methods of the invention may be used to treat subjects having Lichen planus. Tumor necrosis factor has been implicated in the pathophysiology of lichen planus (Sklavounou et al. (2000) J Oral Pathol Med. 29:370). Lichen planus refers to a disorder of the skin and the mucous membranes resulting in inflammation, itching, and distinctive skin lesions. Lichen planus may be associated with hepatitis C or certain medications.

8. Sweet's Syndrome

The methods of the invention may be used to treat subjects having Sweet's syndrome. Inflammatory cytokines, including tumor necrosis factor, have been implicated in the pathophysiology of Sweet's syndrome (Reuss-Borst et al. (1993) Br J Haematol. 84: 356). Sweet's syndrome, which was described by R. D. Sweet in 1964, is characterized by the sudden onset of fever, leukocytosis, and cutaneous eruption. The eruption consists of tender, erythematous, well-demarcated papules and plaques which show dense neutrophilic infiltrates microscopically. The lesions may appear anywhere, but favor the upper body including the face. The individual lesions are often described as pseudovesicular or pseudopustular, but may be frankly pustular, bullous, or ulcerative.

Oral and eye involvement (conjunctivitis or episcleritis) have also been frequently reported in patients with Sweet's syndrome. Leukemia has also been associated with Sweet's syndrome.

9. Vitiligo

The methods of the invention may be used to treat subjects having virtiligo. Vitiligo refers to a skin condition in which there is loss of pigment from areas of skin resulting in irregular white patches with normal skin texture. Lesions characteristic of vitiligo appear as flat depigmented areas. The edges of the lesions are sharply defined but irregular. Frequently affected areas in subjects with vitiligo include the face, elbows and knees, hands and feet, and genitalia.

10. Scleroderma

The methods of the invention may be used to treat subjects having scleroderma. Tumor necrosis factor has been implicated in the pathophysiology of scleroderma (Tutuncu et al. (2002) Clin Exp Rheumatol. 20(6 Suppl 28):S146; Mackiewicz et al. (2003) Clin Exp Rheumatol. 21:41; Murota et al. (2003) Arthritis Rheum. 48:1117).

Scleroderma refers to a diffuse connective tissue disease characterized by changes in the skin, blood vessels, skeletal muscles, and internal organs. Scleroderma is also referred to as CREST syndrome or progressive systemic sclerosis, and usually affects people between the ages 30-50. Women are affected more often than men.

The cause of scleroderma is unknown. The disease may produce local or systemic symptoms. The course and severity of the disease varies widely in those affected. Excess collagen deposits in the skin and other organs produce the symptoms.

Damage to small blood vessels within the skin and affected organs also occurs. In the skin, ulceration, calcification, and changes in pigmentation may occur. Systemic features may include fibrosis and degeneration of the heart, lungs, kidneys and gastrointestinal tract.

Patients suffering from scleroderma exhibit certain clinical features, including, blanching, blueness, or redness of fingers and toes in response to heat and cold (Raynaud's phenomenon), pain, stiffness, and swelling of fingers and joints, skin thickening and shiny hands and forearm, esophageal reflux or heartburn, difficulty swallowing, and shortness of breath. Other clinical sypmtoms used to diagnose scleroderma include, an elevated erythrocyte sedimentaion rate (ESR), an elevated rheumatoid factor (RF), a positive antinuclear antibody test, urinalysis that shows protein and microscopic blood, a chest X-ray that may show fibrosis, and pulmonary funtion studies that show restricitive lung disease.

11. Nail Disorders

The methods of the invention may be used to treat subjects having a nail disorder. Nail disorders include any abnormality of the nail. The term "nail disorder" or "nail disease" as used herein, refers to conditions wherein the fingernails or toenails to abnormal color, shape, texture, or thickness. Specific nail disorders include, but are not limited to, pitting, koilonychia, Beau's lines, spoon nails, onycholysis, yellow nails, pterygium (seen in lichen planus), and leukonychia. Pitting is characterised by the presence of small depressions on the nail surface. Ridges or linear elevations can develop along the nail occurring in a "lengthwise" or "crosswise" direction. Beau's lines are linear depressions that occur "crosswise" (transverse) in the fingernail. Leukonychia describes white streaks or spots on the nails. Koilonychia is an abnormal shape of the fingernail where the nail has raised ridges and is thin and concave Koilonychia is often associated with iron deficiency.

Nail disorders which can be treated with the TNFα antibody of the invention—also include psoriatic nails. Psoriatic nails include changes in nails which are attributable to psoriasis. In some instances psoriasis may occur only in the nails and nowhere else on the body. Psoriatic changes in nails range from mild to severe, generally reflecting the extent of psoriatic involvement of the nail plate, nail matrix, i. e., tissue from which the nail grows, nail bed, i. e., tissue under the nail, and skin at the base of the nail. Damage to the nail bed by the pustular type of psoriasis can result in loss of the nail. Nail changes in psoriasis fall into general categories that may occur singly or all together. In one category of psoriatic nails, the nail plate is deeply pitted, probably due to defects in nail growth caused by psoriasis. In another category, the nail has a yellow to yellow pink discoloration, probably due to psoriatic involvement of the nail bed. A third subtype of psoriatic nails are characterized by white areas which appear under the nail plate. The white areas are actually air bubbles marking spots where the nail plate is becoming detached from the nail bed. There may also be reddened skin around the nail.

A fourth category is evidenced by the nail plate crumbling in yellowish patches, i. e., onychodystrophy, probably due to psoriatic involvement in the nail matrix. A fifth category is characterized by the loss of the nail in its entirety due to psoriatic involvement of the nail matrix and nail bed.

The multiple-variable dose method of treatment of the invention can also be used to treat nail disorders often associated with lichen planus. Nails in subjects with lichen planus often show thinning and surface roughness of the nail plate with longitudinal ridges or pterygium.

The multiple-variable dose method of treatment of the invention can be used to treat nail disorders, such as those described herein. Often nail disorders are associated with skin disorders. In one embodiment, the invention includes a multiple-variable dose method of treatment for nail disorders using a TNFα antibody. In another embodiment, the nail disorder is associated with another disorder, including a skin disorder such as psoriasis. In another embodiment, the disorder associated with a nail disorder is arthritis, including psoriatic arthritis.

12. Other Skin and Nail Disorders

The multiple-variable dose method of treatment of the invention can be used to treat other skin and nail disorders, such as chronic actinic dermatitis, bullous pemphigoid, and alopecia areata. Chronic actinic dermatitis (CAD) is also referred to as photosensitivity dermatitis/actinic reticuloid syndrome (PD/AR). CAD is a condition in which the skin becomes inflamed, particularly in areas that have been exposed to sunlight or artificial light. Commonly, CAD patients have allergies to certain substances that come into contact with their skin, particularly various flowers, woods, perfumes, sunscreens and rubber compounds. Bullous pemphigoid refers to a skin disorder characterized by the formation of large blisters on the trunk and extremities. Alopecia areata refers to hair loss characterized by round patches of complete baldness in the scalp or beard.

O. Vasculitides

The methods of the invention may be used to treat subjects having vasculitides. TNFα has been implicated in the pathophysiology of a variety of vasculitides, (see e.g., Deguchi et al. (1989) Lancet. 2: 745). In one embodiment, the invention provides a multiple-variable dose method for inhibiting TNFα activity in a subject suffering from a vasculitis in which TNFα activity is detrimental.

The term "vasculitis" or "vasculitides" as used interchangeably herein, refers to a group of disorders which are characterized by the inflammation of blood vessels. Blood vessels of all sizes may be affected, from the largest vessel in the body (the aorta) to the smallest blood vessels in the skin (capillaries). The size of blood vessel affected varies according to the specific type of vasculitis. As used herein, the term "a vasculitis in which TNFα activity is detrimental" is intended to include vasculitis in which the presence of TNFα in a subject suffering from the disorder has been shown to be or is suspected of being either responsible for the pathophysiology of the disorder or a factor that contributes to a worsening of the disorder. Such disorders may be evidenced, for example, by an increase in the concentration of TNFα in a biological fluid of a subject suffering from the disorder (e. g., an increase in the concentration of TNFα in serum, plasma, synovial fluid, etc. of the subject), which can be detected, for example, using an anti-TNFα antibody as described above.

There are numerous examples of vasculitides in which TNFα activity is detrimental, including Behcet's disease. The use of the antibodies, antibody portions, and other TNFα inhibitors for multiple-variable dose treatment of the invention of specific vasculitides is discussed further below. In certain embodiments, the antibody, antibody portion, or other TNFα inhibitor of the invention is administered to the subject in combination with another therapeutic agent, as described below.

The multiple-variable dose regimen of the invention can be used to treat vasculitis in which TNFα activity is detrimental, wherein inhibition of TNFα activity is expected to alleviate the symptoms and/or progression of the vasculitis or to prevent the vasculitis. Subjects suffering from or at risk of developing vasculitis can be identified through clinical symptoms and tests. For example, subjects with vasculitides often develop-antibodies to certain proteins in the cytoplasm of neutrophils, antineutrophil cytoplasmic antibodies (ANCA). Thus, in some instances, vasculitides may be evidenced by tests (e.g., ELISA), which measure ANCA presence.

Vasculitis and its consequences may be the sole manifestation of disease or it may be a secondary component of another primary disease. Vasculitis may be confined to a single organ or it may simultaneously affect several organs and depending on the syndrome, arteries and veins of all sizes can be affected. Vasculitis can affect any organ in the body.

In vasculitis, the vessel lumen is usually compromised, which is associated with ischemia of the tissues supplied by the involved vessel. The broad range of disorders that may result from this process is due to the fact that any type, size and location of vessel (e. g., artery, vein, arteriole, venule, capillary) can be involved. Vasculitides are generally classified according to the size of the affected vessels, as described below. It should be noted that some small and large vessel vasculitides may involve medium-sized arteries; but large and medium-sized vessel vasculitides do not involve vessels smaller than arteries. Large vessel disease includes, but is not limited to, giant cell arteritis, also known as temporal arteritis or cranial arteritis, polymyalgia rheumatica, and Takayasu's disease or arteritis, which is also known as aortic arch syndrome, young female arteritis and Pulseless disease. Medium vessel disease includes, but is not limited to, classic polyarteritis nodosa and Kawasaki's disease, also known as mucocutaneous lymph node syndrome. Non-limiting examples of small vessel disease are Behcet's Syndrome, Wegner's granulomatosis, microscopic polyangitis, hypersensitivity vasculitis, also known as cutaneous vasculitis, small vessel vasculitis, Henoch-Schonlein purpura, allergic granulamotosis and vasculitis, also known as Churg Strauss syndrome. Other vasculitides include, but are not limited to, isolated central nervous system vasculitis, and thromboangitis obliterans, also known as Buerger's disease. Classic Polyarteritis nodosa (PAN), microscopic PAN, and allergic granulomatosis are also often grouped together and are called the systemic necrotizing vasculitides. A further description of vasculitis is described below:

1. Large Vessel Vasculitis

In one embodiment, the TNFα, antibody of the invention is used to treat subjects who have large vessel vasculitis. The term "large vessel (s)" used herein, refers to the aorta and the largest branches directed toward major body regions. Large vessels include, for example, the aorta, and its branches and corresponding veins, e.g., the subclavian artery; the brachiocephalic artery; the common carotid artery; the innonimate vein; internal and external jugular veins; the pulmonary arteries and veins; the venae cavae; the renal arteries and veins; the femoral arteries and veins; and the carotid arteries. Examples of large vessel vasculitides are described below.

a. Giant Cell Arteritis (GCA)

The methods of the invention may be used to treat subjects having giant cell arteritis. Tumor necrosis factor has been implicated in the pathophysiology of giant cell arteritis (Sneller (2002) Cleve. Clin. J. Med. 69:SII40; Schett et al. (2002) Ann. Rheum. Dis. 61:463). Giant cell arteritis (GCA), refers to a vasculitis involving inflammation and damage to blood vessels, particularly the large or medium arteries that branch from the external carotid artery of the neck. GCA is also referred to as temporal arteritis or cranial arteritis, and is the most common primary vasculitis in the elderly. It almost exclusively affects individuals over 50 years of age, however, there are well-documented cases of patients 40 years and younger. GCA usually affects extracranial arteries. GCA can affect the branches of the carotid arteries, including the temporal artery. GCA is also a systemic disease which can involve arteries in multiple locations.

Histopathologically, GCA is a panarteritis with inflammatory mononuclear cell infiltrates within the vessel wall with frequent Langhans type giant cell formation. There is proliferation of the intima, granulomatous inflammation and fragmentation of the internal elastic lamina. The pathological findings in organs is the result of ischemia related to the involved vessels.

Patients suffering from GCA exhibit certain clinical symptoms, including fever, headache, anemia and high erythrocyte sedimentation rate (ESR). Other typical indications of GCA include jaw or tongue claudication, scalp tenderness, constitutional symptoms, pale optic disc edema (particularly 'chalky white' disc edema), and vision disturbances. The diagnosis is confirmed by temporal artery biopsy.

b. Polymyalgia Rheumatica

The methods of the invention may be used to treat subjects having polymyalgia rhumatica. Tumor necrosis factor has been implicated in the pathophysiology of polymyalgia rheumatica (Straub et al. (2002) Rheumatology (Oxford) 41: 423; Uddhammar et al. (1998) Br. J. Rheumatol. 37:766). Polymyalgia rheumatica refers to a rheumatic disorder that is associated with moderate to severe muscle pain and stiffness in the neck, shoulder, and hip, most noticeable in the morning. IL-6 and IL-1 expression has also been detected in a majority of the circulating monocytes in patients with the polymyalgia rheumatica. Polymyalgia rheumatica may occur independently, or it may coexist with or precede GCA, which is an inflammation of blood vessels.

c. Takayasu's Arteritis

The methods of the invention may be used to treat subjects having Takayasu's Arteritis. Tumor necrosis factor has been implicated in the pathophysiology of Takayasu's arteritis (Kobayashi and Numano (2002) Intern. Med. 41: 44; Fraga and Medina (2002) Curr. Rheumatol. Rep. 4:30). Takayasu's arteritis refers to a vasculitis characterized by an inflammmation of the aorta and its major branches. Takayasu's arteritis (also known as Aortic arch syndrome, young female arteritis and Pulseless disease) affects the thoracic and abdominal aorta and its main branches or the pulmonary arteries. Fibrotic thickening of the aortic wall and its branches (e.g., carotid, inominate, and subclavian arteries) can lead to reduction of lumen size of vessels that arise from the aortic arch.

This condition also typically affects the renal arteries.

Takayasu's arteritis primarily affects young women, usually aged 20-40 years old, particularly of Asian descent, and may be manifested by malaise, arthralgias and the gradual onset of extremity claudication. Most patients have asymmetrically reduced pulses, usually along with a blood pressure differential in the arms. Coronary and/or renal artery stenosis may occur.

The clinical features of Takayasu's arteritis may be divided into the features of the early inflammatory disease and the features of the later disease. The clinical features of the early inflammatory stage of Takayasu's disease are: malaise, low grade fever, weight loss, myalgia, arthralgia, and erythema multiforme. Later stages of Takayasu's disease are characterized by fibrotic stenosis of arteries and thrombosis. The main resulting clinical features are ischaemic phenomena, e.g. weak and asymmetrical arterial pulses, blood pressure discrepancy between the arms, visual disturbance, e. g. scotomata and hemianopia, other neurological features including vertigo and syncope, hemiparesis or stroke. The clinical features result from ischaemia due to arterial stenosis and thrombosis.

2. Medium Vessel Disease

In one embodiment, the TNFα antibody of the invention is used to treat subjects who have medium vessel vasculitis. The term "medium vessel (s)" used to refer to those blood vessels which are the main visceral arteries. Examples of medium vessels include the mesenteric arteries and veins, the iliac arteries and veins, and the maxillary arteries and veins. Examples of medium vessel vasculitides are described below. a. Polyarteritis Nodosa Tumor necrosis factor has been implicated in the pathophysiology of polyarteritis nodosa (DiGirolamo et al. (1997) J. Leukoc. Biol. 61: 667). Polyarteritis nodosa, or periarteritis nodosa refers to vasculitis which is a serious blood vessel disease in which small and medium-sized arteries become swollen and damaged because they are attacked by rogue immune cells. Polyarteritis nodosa usually affects adults more frequently than children. It damages the tissues supplied by the affected arteries because they don't receive enough oxygen and nourishment without a proper blood supply.

Symptoms which are exhibited in patients with polyarteritis nodosa generally result from damage to affected organs, often the skin, heart, kidneys, and nervous system. Generalized symptoms of polyarteritis nodosa include fever, fatigue, weakness, loss of appetite, and weight loss. Muscle aches (myalgia) and joint aches (arthralgia) common. The skin of subjects with polyarteritis nodosa may also show rashes, swelling, ulcers, and lumps (nodular lesions).

Classic PAN (polyarteritis nodosa) is a systemic arteritis of small to medium muscular arteritis in which involvement of renal and visceral arteries is common.

Abdominal vessels have aneurysms or occlusions in 50% of PAN patients. Classic PAN does not involve the pulmonary arteries although the bronchial vessels may be involved.

Granulomas, significant eosinophilia and an allergic diathesis are not part of the syndrome. Although any organ system may be involved, the most common manifestations include peripheral neuropathy, mononeuritis multiplex, intestinal ischemia, renal ischemia, testicular pain and livedo reticularis.

b. Kawasaki's Disease

The methods of the invention may be used to treat subjects having Kawasaki's Disease. Tumor necrosis factor has been implicated in the pathophysiology of Kawasaki's disease (Sundel (2002) Curr. Rheumatol. Rep. 4: 474; Gedalia (2002) Curr. Rheumatol. Rep. 4: 25). Although the cause of Kawasaki's disease is unknown, it is associated with acute inflammation of the coronary arteries, suggesting that the tissue damage associated with this disease may be mediated by proinflammatory agents such as TNFα.

Kawasaki's disease refers to a vasculitis that affects the mucus membranes, lymph nodes, lining of the blood vessels, and the heart. Kawasaki's disease is also often referred to as mucocutaneous lymph node syndrome, mucocutaneous lymph node disease, and infantile polyarteritis. Subjects afflicted with Kawasaki's disease develop vasculitis often involving the coronary arteries which can lead to myocarditis and pericarditis.

Often as the acute inflammation diminishes, the coronary arteries may develop aneurysm, thrombosis, and lead to myocardial infarction.

Kawasaki's disease is a febrile systemic vasculitis associated with edema in the palms and the soles of the feet, with enlargement of cervical lymph nodes, cracked lips and "strawberry tongue". Although the inflammatory response is found in vessels throughout the body, the most common site of end-organ damage is the coronary arteries. Kawasaki's Disease predominantly affects children under the age of 5. The highest incidence is in Japan but is becoming increasingly recognized in the West and is now the leading cause of acquired heart disease in US children. The most serious complication of Kawasaki disease is coronary arteritis and aneurysm formation that occurs in a third of untreated patients.

3. Small Vessel Disease

In one embodiment, the TNFα antibody of the invention is used to treat subjects who have small vessel vasculitis. The term "small vessel (s)" used to refer to arterioles, venules and capillaries. Arterioles are arteries that contain only 1 or 2 layers of smooth muscle cells and are terminal to and continuous with the capillary network.

Venules carry blood from the capillary network to veins and capillaries connect arterioles and venules. Examples of small vessel vasculitides are described below. a. Behcet's Disease Tumor necrosis factor has been implicated in the pathophysiology of Behcet's disease (Sfikakis (2002) Ann. Rheum. Dis. 61: ii51-3; Dogan and Farah (2002) Oftalmologia. 52: 23). Behcet's disease is a chronic disorder that involves inflammation of blood vessels throughout the body. Behcet's disease may also cause various types of skin lesions, arthritis, bowel inflammation, and meningitis (inflammation of the membranes of the brain and spinal cord). As a result of Behcet's disease, the subject with the disorder may have inflammation in tissues and organs throughout the body, including the gastrointestinal tract, central nervous system, vascular system, lungs, and kidneys. Behcet's disease is three times more common in males than females and is more common in the eastern Mediterranean and Japan.

Subjects who have Behcet's disease may show clinical symptoms including recurrent oral ulcers (resembling canker sores), recurrent genital ulcers, and eye inflammation. Serum levels of TNFα, IL-8, IL-1, IL-6 INF-y and IL-12 are elevated in Behcet's patients, and the production of these factors has been shown to be elevated in the monocytes of Behcet's patients (see, e.g., Inflammatory Disease of Blood Vessels (2001) Marcel Dekker, Inc., eds. G. S. Hoffman and C. M. Weyand, p. 473). b. Wegener's granulomatosis Tumor necrosis factor has been implicated in the pathophysiology of Wegener's granulomatosis (Marquez et al. (2003) Curr. Rheumatol. Rep. 5: 128; Harman and Margo (1998) Surv. Ophthalmol. 42:458). Wegener's granulomatosis refers to a vasculitis that causes inflammation of blood vessels in the upper respiratory tract (nose, sinuses, ears), lungs, and kidneys. Wegener's granulomatosis is also referred to as midline granulomatosis. Wegener's granulomatosis includes a granulomatous inflammation involving the respiratory tract, and necrotizing vasculitis affecting small to medium-sized vessels. Subjects who have Wegener's granulomatosis often also have arthritis (joint inflammation). Glomerulonephritis may also be present in affected subjects, but virtually any organ may be involved.

Patients affected with Wegener's granulomatosis typically show clinical symptoms comprising recurrent sinusitis or epistaxis, mucosal ulcerations, otitis media, cough, hemoptysis and dyspnea. The first symptoms of Wegener's granulomatosis frequently include upper respiratory tract symptoms, joint pains, weakness, and tiredness.

c. Churg-Strauss Syndrome

The methods of the invention may be used to treat subjects having Churg-Strauss syndrome. Tumor necrosis factor has been implicated in the pathophysiology of Churg Strauss syndrome (Gross (2002) Curr. Opin. Rheumatol. 14: 11; Churg (2001) Mod. Pathol. 14: 1284). Churg-Strauss syndrome refers to a vasculitis that is systemic and shows early manifestation signs of asthma and eosinophilia. Churg-Strauss syndrome is also referred to as allergic granulomatosis and angiitis, and occurs in the setting of allergic rhinitis, asthma and eosinophilia. Sinusitis and pulmonary infiltrates also occur in Churg-Strauss syndrome, primarily affecting the lung and heart. Peripheral neuropathy, coronary arteritis and gastrointestinal involvement are common.

Patients afflicted with Churg-Strauss syndrome can be diagnosed according to criteria established by the American College of Rheumatology (ACR). These criteria were intended to distinguish CSS from other forms of vasculitis. Not all patients meet every criterion. Some, in fact, may have only 2 or 3 criteria, yet they are still classified as Churg-Strauss syndrome. The ACR selected 6 disease features (criteria) as being those that best distinguished Churg-Strauss syndrome—from other vasculitides. These criteria include: 1) asthma; 2) eosinophilia [>10% on differential WBC count]; 3) mononeuropathy; 4) transient pulmonary infiltrates on chest X-rays; 5) paranasal sinus abnormalities; and 6) biopsy containing a blood vessel with extravascular eosinophils.

P. Other TNFα-Related Disorders

In one embodiment, the invention features a multiple-variable dose method for treating a TNFα-related disorder in which TNFα activity is detrimental, comprising administering to a subject an induction dose of a TNFα inhibitor and a subsequent treatment dose, such that said TNFα-related disorder is treated. Examples of TNFα-related disorders in which TNFα activity is detrimental, are discussed further below.

1. Juvenile Arthritis

The methods of the invention may be used to treat subjects having juvenile arthritis. Tumor necrosis factor has been implicated in the pathophysiology of juvenile arthritis, including juvenile rheumatoid arthritis (Grom et al. (1996) Arthritis Rheum. 39:1703; Mangge et al. (1995) Arthritis Rheum. 8:211). In one embodiment, the TNFα antibody of the invention is used to treat juvenile rheumatoid arthritis.

The term "juvenile rheumatoid arthritis" or "JRA" as used herein refers to a chronic, inflammatory disease which occurs before age 16 that may cause joint or connective tissue damage. JRA is also referred to as juvenile chronic polyarthritis and Still's disease.

JRA causes joint inflammation and stiffness for more than 6 weeks in a child of 16 years of age or less. Inflammation causes redness, swelling, warmth, and soreness in the joints. Any joint can be affected and inflammation may limit the mobility of affected joints. One type of JRA can also affect the internal organs.

JRA is often classified into three types by the number of joints involved, the symptoms, and the presence or absence of certain antibodies found by a blood test.

These classifications help the physician determine how the disease will progress and whether the internal organs or skin is affected. The classifications of JRA include the following a. Pauciarticular JRA, wherein the patient has four or fewer joints are affected. Pauciarticular is the most common form of JRA, and typically affects large joints, such as the knees. b. Polyarticular HRA, wherein five or more joints are affected. The small joints, such as those in the hands and feet, are most commonly involved, but the disease may also affect large joints. c. Systemic JRA is characterized by joint swelling, fever, a light skin rash, and may also affect internal organs such as the heart, liver, spleen, and lymph nodes.

Systemic JRA is also referred to as it Still's disease. A small percentage of these children develop arthritis in many joints and can have severe arthritis that continues into adulthood.

2. Endometriosis

The methods of the invention may be used to treat subjects having endometriosis. Tumor necrosis factor has been implicated in the pathophysiology of endometriosis, as women with endometriosis have elevated peritoneal levels of TNF (Eisermann et al. (1988) Fertil Steril 50:573; Halme (1989) Am J Obstet Gynecol 161:1718; Mori et al. (1991) Am J Reprod Immunol 26:62; Taketani et al. (1992) Am J Obstet Gynecol 167:265; Overton et al. (1996) Hum Reprod 1996; 11:380). In one embodiment, the TNFα antibody of the invention is used to treat endometriosis. The term "endometriosis" as used herein refers to a condition in which the tissue that normally lines the uterus (endometrium) grows in other areas of the body, causing pain, irregular bleeding, and frequently infertility.

3. Prostatitis

The methods of the invention may be used to treat subjects having prostatitis. Tumor necrosis factor has been implicated in the pathophysiology of prostatitis, as men with chronic prostatitis and chronic pelvic pain have significantly higher levels of TNF and IL-1 in semen compared to controls (Alexander et al. (1998) Urology 52: 744; Nadler et al. (2000) J Urol 164:214; Orhan et al. (2001) Int J Urol 8: 495) Furthermore, in a rat model of prostatitis TNF levels were also increased in comparison to controls (Asakawa et al. (2001) Hinyokika Kiyo 47: 459; Harris et al. (2000) Prostate 44: 25). In one embodiment, the TNFα antibody of the invention is used to treat prostatitis.

The term "prostatitis" as used herein refers to an inflammation of the prostate.

Prostatitis is also referred to as pelvic pain syndrome. Prostatitis manifests itself in a variety of forms, including nonbacterial prostatitis, acute prostatitis, bacterial prostatitis, and acute prostatitis. Acute prostatitis refers to an inflammation of the prostate gland that develops suddenly. Acute prostatitis is usually caused by a bacterial infection of the prostate gland. Chronic prostatitis is an inflammation of the prostate gland that develops gradually, continues for a prolonged period, and typically has subtle symptoms. Chronic prostatitis is also usually caused by a bacterial infection 4. Choroidal Neovascularization The methods of the invention may be used to treat subjects having choroidal neovascularization. Tumor necrosis factor has been implicated in the pathophysiology of choroidal neovascularization. For example, in surgically excised choroidal neovascular membranes, neovascular vessels stained positive for both TNF and IL-1 (Oh H et al. (1999) Invest Ophthalmol Vis Sci 40: 1891). In one embodiment, the TNFα antibody of the invention is used to treat choroidal neovascularization. The term "choroidal neovascularization" as used herein refers to the growth of new blood vessels that originate from the choroid through a break in the Bruch membrane into the sub-retinal pigment epithelium (sub-RPE) or subretinal space. Choroidal neovascularization (CNV) is a major cause of visual loss in patients with the condition.

5. Sciatica

The methods of the invention may be used to treat subjects having sciatica. Tumor necrosis factor has been implicated in the pathophysiology of sciatica (Ozaktay et al. (2002) Eur Spine J. 11:467; Brisby et al. (2002) Eur Spine J. 11:62). In one embodiment, the TNFα antibody of the invention is used to treat sciatica. The term "sciatica" as used herein refers to a condition involving impaired movement and/or sensation in the leg, caused by damage to the sciatic nerve. Sciatica is also commonly referred to as neuropathy of the sciatic nerve and sciatic nerve dysfunction. Sciatica is a form of peripheral neuropathy. It occurs when there is damage to the sciatic nerve, located in the back of the leg. The sciatic nerve controls the muscles of the back of the knee and lower leg and provides sensation to the back of the thigh, part of the lower leg and the sole of the foot. Sciatica can be indicative of another disorder, including a lumbar herniated disc, spinal stenosis, degenerative disc disease, isthmic spondyloisthesis and piniformis syndrome.

6. Sjogren's Syndrome

The methods of the invention may be used to treat subjects having Sjogren's syndrome. Tumor necrosis factor has been implicated in the pathophysiology of Sjogren's syndrome (Koski et al. (2001) Clin Exp Rheumatol. 19:131). In one embodiment, the TNFα antibody of the invention is used to treat Sjogren's syndrome. The term "Sjogren's syndrome" as used herein refers to a systemic inflammatory disorder characterized by dry mouth, decreased tearing, and other dry mucous membranes, and is often associated with autoimmune rheumatic disorders, such as rheumatoid arthritis. Dryness of the eyes and mouth are the most common symptoms of this syndrome. The symptoms may occur alone, or with symptoms associated with rheumatoid arthritis or other connective tissue diseases. There may be an associated enlargement of the salivary glands. Other organs may become-affected. The syndrome may be associated with rheumatoid arthritis, systemic lupus erythematosus, scleroderma, polymyositis, and other diseases.

7. Uveitis

The methods of the invention may be used to treat subjects having Uveitis. Tumor necrosis factor has been implicated in the pathophysiology of uveitis (Wakefield and Lloyd (1992) Cytokine 4:1; Woon et al. (1998) Curr Eye Res. 17:955).

In one embodiment, the TNFα antibody of the invention is used to treat uveitis. The term "uveitis" as used herein refers to an inflammation of the the uvea, which is the layer between the sclera and the retina, which includes the iris, ciliary body, and the choroid.

Uveitis is also commonly referred to as iritis, pars planitis, chroiditis, chorioretinitis, anterior uveitis, and posterior uveitis. The most common form of uveitis is anterior uveitis, which involves inflammation in the front part of the eye, which is usually isolated to the iris. This condition is often called iritis. In one embodiment, the term uveitis refers to an inflammation of the the uvea which excludes inflammation associated with an autoimmune disease, i. e., excludes autoimmune uveitis.

8. Wet Macular Degeneration

The methods of the invention may be used to treat subjects having wet macular degeneration. Tumor necrosis factor has been implicated in the pathophysiology of wet macular degeneration. In one embodiment, the TNFα antibody of the invention is used to treat wet macular degeneration. The term "wet macular degeneration" as used herein refers to a disorder that affects the macula (the central part of the retina of the eye) and causes decreased visual acuity and possible loss of central vision. Patients with wet macular degeneration develop new blood vessels under the retina, which causes hemorrhage, swelling, and scar tissue.

9. Osteoporosis

The methods of the invention may be used to treat subjects having osteoporosis. Tumor necrosis factor has been implicated in the pathophysiology of osteoporosis, (Tsutsumimoto et al. (1999) J Bone Miner Res. 14:1751). Osteoporosis is used to refer to a disorder characterized by the progressive loss of bone density and thinning of bone tissue. Osteoporosis occurs when the body fails to form enough new bone, or when too much old bone is reabsorbed by the body, or both. The TNFα antibody, or antigen-binding fragment thereof, of the invention can be used to treat osteoporosis.

10. Osteoarthritis

The methods of the invention may be used to treat subjects having osteoarthritis. Tumor necrosis factor has been implicated in the pathophysiology of osteoarthritis, (Venn et al. (1993) Arthritis Rheum. 36: 819; Westacott et al. (1994) J Rheumatol. 21:1710). Osteoarthritis (OA) is also referred to as hypertrophic osteoarthritis, osteoarthrosis, and degenerative joint disease. OA is a chronic degenerative disease of skeletal joints, which affects specific joints, commonly knees, hips, hand joints and spine, in adults of all ages. OA is characterized by a number of the following manifestations including degeneration and thinning of the articular cartilage with associated development of "ulcers" or craters, osteophyte formation, hypertrophy of bone at the margins, and changes in the snyovial membrane and enlargement of affected joints. Furthermore, osteoarthritis is accompanied by pain and stiffness, particularly after prolonged activity. The antibody, or antigen-binding fragment thereof, of the invention can be used to treat osteoarthritis. Characteristic radiographic features of osteoarthritis include joint space narrowing, subchondral sclerosis, osteophytosis, subchondral cyst formation, loose osseous body (or "joint mouse").

Medications used to treat osteoarthritis include a variety of nonsteroidal, anti-inflammatory drugs (NSAIDs). In addition, COX 2 inhibitors, including Celebrex, Vioxx, and Bextra, aand Etoricoxib, are also used to treat OA. Steroids, which are injected directly into the joint, may also be used to reduce inflammation and pain. In one embodiment of the invention, TNFα antibodies of the invention are administered in combination with a NSAIDs, a COX2 inhibitor, and/or steroids.

11. Other

The methods of the invention, also can be used to treat various other disorders in which TNFα activity is detrimental. Examples of other diseases and disorders in which TNFα activity has been implicated in the pathophysiology, and thus which can be treated using an antibody, or antibody portion, of the invention, include inflammatory bone disorders, bone resorption disease, coagulation disturbances, burns, reperfusion injury, keloid formation, scar tissue formation, pyrexia, periodontal disease, obesity, radiation toxicity, age-related cachexia, Alzheimer's disease, brain edema, inflammatory brain injury, cancer, chronic fatigue syndrome, dermatomyositis, drug reactions, such as Stevens-Johnson syndrome and Jarisch-Herxheimer reaction, edema in and/or around the spinal cord, familial periodic fevers, Felty's syndrome, fibrosis, glomerulonephritides (e. g. post-streptococcal glomerulonephritis or IgA nephropathy), loosening of prostheses, microscopic polyangiitis, mixed connective tissue disorder, multiple myeloma, cancer and cachexia, multiple organ disorder, myelo dysplastic syndrome, orchitism osteolysis, pancreatitis, including acute, chronic, and pancreatic abscess, polymyositis, progressive renal failure, pseudogout, pyoderma gangrenosum, relapsing polychondritis, rheumatic heart disease, sarcoidosis, sclerosing cholangitis, stroke, thoracoabdominal aortic aneurysm repair (TAAA), TNF receptor associated periodic syndrome (TRAPS), symptoms related to Yellow Fever vaccination, inflammatory diseases associated with the ear, chronic ear inflammation, chronic otitis media with or without cholesteatoma, pediatric ear inflammation, myotosis, ovarian cancer, colorectal cancer, therapy associated with induced inflammatory syndrome (e. g., syndromes following IL-2 administration), and a disorder associated with a reperfussion injury.

It is understood that all of the above-mentioned TNFα-related disorders include both the adult and juvenile forms of the disease where appropriate. It is also understood that all of the above-mentioned disorders include both chronic and acute forms of the disease. In addition, the multiple-variable dose methods of the invention can be used to treat each of the above-mentioned TNFα-related disorders alone or in combination with one another, e. g., a subject who is suffering from uveitis and lupus.

IV. Pharmaceutical Compositions and Pharmaceutical Administration

A. Administration

The inventors have identified that administration of a higher induction dose (e.g. higher than the currently approved induction dose of 160 mg or 80 mg) of an anti-TNFα antibody, such as adalimumab or a biosimilar thereof, provides improved induction efficacy, for treating a disorder in which TNFα activity is detrimental.

The invention provides a multiple-variable dose method for treating a disorder in which TNFα activity is detrimental, comprising administering to a subject in need thereof at least one higher than standard induction dose of an anti-TNFα antibody, such as adalimumab or a biosimilar thereof, such that a threshold level of TNFα inhibitor is achieved within an induction phase, and subsequently administering to the subject a treatment dose of the human antibody within a treatment phase, such that treatment occurs.

The multiple-variable dose treatment method of the invention comprises administering a therapeutic agent in an induction phase, followed by a lower amount of the therapeutic agent during a treatment phase. The induction phase is complete once a threshold level of therapeutic agent is reached. The induction phase can include a single induction dose, or multiple induction doses wherein the same or different amounts of therapeutic agent are used. More than one induction dose may be administered during the induction phase, wherein any determined amount of time interval may occur between induction doses, including, for example, one hour apart, one day apart, one week apart, two weeks apart, etc.

In one embodiment, the induction phase comprises administration of a first induction dose which ranges from 161 to 320 mg of an anti-TNFα antibody, such as adalimumab or a biosimilar thereof. In one embodiment, the induction phase comprises administration of a first induction dose which ranges from 161 to 300 mg, 161 to 280 mg, 161 to 260 mg, 161 to 240 mg, 161 to 220 mg, 161 to 200 mg of an anti-TNFα antibody, such as adalimumab or a biosimilar thereof. In one embodiment, the induction phase comprises administration of a first induction dose which ranges from 180 to 300 mg, 180 to 280 mg, 180 to 260 mg, 180 to 240 mg, 180 to 220 mg, 180 to 200 mg of an anti-TNFα antibody, such as adalimumab or a biosimilar thereof. In one embodiment, the induction phase comprises administration of a first induction dose which ranges from 200 to 300 mg, 200 to 280 mg, 200 to 260 mg, 200 to 240 mg, 200 to 220 mg and 200 to 210 mg of an anti-TNFα antibody, such as adalimumab or a biosimilar thereof. Ranges intermediate to the above recited dosages, e. g. 170.5 to 200.5; are also intended to be part of this invention. For example, ranges of values using a combination of any of the above recited values as upper and/or lower limits are intended to be included.

In one embodiment the induction phase comprises administration of a first induction dose of 161, 170, 180, 190, 200, 210, 220, 230, 240, 250, 260, 270, 280, 290, 300, 310 or 320 mg of an anti-TNFα antibody, such as adalimumab or a biosimilar thereof. In still another embodiment, the induction phase comprises a first induction dose of 180 mg of an anti-TNFα antibody, such as adalimumab or a biosimilar thereof. In still another embodiment, the induction phase comprises a first induction dose of 200 mg of an anti-TNFα antibody, such as adalimumab or a biosimilar thereof. In still another embodiment, the induction phase comprises a first induction dose of 210 mg of an anti-TNFα antibody, such as adalimumab or a biosimilar thereof. In still another embodiment, the induction phase comprises a first induction dose of 220 mg of an anti-TNFα antibody, such as adalimumab or a biosimilar thereof. In still another embodiment, the induction phase comprises a first induction dose of 230 mg of an anti-TNFα antibody, such as adalimumab or a biosimilar thereof. In still another embodiment, the induction phase comprises a first induction dose of 240 mg of an anti-TNFα antibody, such as adalimumab or a biosimilar thereof. In still another embodiment, the induction phase comprises a first induction dose of 280 mg of an anti-TNFα antibody, such as adalimumab or a biosimilar thereof. In still another embodiment, the induction phase comprises a first induction dose of 320 mg of an anti-TNFα antibody, such as adalimumab or a biosimilar thereof.

In one embodiment, the induction phase comprises administration of a second induction dose, subsequent to said first induction dose, which second induction dose is 40% to 60% of said first induction dose. In one embodiment the second induction dose is 50% of said first induction dose.

In one embodiment, the induction phase comprises administration of a second induction dose, subsequent to said first induction dose, which ranges from 80 to 160 mg of an anti-TNFα antibody, such as adalimumab or a biosimilar thereof. In one embodiment, the induction phase comprises administration of a second induction dose, subsequent to said first induction dose, which ranges from 80 to 150 mg, 80 to 140 mg, 80 to 130 mg, 80 to 120 mg, 80 to 110 mg, 80 to 100 mg of an anti-TNFα antibody, such as adalimumab or a biosimilar thereof. In one embodiment, the induction phase comprises administration of a second induction dose, subsequent to said first induction dose, which ranges from 90 to 160 mg, 90 to 150 mg, 90 to 140 mg, 90 to 130 mg, 90 to 120 mg, 90 to 110 mg, 90 to 100 mg of an anti-TNFα antibody, such as adalimumab or a biosimilar thereof In one embodiment, the induction phase comprises administration of a second induction dose, subsequent to said first induction dose, which ranges from 100 to 160 mg, 100 to 150 mg, 100 to 140 mg, 100 to 130 mg, 100 to 120 mg, and 100 to 110 mg of an anti-TNFα antibody, such as adalimumab or a biosimilar thereof In one embodiment the induction phase comprises administration of a second induction dose of 80, 90, 100, 110, 120, 130, 140, 150 or 160 mg of an anti-TNFα antibody, such as adalimumab or a biosimilar thereof. In still another embodiment, the induction phase comprises a second induction dose of 80 mg of an anti-TNFα antibody, such as adalimumab or a biosimilar thereof. In still another embodiment, the induction phase comprises a second induction dose of 90 mg of an anti-TNFα antibody, such as adalimumab or a biosimilar thereof. In still another embodiment, the induction phase comprises a second induction dose of 100 mg of an anti-TNFα antibody, such as adalimumab or a biosimilar thereof. In still another embodiment, the induction phase comprises a second induction dose of 110 mg of an anti-TNFα antibody, such as adalimumab or a biosimilar thereof. In still another embodiment, the induction phase comprises a second induction dose of 120 mg of an anti-TNFα antibody, such as adalimumab or a biosimilar thereof. In still another embodiment, the induction phase comprises a second induction dose of 130 mg of an anti-TNFα antibody, such as adalimumab or a biosimilar thereof. In still another embodiment, the induction phase comprises a second induction dose of 140 mg of an anti-TNFα antibody, such as adalimumab or a biosimilar thereof. In still another embodiment, the induction phase comprises a second induction dose of 150 mg of an anti-TNFα antibody, such as adalimumab or a biosimilar thereof. In still another embodiment, the induction phase comprises a second induction dose of 160 mg of an anti-TNFα antibody, such as adalimumab or a biosimilar thereof.

In one embodiment the induction phase comprises a first induction dose of 200 mg of an anti-TNFα antibody, such as adalimumab or a biosimilar thereof and a second induction dose of 80 mg, 90 mg, 100 mg, 110 mg, 120 mg, 130 mg, 140 mg, 150 mg or 160 mg of the anti-TNFα antibody. In one embodiment the induction phase comprises a first induction dose of 210 mg of an anti-TNFα antibody, such as adalimumab or a biosimilar thereof and a second induction dose of 80 mg, 90 mg, 100 mg, 110 mg, 120 mg, 130 mg, 140 mg, 150 mg or 160 mg of the anti-TNFα antibody. In one embodiment the induction phase comprises a first induction dose of 220 mg of an anti-TNFα antibody, such as adalimumab or a biosimilar thereof and a second induction dose of 80 mg, 90 mg, 100 mg, 110 mg, 120 mg, 130 mg, 140 mg, 150 mg or 160 mg of the anti-TNFα antibody. In one embodiment the induction phase comprises a first induction dose of 230 mg of an anti-TNFα antibody, such as adalimumab or a biosimilar thereof and a second induction dose of 80 mg, 90 mg, 100 mg, 110 mg, 120 mg, 130 mg, 140 mg, 150 mg or 160 mg of the anti-TNFα antibody. In still another embodiment the induction phase comprises a first induction dose of 240 mg of an anti-TNFα antibody, such as adalimumab or a biosimilar thereof and a second induction dose of 80 mg, 90 mg, 100 mg, 110 mg, 120 mg, 130 mg, 140 mg, 150 mg or 160 mg of the anti-TNFα antibody. In still another embodiment the induction phase comprises a first induction dose of 280 mg of an anti-TNFα antibody, such as adalimumab or a biosimilar thereof and a second induction dose of 80 mg, 90 mg, 100 mg, 110 mg, 120 mg, 130 mg, 140 mg, 150 mg or 160 mg of the anti-TNFα antibody. In still another embodiment the induction phase comprises a first induction dose of 320 mg of an anti-TNFα antibody, such as adalimumab or a biosimilar thereof and a second induction dose of 80 mg, 90 mg, 100 mg, 110 mg, 120 mg, 130 mg, 140 mg, 150 mg or 160 mg of the anti-TNFα antibody.

In one embodiment said second induction dose is administered 5, 6, 7, 8, 9, 10, 11, 12, 13 or 14 days after said first induction dose. Preferably, said second induction dose is administered 7 days after said first induction dose, i.e. a week apart.

A threshold level is achieved once a pre-determined therapeutic effect is reached.

For example, the threshold level of a TNFα inhibitor for the treatment of Crohn's disease may be determined by monitoring a subject in the induction phase of treatment for a reduction in their CDAI index. In another example, the threshold level of a TNFα inhibitor for treatment of psoriasis may be determined by a decrease in psoriatic plaques, an improvement in the patient's Psoriasis Area Severity Index (PASI) score, or an improved Physician's Global Assessment (PGA) score. In still another example, the threshold level of a TNFα inhibitor for treatment of a TNFα-related disorder is determined by achievement of a stable blood plasma serum concentration of the TNFα inhibitor.

Once a threshold level is achieved, the treatment phase is initiated. At least one treatment dose is administered during the treatment phase. More than one treatment dose may administered during the treatment phase, wherein any determined amount of time interval may occur between induction doses, including, for example, one hour apart, one day apart, one week apart, two weeks apart, etc.

The multiple-variable dose method described herein is based on a treatment regimen which includes administration of at least two different doses of an anti-TNFα antibody, such as adalimumab or a biosimilar thereof. An induction dose can be any multiple number greater than the treatment dose. For example, the first induction dose can be two, three, four, five, six, seven or eight times greater than the treatment dose.

In one embodiment, the treatment dose is 40% to 60% of said first induction dose. In one embodiment the second induction dose is 50% of said first induction dose. In one embodiment, the treatment dose is 40% to 60% of said second dose. In one embodiment the treatment dose is 50% of said second induction dose.

In one embodiment, the treatment dose ranges from 20 to 160 mg, 20 to 150 mg, 20 to 140 mg, 20 to 130 mg, 20 to 120 mg, 20 to 110 mg, 20 to 100 mg, 20 to 90 mg, 20 to 80 mg, 20 to 70 mg, 20 to 60 mg, 20 to 50 mg and 20 to 40 mg of an anti-TNFα antibody, such as adalimumab or a biosimilar thereof. In one embodiment, the treatment dose ranges from 40 to 160 mg, 40 to 150 mg, 40 to 140 mg, 40 to 130 mg, 40 to 120 mg, 40 to 110 mg, 40 to 100 mg, 40 to 90 mg, 40 to 80 mg, 40 to 70 mg, 40 to 60 mg, and 40 to 50 mg of an anti-TNFα antibody, such as adalimumab or a biosimilar thereof. In one embodiment, the treatment dose ranges from 50 to 160 mg, 50 to 150 mg, 50 to 140 mg, 50 to 130 mg, 50 to 120 mg, 50 to 110 mg, 50 to 100 mg, 50 to 90 mg, 50 to 80 mg, 50 to 70 mg and 50 to 60 mg, of an anti-TNFα antibody, such as adalimumab or a biosimilar thereof. In one embodiment, the treatment phase comprises administering 20, 40, 50, 60, 70, 80, 90, 100, 110, 120 or 160 mg of an anti-TNFα antibody, such as adalimumab or a biosimilar thereof.

In one embodiment the treatment dose is administered for a fixed period of time, e.g. administered at the specified dosing regiment for a period of 12 weeks, 18 weeks, 24 weeks, 30 weeks or 36 weeks.

In one embodiment the first treatment dose is administered for a fixed period of time prior to administration of the second treatment dose, e.g. the first treatment dose administered at the specified dosing regiment for a period of 12 weeks, 18 weeks, 24 weeks, 30 weeks or 36 weeks prior to administration of the second treatment dose.

In one embodiment of the invention, the induction phase comprises a first induction dose of 200 mg, and the treatment dose is 20, 40, 50, 60, 70, 80, 90, 100, 110, 120 or 160 mg. In one embodiment of the invention, the induction phase comprises a first induction dose of 210 mg, and the treatment dose is 20, 40, 50, 60, 70, 80, 90, 100, 110, 120 or 160 mg. In one embodiment of the invention, the induction phase comprises a first induction dose of 220 mg, and the treatment dose is 20, 40, 50, 60, 70, 80, 90, 100, 110, 120 or 160 mg. In one embodiment of the invention, the induction phase comprises a first induction dose of 230 mg, and the treatment dose is 20, 40, 50, 60, 70, 80, 90, 100, 110, 120 or 160 mg. In another embodiment, the first induction dose is 240 mg, and the treatment dose is 20, 40, 50, 60, 70, 80, 90, 100, 110, 120 or 160 mg. In yet another embodiment, the first induction dose is 280 mg, and the treatment dose is 20, 40, 50, 60, 70, 80, 90, 100, 110, 120 or 160 mg. In yet another embodiment, the first induction dose is 320 mg, and the treatment dose is 20, 40, 50, 60, 70, 80, 90, 100, 110, 120 or 160 mg.

In one embodiment said treatment dose is administered 5, 6, 7, 8, 9, 10, 11, 12, 13 or 14 days after said first induction dose. In one embodiment, said treatment dose is administered 7 days after said first induction dose, i.e. a week apart. In one embodiment said treatment dose is administered 5, 6, 7, 8, 9, 10, 11, 12, 13 or 14 days after said second induction dose In one embodiment, said treatment dose is administered 7 days after said second induction dose, i.e. a week apart.

In one embodiment said treatment dose is administered on a biweekly dosing regimen. In one embodiment said treatment dose is administered on a monthly dosing regimen.

In one embodiment of the invention, the induction phase comprises a first induction dose of 200 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 200 mg of an anti-TNFα antibody, such as adalimumab or a biosimilar thereof, a second induction dose 80 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 200 mg of an anti-TNFα antibody, such as adalimumab or a biosimilar thereof, a second induction dose 90 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 200 mg of an anti-TNFα antibody, such as adalimumab or a biosimilar thereof, a second induction dose 100 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof In one embodiment of the invention, the induction phase comprises a first induction dose of 200 mg of an anti-TNFα antibody, such as adalimumab or a biosimilar thereof, a second induction dose 110 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 200 mg of an anti-TNFα antibody, such as adalimumab or a biosimilar thereof, a second induction dose 120 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 200 mg of an anti-TNFα antibody, such as adalimumab or a biosimilar thereof, a second induction dose 130 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 200 mg of an anti-TNFα antibody, such as adalimumab or a biosimilar thereof, a second induction dose 140 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 200 mg of an anti-TNFα antibody, such as adalimumab or a biosimilar thereof, a second induction dose 150 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 200 mg of an anti-TNFα antibody, such as adalimumab or a biosimilar thereof, a second induction dose 160 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof.

In one embodiment of the invention, the induction phase comprises a first induction dose of 210 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 210 mg of an anti-TNFα antibody, such as adalimumab or a biosimilar thereof, a second induction dose 80 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 210 mg of an anti-TNFα antibody, such as adalimumab or a biosimilar thereof, a second induction dose 90 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 210 mg of an anti-TNFα antibody, such as adalimumab or a biosimilar thereof, a second induction dose 100 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof In one embodiment of the invention, the induction phase comprises a first induction dose of 210 mg of an anti-TNFα antibody, such as adalimumab or a biosimilar thereof, a second induction dose 110 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 210 mg of an anti-TNFα antibody, such as adalimumab or a biosimilar thereof, a second induction dose 120 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 210 mg of an anti-TNFα antibody, such as adalimumab or a biosimilar thereof, a second induction dose 130 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 210 mg of an anti-TNFα antibody, such as adalimumab or a biosimilar thereof, a second induction dose 140 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 210 mg of an anti-TNFα antibody, such as adalimumab or a biosimilar thereof, a second induction dose 150 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 210 mg of an anti-TNFα antibody, such as adalimumab or a biosimilar thereof, a second induction dose 160 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof.

In one embodiment of the invention, the induction phase comprises a first induction dose of 220 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 220 mg of an anti-TNFα antibody, such as adalimumab or a biosimilar thereof, a second induction dose 80 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 220 mg of an anti-TNFα antibody, such as adalimumab or a biosimilar thereof, a second induction dose 90 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 220 mg of an anti-TNFα antibody, such as adalimumab or a biosimilar thereof, a second induction dose 100 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof In one embodiment of the invention, the induction phase comprises a first induction dose of 220 mg of an anti-TNFα antibody, such as adalimumab or a biosimilar thereof, a second induction dose 110 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 220 mg of an anti-TNFα antibody, such as adalimumab or a biosimilar thereof, a second induction dose 120 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 220 mg of an anti-TNFα antibody, such as adalimumab or a biosimilar thereof, a second induction dose 130 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 220 mg of an anti-TNFα antibody, such as adalimumab or a biosimilar thereof, a second induction dose 140 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 220 mg of an anti-TNFα antibody, such as adalimumab or a biosimilar thereof, a second induction dose 150 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 220 mg of an anti-TNFα antibody, such as adalimumab or a biosimilar thereof, a second induction dose 160 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof.

In one embodiment of the invention, the induction phase comprises a first induction dose of 230 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 230 mg of an anti-TNFα antibody, such as adalimumab or a biosimilar thereof, a second induction dose 80 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 230 mg of an anti-TNFα antibody, such as adalimumab or a biosimilar thereof, a second induction dose 90 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 230 mg of an anti-TNFα antibody, such as adalimumab or a biosimilar thereof, a second induction dose 100 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 230 mg of an anti-TNFα antibody, such as adalimumab or a biosimilar thereof, a second induction dose 110 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 230 mg of an anti-TNFα antibody, such as adalimumab or a biosimilar thereof, a second induction dose 120 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 230 mg of an anti-TNFα antibody, such as adalimumab or a biosimilar thereof, a second induction dose 130 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 230 mg of an anti-TNFα antibody, such as adalimumab or a biosimilar thereof, a second induction dose 140 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 230 mg of an anti-TNFα antibody, such as adalimumab or a biosimilar thereof, a second induction dose 150 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 230 mg of an anti-TNFα antibody, such as adalimumab or a biosimilar thereof, a second induction dose 160 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof.

In one embodiment of the invention, the induction phase comprises a first induction dose of 240 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 240 mg of an anti-TNFα antibody, such as adalimumab or a biosimilar thereof, a second induction dose 80 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 240 mg of an anti-TNFα antibody, such as adalimumab or a biosimilar thereof, a second induction dose 90 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 240 mg of an anti-TNFα antibody, such as adalimumab or a biosimilar thereof, a second induction dose 100 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof In one embodiment of the invention, the induction phase comprises a first induction dose of 240 mg of an anti-TNFα antibody, such as adalimumab or a biosimilar thereof, a second induction dose 110 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 240 mg of an anti-TNFα antibody, such as adalimumab or a biosimilar thereof, a second induction dose 120 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 240 mg of an anti-TNFα antibody, such as adalimumab or a biosimilar thereof, a second induction dose 130 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 240 mg of an anti-TNFα antibody, such as adalimumab or a biosimilar thereof, a second induction dose 140 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 240 mg of an anti-TNFα antibody, such as adalimumab or a biosimilar thereof, a second induction dose 150 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 240 mg of an anti-TNFα antibody, such as adalimumab or a biosimilar thereof, a second induction dose 160 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof.

In one embodiment of the invention, the induction phase comprises a first induction dose of 280 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 280 mg of an anti-TNFα antibody, such as adalimumab or a biosimilar thereof, a second induction dose 80 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 280 mg of an anti-TNFα antibody, such as adalimumab or a biosimilar thereof, a second induction dose 90 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 280 mg of an anti-TNFα antibody, such as adalimumab or a biosimilar thereof, a second induction dose 100 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 280 mg of an anti-TNFα antibody, such as adalimumab or a biosimilar thereof, a second induction dose 110 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 280 mg of an anti-TNFα antibody, such as adalimumab or a biosimilar thereof, a second induction dose 120 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 280 mg of an anti-TNFα antibody, such as adalimumab or a biosimilar thereof, a second induction dose 130 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 280 mg of an anti-TNFα antibody, such as adalimumab or a biosimilar thereof, a second induction dose 140 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 280 mg of an anti-TNFα antibody, such as adalimumab or a biosimilar thereof, a second induction dose 150 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 280 mg of an anti-TNFα antibody, such as adalimumab or a biosimilar thereof, a second induction dose 160 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof.

In one embodiment of the invention, the induction phase comprises a first induction dose of 320 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 320 mg of an anti-TNFα antibody, such as adalimumab or a biosimilar thereof, a second induction dose 80 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 320 mg of an anti-TNFα antibody, such as adalimumab or a biosimilar thereof, a second induction dose 90 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 320 mg of an anti-TNFα antibody, such as adalimumab or a biosimilar thereof, a second induction dose 100 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof In one embodiment of the invention, the induction phase comprises a first induction dose of 320 mg of an anti-TNFα antibody, such as adalimumab or a biosimilar thereof, a second induction dose 110 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 320 mg of an anti-TNFα antibody, such as adalimumab or a biosimilar thereof, a second induction dose 120 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 320 mg of an anti-TNFα antibody, such as adalimumab or a biosimilar thereof, a second induction dose 130 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 320 mg of an anti-TNFα antibody, such as adalimumab or a biosimilar thereof, a second induction dose 140 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 320 mg of an anti-TNFα antibody, such as adalimumab or a biosimilar thereof, a second induction dose 150 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof. In one embodiment of the invention, the induction phase comprises a first induction dose of 320 mg of an anti-TNFα antibody, such as adalimumab or a biosimilar thereof, a second induction dose 160 mg, of the anti-TNFα antibody of an anti-TNFα antibody, such as adalimumab or a biosimilar thereof and the treatment dose is 20, 40, 50, 60, 70, 80, 90, 100, 110, 120 or 160 mg of an anti-TNFα antibody, such as adalimumab or a biosimilar thereof.

The treatment of Crohn's disease or ulcerative colitis with the TNFα inhibitor (e.g. adalimumab or biosimilars thereof) may be determined by achieving mucosal healing based on Mayo endoscopic scores less than 2 or the disappearance of all ulcerations.

In one embodiment, a second treatment dose is administered subsequent to the first treatment dose, which second treatment dose is 40% to 60% of said first induction dose. In one embodiment the second treatment dose is 50% of said first induction dose.

In one embodiment the second treatment dose is administered for a fixed period of time, e.g. administered at the specified dosing regimen for a period of 12 weeks, 18 weeks, 24 weeks, 30 weeks or 36 weeks subsequent to administration of the first treatment dose.

In one embodiment the treatment regimen is for the treatment of Crohn's disease or ulcerative colitis and the first treatment dose is administered for a first period sufficient to achieve mucosal healing prior to administration of the second treatment dose.

In one embodiment of the invention, the induction phase comprises a first induction dose of 200 mg, and the treatment dose comprises a first treatment dose of 20, 40, 50, 60, 70, 80, 90, 100, 110, 120 or 160 mg and a second treatment dose which is 40% to 60% of said first induction dose. In one embodiment of the invention, the induction phase comprises a first induction dose of 210 mg, and the treatment dose comprises a first treatment dose of 20, 40, 50, 60, 70, 80, 90, 100, 110, 120 or 160 mg and a second treatment dose which is 40% to 60% of said first induction dose. In one embodiment of the invention, the induction phase comprises a first induction dose of 220 mg, and the treatment dose comprises a first treatment dose of 20, 40, 50, 60, 70, 80, 90, 100, 110, 120 or 160 mg and a second treatment dose which is 40% to 60% of said first induction dose. In one embodiment of the invention, the induction phase comprises a first induction dose of 230 mg, and the treatment dose comprises a first treatment dose of 20, 40, 50, 60, 70, 80, 90, 100, 110, 120 or 160 mg and a second treatment dose which is 40% to 60% of said first induction dose. In another embodiment, the first induction dose is 240 mg, and the treatment dose comprises a first treatment dose of 20, 40, 50, 60, 70, 80, 90, 100, 110, 120 or 160 mg and a second treatment dose which is 40% to 60% of said first induction dose. In yet another embodiment, the first induction dose is 280 mg, and the treatment dose comprises a first treatment dose of 20, 40, 50, 60, 70, 80, 90, 100, 110, 120 or 160 mg and a second treatment dose which is 40% to 60% of said first induction dose. In yet another embodiment, the first induction dose is 320 mg, the treatment dose comprises a first treatment dose of 20, 40, 50, 60, 70, 80, 90, 100, 110, 120 or 160 mg and a second treatment dose which is 40% to 60% of said first induction dose.

In one embodiment of the invention, the induction phase comprises a first induction dose of 200 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 200 mg of an anti-TNFα antibody, such as adalimumab or a biosimilar thereof, a second induction dose of 80 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 200 mg of an anti-TNFα antibody, such as adalimumab or a biosimilar thereof, a second induction dose of 90 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 200 mg of an anti-TNFα antibody, such as adalimumab or a biosimilar thereof, a second induction dose of 100 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 200 mg of an anti-TNFα antibody, such as adalimumab or a biosimilar thereof, a second induction dose of 110 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 200 mg of an anti-TNFα antibody, such as adalimumab or a biosimilar thereof, a second induction dose of 120 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 200 mg of an anti-TNFα antibody, such as adalimumab or a biosimilar thereof, a second induction dose of 130 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 200 mg of an anti-TNFα antibody, such as adalimumab or a biosimilar thereof, a second induction dose of 140 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 200 mg of an anti-TNFα antibody, such as adalimumab or a biosimilar thereof, a second induction dose of 150 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 200 mg of an anti-TNFα antibody, such as adalimumab or a biosimilar thereof, a second induction dose of 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose.

In one embodiment of the invention, the induction phase comprises a first induction dose of 210 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 210 mg of an anti-TNFα antibody, such as adalimumab or a biosimilar thereof, a second induction dose of 80 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 210 mg of an anti-TNFα antibody, such as adalimumab or a biosimilar thereof, a second induction dose of 90 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 210 mg of an anti-TNFα antibody, such as adalimumab or a biosimilar thereof, a second induction dose of 100 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 210 mg of an anti-TNFα antibody, such as adalimumab or a biosimilar thereof, a second induction dose of 110 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose.

In one embodiment of the invention, the induction phase comprises a first induction dose of 210 mg of an anti-TNFα antibody, such as adalimumab or a biosimilar thereof, a second induction dose of 120 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 210 mg of an anti-TNFα antibody, such as adalimumab or a biosimilar thereof, a second induction dose of 130 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 210 mg of an anti-TNFα antibody, such as adalimumab or a biosimilar thereof, a second induction dose of 140 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 210 mg of an anti-TNFα antibody, such as adalimumab or a biosimilar thereof, a second induction dose of 150 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 210 mg of an anti-TNFα antibody, such as adalimumab or a biosimilar thereof, a second induction dose of 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose.

In one embodiment of the invention, the induction phase comprises a first induction dose of 220 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 220 mg of an anti-TNFα antibody, such as adalimumab or a biosimilar thereof, a second induction dose of 80 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 220 mg of an anti-TNFα antibody, such as adalimumab or a biosimilar thereof, a second induction dose of 90 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 220 mg of an anti-TNFα antibody, such as adalimumab or a biosimilar thereof, a second induction dose of 100 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 220 mg of an anti-TNFα antibody, such as adalimumab or a biosimilar thereof, a second induction dose of 110 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 220 mg of an anti-TNFα antibody, such as adalimumab or a biosimilar thereof, a second induction dose of 120 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 220 mg of an anti-TNFα antibody, such as adalimumab or a biosimilar thereof, a second induction dose of 130 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 220 mg of an anti-TNFα antibody, such as adalimumab or a biosimilar thereof, a second induction dose of 140 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 220 mg of an anti-TNFα antibody, such as adalimumab or a biosimilar thereof, a second induction dose of 150 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 220 mg of an anti-TNFα antibody, such as adalimumab or a biosimilar thereof, a second induction dose of 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose.

In one embodiment of the invention, the induction phase comprises a first induction dose of 230 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 230 mg of an anti-TNFα antibody, such as adalimumab or a biosimilar thereof, a second induction dose of 80 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 230 mg of an anti-TNFα antibody, such as adalimumab or a biosimilar thereof, a second induction dose of 90 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 230 mg of an anti-TNFα antibody, such as adalimumab or a biosimilar thereof, a second induction dose of 100 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 230 mg of an anti-TNFα antibody, such as adalimumab or a biosimilar thereof, a second induction dose of 110 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 230 mg of an anti-TNFα antibody, such as adalimumab or a biosimilar thereof, a second induction dose of 120 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 230 mg of an anti-TNFα antibody, such as adalimumab or a biosimilar thereof, a second induction dose of 130 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 230 mg of an anti-TNFα antibody, such as adalimumab or a biosimilar thereof, a second induction dose of 140 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 230 mg of an anti-TNFα antibody, such as adalimumab or a biosimilar thereof, a second induction dose of 150 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 230 mg of an anti-TNFα antibody, such as adalimumab or a biosimilar thereof, a second induction dose of 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose.

In one embodiment of the invention, the induction phase comprises a first induction dose of 240 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 240 mg of an anti-TNFα antibody, such as adalimumab or a biosimilar thereof, a second induction dose of 80 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 240 mg of an anti-TNFα antibody, such as adalimumab or a biosimilar thereof, a second induction dose of 90 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 240 mg of an anti-TNFα antibody, such as adalimumab or a biosimilar thereof, a second induction dose of 100 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 240 mg of an anti-TNFα antibody, such as adalimumab or a biosimilar thereof, a second induction dose of 110 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 240 mg of an anti-TNFα antibody, such as adalimumab or a biosimilar thereof, a second induction dose of 120 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 240 mg of an anti-TNFα antibody, such as adalimumab or a biosimilar thereof, a second induction dose of 130 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 240 mg of an anti-TNFα antibody, such as adalimumab or a biosimilar thereof, a second induction dose of 140 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 240 mg of an anti-TNFα antibody, such as adalimumab or a biosimilar thereof, a second induction dose of 150 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 240 mg of an anti-TNFα antibody, such as adalimumab or a biosimilar thereof, a second induction dose of 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose.

In one embodiment of the invention, the induction phase comprises a first induction dose of 280 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 280 mg of an anti-TNFα antibody, such as adalimumab or a biosimilar thereof, a second induction dose of 80 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 280 mg of an anti-TNFα antibody, such as adalimumab or a biosimilar thereof, a second induction dose of 90 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 280 mg of an anti-TNFα antibody, such as adalimumab or a biosimilar thereof, a second induction dose of 100 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 280 mg of an anti-TNFα antibody, such as adalimumab or a biosimilar thereof, a second induction dose of 110 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 280 mg of an anti-TNFα antibody, such as adalimumab or a biosimilar thereof, a second induction dose of 120 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 280 mg of an anti-TNFα antibody, such as adalimumab or a biosimilar thereof, a second induction dose of 130 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 280 mg of an anti-TNFα antibody, such as adalimumab or a biosimilar thereof, a second induction dose of 140 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 280 mg of an anti-TNFα antibody, such as adalimumab or a biosimilar thereof, a second induction dose of 150 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 280 mg of an anti-TNFα antibody, such as adalimumab or a biosimilar thereof, a second induction dose of 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose.

In one embodiment of the invention, the induction phase comprises a first induction dose of 320 mg of an anti-TNFα antibody, such as adalimumab or a biosimilar thereof, a second induction dose of 80 mg, 90 mg, 100 mg, 110 mg, 120 mg, 130 mg, 140 mg, 150 mg or 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 320 mg of an anti-TNFα antibody, such as adalimumab or a biosimilar thereof, a second induction dose of 80 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 320 mg of an anti-TNFα antibody, such as adalimumab or a biosimilar thereof, a second induction dose of 90 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 320 mg of an anti-TNFα antibody, such as adalimumab or a biosimilar thereof, a second induction dose of 100 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 320 mg of an anti-TNFα antibody, such as adalimumab or a biosimilar thereof, a second induction dose of 110 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 320 mg of an anti-TNFα antibody, such as adalimumab or a biosimilar thereof, a second induction dose of 120 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 320 mg of an anti-TNFα antibody, such as adalimumab or a biosimilar thereof, a second induction dose of 130 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 320 mg of an anti-TNFα antibody, such as adalimumab or a biosimilar thereof, a second induction dose of 140 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 320 mg of an anti-TNFα antibody, such as adalimumab or a biosimilar thereof, a second induction dose of 150 mg, of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose. In one embodiment of the invention, the induction phase comprises a first induction dose of 320 mg of an anti-TNFα antibody, such as adalimumab or a biosimilar thereof, a second induction dose of 160 mg of the anti-TNFα antibody of an anti-TNFα antibody, such as adalimumab or a biosimilar thereof and the treatment dose comprises a first treatment dose of 20, 40, 50, 60, 70, 80, 90, 100, 110, 120 or 160 mg of an anti-TNFα antibody, such as adalimumab or a biosimilar thereof and a second treatment dose of an anti-TNFα antibody, such as adalimumab or a biosimilar thereof which is 40% to 60% of said first induction dose.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Dose amounts described herein may be delivered as a single dose, or alternatively may be delivered as multiple doses (e.g., four 40 mg doses or two 80 mg doses for delivery of a 160 mg dose).

Where the dose is administered using a formulation that includes a concentration 50 mg/ml of the an anti-TNFα antibody, such as adalimumab or a biosimilar thereof dose amounts described herein may be delivered as a single dose (e.g., a single 20 mg dose of 20 mg in 0.4 mL; a single 40 mg dose of 40 mg in 0.8 mL; a single 50 mg dose of 50 mg in 1.0 mL a single 80 mg dose of 80 mg in 1.2 mL), or, alternatively may be delivered as multiple doses (e.g., an 80 mg dose as two×40 mg doses of 40 mg in 0.8 mL; a 100 mg dose as 2×50 mg doses of 50 mg in 1.0 mL, a 150 mg dose as 3×50 mg doses of 50 mg in 1.0 mL, a 160 mg dose as four×40 mg doses of 40 mg in 0.8 mL; a 200 mg dose as five×40 mg doses of 40 mg in 0.8 mL; a 200 mg dose as 4×50 mg doses of 50 mg in 1.0 mL, a 240 mg dose as six×40 mg doses of 40 mg in 0.8 mL; a 250 mg dose as 5×50 mg doses of 50 mg in 1.0 mL, a 280 mg dose as 7×40 mg doses of 40 mg in 0.8 mL; a 300 mg dose as 6×50 mg doses of 50 mg in 1.0 mL, or a 360 mg dose as eight×40 mg doses of 40 mg in 0.8 mL).

Where the dose is administered using a high concentration formulation that includes a concentration 100 mg/ml of the an anti-TNFα antibody, such as adalimumab or a biosimilar thereof dose amounts described herein may be delivered as a single dose (e.g., a single 20 mg dose of 20 mg in 0.2 mL; a single 40 mg dose of 40 mg in 0.4 mL; a 50 mg dose as 1×50 mg doses of 50 mg in 0.5 mL a single 80 mg dose of 80 mg in 0.8 mL, a 100 mg dose as 1×100 mg doses of 100 mg in 1.0 mL), or, alternatively may be delivered as multiple doses (e.g., a 160 mg dose as two×80 mg doses of 80 mg in 0.8 mL; a 180 mg dose as as 2×90 mg doses of 90 mg in 0.9 mL; a 200 mg dose as 2×100 mg doses of 100 mg in 1.0 mL, a 240 mg dose as three×80 mg doses of 80 mg in 0.8 mL; a 300 mg dose as 3×100 mg doses of 100 mg in 1.0 mL or a 360 mg dose as four×80 mg doses of 80 mg in 0.8 mL).

In one embodiment, the multiple variable dose methods of the invention are used to treat Crohn's disease or ulcerative colitis. The anti-TNF alpha antibody, or antigen-binding portion thereof, (e.g. adalimumab), may be administered to a human subject according to a dosing scheme and dose amount effective for treating Crohn's disease or ulcerative colitis.

In one embodiment, a first induction dose of 161, 170, 180, 190, 200, 210, 220, 230, 240, 250, 260, 270, 280, 290, 300, 310 or 320 mg of adalimumab or a biosimilar thereof, in is administered to a human subject initially at day 1, followed by a second induction dose of 80, 90, 100, 110, 120, 130, 140, 150 or 160 mg of the antibody two weeks later, followed by administration of a treatment does of 20, 40, 50, 60, 70, 80, 90, 100, 110, 120 or 160 mg every other week for the treatment of Crohn's disease or ulcerative colitis. In one embodiment, the formulation is administered subcutaneously.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 90 mg of the antibody (e.g. 1×90 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 90 mg of the antibody (e.g. 1×90 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 210 mg of adalimumab or a biosimilar thereof (e.g 3×70 mg doses in 0.7 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 1000, 110, 120 or 160 mg every other week, for the treatment of Crohn's disease or ulcerative colitis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 90 mg of the antibody (e.g. 1×90 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 90 mg of the antibody (e.g. 1×90 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 90 mg of the antibody (e.g. 1×90 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 90 mg of the antibody (e.g. 1×90 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 280 mg of adalimumab or a biosimilar thereof (e.g. 2×140 mg doses in 1.4 ml of 100 mg/ml or. 4×70 mg doses in 0.7 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 90 mg of the antibody (e.g. 1×90 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In an alternative embodiment, the multiple variable dose methods of the invention are used to treat Crohn's disease or ulcerative colitis according to a dosing scheme comprising a first induction dose of 90, 100, 110, 120, 130, 140 or 150 mg of adalimumab or a biosimilar thereof administered to a human subject initially at day 1, followed by a second induction dose of 50, 60 or 70 mg of the antibody two weeks later, followed by administration of a treatment does of 20, 40, 50, 60, 70, 80, 90, 100, 110, 120 or 160 mg every other week for the treatment of Crohn's disease or ulcerative colitis. In one embodiment, the formulation is administered subcutaneously.

In one embodiment, a first induction dose of 90 mg of adalimumab or a biosimilar thereof (e.g. 1×90 mg doses in 0.9 ml of 100 mg/ml), is administered to a human subject initially at day 1, followed by a second induction dose of 50 mg of the antibody (e.g. 1×50 mg doses in 0.5 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 90 mg of adalimumab or a biosimilar thereof (e.g. 1×90 mg doses in 0.9 ml of 100 mg/ml), is administered to a human subject initially at day 1, followed by a second induction dose of 60 mg of the antibody (e.g. 1×60 mg doses in 0.6 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 90 mg of adalimumab or a biosimilar thereof (e.g. 1×90 mg doses in 0.9 ml of 100 mg/ml), is administered to a human subject initially at day 1, followed by a second induction dose of 70 mg of the antibody (e.g. 1×70 mg doses in 0.7 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 100 mg of adalimumab or a biosimilar thereof (e.g. 1×100 mg doses in 1 ml of 100 mg/ml), is administered to a human subject initially at day 1, followed by a second induction dose of 50 mg of the antibody (e.g. 1×50 mg doses in 0.5 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 100 mg of adalimumab or a biosimilar thereof (e.g. 1×100 mg doses in 1 ml of 100 mg/ml), is administered to a human subject initially at day 1, followed by a second induction dose of 60 mg of the antibody (e.g. 1×60 mg doses in 0.6 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 100 mg of adalimumab or a biosimilar thereof (e.g. 1×100 mg doses in 1 ml of 100 mg/ml), is administered to a human subject initially at day 1, followed by a second induction dose of 70 mg of the antibody (e.g. 1×70 mg doses in 0.7 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 110 mg of adalimumab or a biosimilar thereof (e.g. 1×110 mg doses in 1.1 ml of 100 mg/ml or 2×55 mg dose in 0.55 ml of 100 mg/ml), is administered to a human subject initially at day 1, followed by a second induction dose of 50 mg of the antibody (e.g. 1×50 mg doses in 0.5 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 110 mg of adalimumab or a biosimilar thereof (e.g. 1×110 mg doses in 1.1 ml of 100 mg/ml or 2×55 mg dose in 0.55 ml of 100 mg/ml), is administered to a human subject initially at day 1, followed by a second induction dose of 60 mg of the antibody (e.g. 1×60 mg doses in 0.6 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 110 mg of adalimumab or a biosimilar thereof (e.g. 1×110 mg doses in 1.1 ml of 100 mg/ml or 2×55 mg dose in 0.55 ml of 100 mg/ml), is administered to a human subject initially at day 1, followed by a second induction dose of 70 mg of the antibody (e.g. 1×70 mg doses in 0.7 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 120 mg of adalimumab or a biosimilar thereof (e.g. 1×120 mg doses in 1.2 ml of 100 mg/ml or 2×60 mg dose in 0.6 ml of 100 mg/ml), is administered to a human subject initially at day 1, followed by a second induction dose of 50 mg of the antibody (e.g. 1×50 mg doses in 0.5 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 120 mg of adalimumab or a biosimilar thereof (e.g. 1×120 mg doses in 1.2 ml of 100 mg/ml or 2×60 mg dose in 0.6 ml of 100 mg/ml), is administered to a human subject initially at day 1, followed by a second induction dose of 60 mg of the antibody (e.g. 1×60 mg doses in 0.6 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 120 mg of adalimumab or a biosimilar thereof (e.g. 1×120 mg doses in 1.2 ml of 100 mg/ml or 2×60 mg dose in 0.6 ml of 100 mg/ml), is administered to a human subject initially at day 1, followed by a second induction dose of 70 mg of the antibody (e.g. 1×70 mg doses in 0.7 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 130 mg of adalimumab or a biosimilar thereof (e.g. 1×130 mg doses in 1.3 ml of 100 mg/ml or 2×65 mg dose in 0.65 ml of 100 mg/ml), is administered to a human subject initially at day 1, followed by a second induction dose of 50 mg of the antibody (e.g. 1×50 mg doses in 0.5 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 130 mg of adalimumab or a biosimilar thereof (e.g. 1×130 mg doses in 1.3 ml of 100 mg/ml or 2×65 mg dose in 0.65 ml of 100 mg/ml), is administered to a human subject initially at day 1, followed by a second induction dose of 60 mg of the antibody (e.g. 1×60 mg doses in 0.6 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 130 mg of adalimumab or a biosimilar thereof (e.g. 1×130 mg doses in 1.3 ml of 100 mg/ml or 2×65 mg dose in 0.65 ml of 100 mg/ml), is administered to a human subject initially at day 1, followed by a second induction dose of 70 mg of the antibody (e.g. 1×70 mg doses in 0.7 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 140 mg of adalimumab or a biosimilar thereof (e.g. 1×140 mg doses in 1.4 ml of 100 mg/ml or 2×70 mg dose in 0.7 ml of 100 mg/ml), is administered to a human subject initially at day 1, followed by a second induction dose of 50 mg of the antibody (e.g. 1×50 mg doses in 0.5 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 140 mg of adalimumab or a biosimilar thereof (e.g. 1×140 mg doses in 1.4 ml of 100 mg/ml or 2×70 mg dose in 0.7 ml of 100 mg/ml), is administered to a human subject initially at day 1, followed by a second induction dose of 60 mg of the antibody (e.g. 1×60 mg doses in 0.6 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 140 mg of adalimumab or a biosimilar thereof (e.g. 1×140 mg doses in 1.4 ml of 100 mg/ml or 2×70 mg dose in 0.7 ml of 100 mg/ml), is administered to a human subject initially at day 1, followed by a second induction dose of 70 mg of the antibody (e.g. 1×70 mg doses in 0.7 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 150 mg of adalimumab or a biosimilar thereof (e.g. 1×150 mg doses in 1.5 ml of 100 mg/ml, or 2×75 mg dose in 0.75 ml of 100 mg/ml, or 3×50 mg dose in 0.5 ml of 100 mg/ml), is administered to a human subject initially at day 1, followed by a second induction dose of 50 mg of the antibody (e.g. 1×50 mg doses in 0.5 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 150 mg of adalimumab or a biosimilar thereof (e.g. 1×150 mg doses in 1.5 ml of 100 mg/ml, or 2×75 mg dose in 0.75 ml of 100 mg/ml, or 3×50 mg dose in 0.5 ml of 100 mg/ml), is administered to a human subject initially at day 1, followed by a second induction dose of 60 mg of the antibody (e.g. 1×60 mg doses in 0.6 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In one embodiment, a first induction dose of 150 mg of adalimumab or a biosimilar thereof (e.g. 1×150 mg doses in 1.5 ml of 100 mg/ml, or 2×75 mg dose in 0.75 ml of 100 mg/ml, or 3×50 mg dose in 0.5 ml of 100 mg/ml), is administered to a human subject initially at day 1, followed by a second induction dose of 70 mg of the antibody (e.g. 1×70 mg doses in 0.7 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Crohn's disease or ulcerative colitis.

In a further alternative embodiment, the multiple variable dose methods of the invention are used to treat Crohn's disease or ulcerative colitis according to a dosing comprising a first induction dose of 50, 60, 70, 80, 90, 100, 120 or 140 mg of a human TNF alpha antibody, or antigen-binding portion thereof, (e.g., adalimumab), followed by a treatment dose of 20, 40, 50, 60, 70 or 80 mg of the antibody every other week starting one week after the initial dose. In one embodiment, the formulation is administered subcutaneously.

In one embodiment, a first induction dose of 50 mg of adalimumab or a biosimilar thereof (e.g. 1×50 mg dose in 0.5 ml of 100 mg/ml), is administered to a human subject initially at day 1, followed two weeks later (e.g. Day 15) by administration of a treatment does of 20, 40, 50, 60, 70 or 80 mg every other week, for the treatment of Crohn's disease or ulcerative colitis.

In one embodiment, a first induction dose of 60 mg of adalimumab or a biosimilar thereof (e.g. 1×60 mg dose in 0.6 ml of 100 mg/ml), is administered to a human subject initially at day 1, followed two weeks later (e.g. Day 15) by administration of a treatment does of 20, 40, 50, 60, 70 or 80 mg every other week, for the treatment of Crohn's disease or ulcerative colitis.

In one embodiment, a first induction dose of 70 mg of adalimumab or a biosimilar thereof (e.g. 1×70 mg dose in 0.7 ml of 100 mg/ml), is administered to a human subject initially at day 1, followed two weeks later (e.g. Day 15) by administration of a treatment does of 20, 40, 50, 60, 70 or 80 mg every other week, for the treatment of Crohn's disease or ulcerative colitis.

In one embodiment, a first induction dose of 80 mg of adalimumab or a biosimilar thereof (e.g. 1×80 mg dose in 0.8 ml of 100 mg/ml), is administered to a human subject initially at day 1, followed two weeks later (e.g. Day 15) by administration of a treatment does of 20, 40, 50, 60, 70 or 80 mg every other week, for the treatment of Crohn's disease or ulcerative colitis.

In one embodiment, a first induction dose of 90 mg of adalimumab or a biosimilar thereof (e.g. 1×90 mg dose in 0.9 ml of 100 mg/ml), is administered to a human subject initially at day 1, followed two weeks later (e.g. Day 15) by administration of a treatment does of 20, 40, 50, 60, 70 or 80 mg every other week, for the treatment of Crohn's disease or ulcerative colitis.

In one embodiment, a first induction dose of 100 mg of adalimumab or a biosimilar thereof (e.g. 1×100 mg dose in 1.0 ml of 100 mg/ml), is administered to a human subject initially at day 1, followed two weeks later (e.g. Day 15) by administration of a treatment does of 20, 40, 50, 60, 70 or 80 mg every other week, for the treatment of Crohn's disease or ulcerative colitis.

In one embodiment, a first induction dose of 120 mg of adalimumab or a biosimilar thereof (e.g. 1×120 mg dose in 1.2 ml of 100 mg/ml or 2×60 mg dose in 0.6 ml of 100 mg/ml), is administered to a human subject initially at day 1, followed two weeks later (e.g. Day 15) by administration of a treatment does of 20, 40, 50, 60, 70 or 80 mg every other week, for the treatment of Crohn's disease or ulcerative colitis.

In one embodiment, a first induction dose of 140 mg of adalimumab or a biosimilar thereof (e.g. 1×140 mg dose in 1.4 ml of 100 mg/ml or 2×70 mg dose in 0.7 ml of 100 mg/ml), is administered to a human subject initially at day 1, followed two weeks later (e.g. Day 15) by administration of a treatment does of 20, 40, 50, 60, 70 or 80 mg every other week, for the treatment of Crohn's disease or ulcerative colitis.

In one embodiment the dosage regimen is for the treatment of Crohn's disease and the treatment dose is 40 mg (e.g. 1×40 mg doses in 0.40 ml of 100 mg/ml).

In one embodiment the dosage regimen is for the treatment ulcerative colitis and the treatment dose is 50 mg (e.g. 1×50 mg doses in 0.50 ml of 100 mg/ml).

In one embodiment, the multiple variable dose methods of the invention are used to treat pediatric Crohn's disease. Pediatric patients weighing 40 kg or more may be treated using the multiple variable dose methods described above for Crohn's disease. For pediatric patients weighing less than 40 kg the anti-TNF alpha antibody, or antigen-binding portion thereof, (e.g. adalimumab), may be administered to a human subject according to a dosing scheme and dose amount effective for treating pediatric Crohn's disease. In one embodiment, a first induction dose of 90, 100, 110, 120, 130, 140, 150 or 160 mg of adalimumab or a biosimilar thereof, in is administered to a human pediatric subject initially at day 1, followed by a second induction dose of 40, 50, 60, 70, 80 mg of the antibody two weeks later, followed by administration of a treatment does of 10, 20, 30 40, 50, 60 or 80 mg every other week for the treatment of pediatric Crohn's disease. In one embodiment, the formulation is administered subcutaneously.

In one embodiment, a first induction dose of 90 mg of adalimumab or a biosimilar thereof (e.g. 1×90 mg doses in 0.9 ml of 100 mg/ml), is administered to a human subject initially at day 1, followed by a second induction dose of 40 mg of the antibody (e.g. 1×40 mg doses in 0.40 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 90 mg of adalimumab or a biosimilar thereof (e.g. 1×90 mg doses in 0.9 ml of 100 mg/ml), is administered to a human subject initially at day 1, followed by a second induction dose of 50 mg of the antibody (e.g. 1×50 mg doses in 0.50 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 90 mg of adalimumab or a biosimilar thereof (e.g. 1×90 mg doses in 0.9 ml of 100 mg/ml), is administered to a human subject initially at day 1, followed by a second induction dose of 60 mg of the antibody (e.g. 1×60 mg doses in 0.60 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 90 mg of adalimumab or a biosimilar thereof (e.g. 1×90 mg doses in 0.9 ml of 100 mg/ml), is administered to a human subject initially at day 1, followed by a second induction dose of 70 mg of the antibody (e.g. 1×70 mg doses in 0.70 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 90 mg of adalimumab or a biosimilar thereof (e.g. 1×90 mg doses in 0.9 ml of 100 mg/ml), is administered to a human subject initially at day 1, followed by a second induction dose of 80 mg of the antibody (e.g. 1×80 mg doses in 0.80 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 100 mg of adalimumab or a biosimilar thereof (e.g. 1×100 mg doses in 1 ml of 100 mg/ml), is administered to a human subject initially at day 1, followed by a second induction dose of 40 mg of the antibody (e.g. 1×40 mg doses in 0.40 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 100 mg of adalimumab or a biosimilar thereof (e.g. 1×100 mg doses in 1 ml of 100 mg/ml), is administered to a human subject initially at day 1, followed by a second induction dose of 50 mg of the antibody (e.g. 1×50 mg doses in 0.50 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 100 mg of adalimumab or a biosimilar thereof (e.g. 1×100 mg doses in 1 ml of 100 mg/ml), is administered to a human subject initially at day 1, followed by a second induction dose of 60 mg of the antibody (e.g. 1×60 mg doses in 0.60 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 100 mg of adalimumab or a biosimilar thereof (e.g. 1×100 mg doses in 1 ml of 100 mg/ml), is administered to a human subject initially at day 1, followed by a second induction dose of 70 mg of the antibody (e.g. 1×70 mg doses in 0.70 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 100 mg of adalimumab or a biosimilar thereof (e.g. 1×100 mg doses in 1 ml of 100 mg/ml), is administered to a human subject initially at day 1, followed by a second induction dose of 80 mg of the antibody (e.g. 1×80 mg doses in 0.80 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 110 mg of adalimumab or a biosimilar thereof (e.g. 1×110 mg doses in 1.1 ml of 100 mg/ml or 2×55 mg dose in 0.55 ml of 100 mg/ml), is administered to a human subject initially at day 1, followed by a second induction dose of 40 mg of the antibody (e.g. 1×40 mg doses in 0.40 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 110 mg of adalimumab or a biosimilar thereof (e.g. 1×110 mg doses in 1.1 ml of 100 mg/ml or 2×55 mg dose in 0.55 ml of 100 mg/ml), is administered to a human subject initially at day 1, followed by a second induction dose of 50 mg of the antibody (e.g. 1×50 mg doses in 0.50 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 110 mg of adalimumab or a biosimilar thereof (e.g. 1×110 mg doses in 1.1 ml of 100 mg/ml or 2×55 mg dose in 0.55 ml of 100 mg/ml), is administered to a human subject initially at day 1, followed by a second induction dose of 60 mg of the antibody (e.g. 1×60 mg doses in 0.60 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 110 mg of adalimumab or a biosimilar thereof (e.g. 1×110 mg doses in 1.1 ml of 100 mg/ml or 2×55 mg dose in 0.55 ml of 100 mg/ml), is administered to a human subject initially at day 1, followed by a second induction dose of 70 mg of the antibody (e.g. 1×70 mg doses in 0.70 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 110 mg of adalimumab or a biosimilar thereof (e.g. 1×110 mg doses in 1.1 ml of 100 mg/ml or 2×55 mg dose in 0.55 ml of 100 mg/ml), is administered to a human subject initially at day 1, followed by a second induction dose of 80 mg of the antibody (e.g. 1×80 mg doses in 0.80 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 120 mg of adalimumab or a biosimilar thereof (e.g. 2×60 mg dose in 0.6 ml of 100 mg/ml), is administered to a human subject initially at day 1, followed by a second induction dose of 40 mg of the antibody (e.g. 1×40 mg doses in 0.40 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 120 mg of adalimumab or a biosimilar thereof (e.g. 2×60 mg dose in 0.6 ml of 100 mg/ml), is administered to a human subject initially at day 1, followed by a second induction dose of 50 mg of the antibody (e.g. 1×50 mg doses in 0.50 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 120 mg of adalimumab or a biosimilar thereof (e.g. 2×60 mg dose in 0.6 ml of 100 mg/ml), is administered to a human subject initially at day 1, followed by a second induction dose of 60 mg of the antibody (e.g. 1×60 mg doses in 0.60 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 120 mg of adalimumab or a biosimilar thereof (e.g. 2×60 mg dose in 0.6 ml of 100 mg/ml), is administered to a human subject initially at day 1, followed by a second induction dose of 70 mg of the antibody (e.g. 1×70 mg doses in 0.70 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 120 mg of adalimumab or a biosimilar thereof (e.g. 2×60 mg dose in 0.6 ml of 100 mg/ml), is administered to a human subject initially at day 1, followed by a second induction dose of 80 mg of the antibody (e.g. 1×80 mg doses in 0.80 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 130 mg of adalimumab or a biosimilar thereof (e.g. 2×65 mg dose in 0.65 ml of 100 mg/ml), is administered to a human subject initially at day 1, followed by a second induction dose of 40 mg of the antibody (e.g. 1×40 mg doses in 0.40 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 130 mg of adalimumab or a biosimilar thereof (e.g. 2×65 mg dose in 0.65 ml of 100 mg/ml), is administered to a human subject initially at day 1, followed by a second induction dose of 50 mg of the antibody (e.g. 1×50 mg doses in 0.50 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 130 mg of adalimumab or a biosimilar thereof (e.g. 2×65 mg dose in 0.65 ml of 100 mg/ml), is administered to a human subject initially at day 1, followed by a second induction dose of 60 mg of the antibody (e.g. 1×60 mg doses in 0.60 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 130 mg of adalimumab or a biosimilar thereof (e.g. 2×65 mg dose in 0.65 ml of 100 mg/ml), is administered to a human subject initially at day 1, followed by a second induction dose of 70 mg of the antibody (e.g. 1×70 mg doses in 0.70 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 130 mg of adalimumab or a biosimilar thereof (e.g. 2×65 mg dose in 0.65 ml of 100 mg/ml), is administered to a human subject initially at day 1, followed by a second induction dose of 80 mg of the antibody (e.g. 1×80 mg doses in 0.80 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 140 mg of adalimumab or a biosimilar thereof (e.g. 2×70 mg dose in 0.7 ml of 100 mg/ml), is administered to a human subject initially at day 1, followed by a second induction dose of 40 mg of the antibody (e.g. 1×40 mg doses in 0.40 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 140 mg of adalimumab or a biosimilar thereof (e.g. 2×70 mg dose in 0.7 ml of 100 mg/ml), is administered to a human subject initially at day 1, followed by a second induction dose of 50 mg of the antibody (e.g. 1×50 mg doses in 0.50 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 140 mg of adalimumab or a biosimilar thereof (e.g. 2×70 mg dose in 0.7 ml of 100 mg/ml), is administered to a human subject initially at day 1, followed by a second induction dose of 60 mg of the antibody (e.g. 1×60 mg doses in 0.60 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 140 mg of adalimumab or a biosimilar thereof (e.g. 2×70 mg dose in 0.7 ml of 100 mg/ml), is administered to a human subject initially at day 1, followed by a second induction dose of 70 mg of the antibody (e.g. 1×70 mg doses in 0.70 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment, a first induction dose of 140 mg of adalimumab or a biosimilar thereof (e.g. 2×70 mg dose in 0.7 ml of 100 mg/ml), is administered to a human subject initially at day 1, followed by a second induction dose of 80 mg of the antibody (e.g. 1×80 mg doses in 0.80 ml of 100 mg/ml) two weeks later (e.g. Day 15), followed two weeks later (e.g. Day 29) by administration of a treatment does of 10, 20, 30 40, 50, 60 or 80 mg every other week, for the treatment of pediatric Crohn's disease.

In one embodiment the treatment dose for pediatric Crohn's disease is 20 mg (e.g. 1×20 mg doses in 0.20 ml of 100 mg/ml).

In one embodiment, the multiple variable dose methods of the invention are used to treat psoriasis. The anti-TNF alpha antibody, or antigen-binding portion thereof, (e.g., adalimumab), may be administered to a human subject according to a dosing scheme and dose amount effective for treating psoriasis. In one embodiment, a first induction dose of 90, 100, 110, 120, 130, 140, 150 or 160 mg of a human TNF alpha antibody, or antigen-binding portion thereof, (e.g., adalimumab) is administered to a human subject, followed by a treatment dose of 20, 40, 50, 60, 70 or 80 mg of the antibody every other week starting one week after the initial dose. In one embodiment, the formulation is administered subcutaneously.

In one embodiment, a first induction dose of 90 mg of adalimumab or a biosimilar thereof (e.g. 1×90 mg dose in 0.9 ml of 100 mg/ml), is administered to a human subject initially at day 1, followed two weeks later (e.g. Day 15) by administration of a treatment does of 20, 40, 50, 60, 70 or 80 mg every other week, for the treatment of psoriasis.

In one embodiment, a first induction dose of 100 mg of adalimumab or a biosimilar thereof (e.g. 1×100 mg dose in 1.0 ml of 100 mg/ml), is administered to a human subject initially at day 1, followed two weeks later (e.g. Day 15) by administration of a treatment does of 20, 40, 50, 60, 70 or 80 mg every other week, for the treatment of psoriasis.

In one embodiment, a first induction dose of 110 mg of adalimumab or a biosimilar thereof (e.g. 1×110 mg dose in 1.0 ml of 100 mg/ml or 2×55 mg dose in 0.55 ml of 100 mg/ml), is administered to a human subject initially at day 1, followed two weeks later (e.g. Day 15) by administration of a treatment does of 20, 40, 50, 60, 70 or 80 mg every other week, for the treatment of psoriasis.

In one embodiment, a first induction dose of 120 mg of adalimumab or a biosimilar thereof (e.g. 1×120 mg dose in 1.0 ml of 100 mg/ml or 2×60 mg dose in 0.60 ml of 100 mg/ml), is administered to a human subject initially at day 1, followed two weeks later (e.g. Day 15) by administration of a treatment does of 20, 40, 50, 60, 70 or 80 mg every other week, for the treatment of psoriasis.

In one embodiment, a first induction dose of 130 mg of adalimumab or a biosimilar thereof (e.g. 1×130 mg dose in 1.0 ml of 100 mg/ml or 2×65 mg dose in 0.65 ml of 100 mg/ml), is administered to a human subject initially at day 1, followed two weeks later (e.g. Day 15) by administration of a treatment does of 20, 40, 50, 60, 70 or 80 mg every other week, for the treatment of psoriasis.

In one embodiment, a first induction dose of 140 mg of adalimumab or a biosimilar thereof (e.g. 2×70 mg dose in 0.70 ml of 100 mg/ml), is administered to a human subject initially at day 1, followed two weeks later (e.g. Day 15) by administration of a treatment does of 20, 40, 50, 60, 70 or 80 mg every other week, for the treatment of psoriasis.

In one embodiment, a first induction dose of 150 mg of adalimumab or a biosimilar thereof (e.g. 2×75 mg dose in 0.75 ml of 100 mg/ml), is administered to a human subject initially at day 1, followed two weeks later (e.g. Day 15) by administration of a treatment does of 20, 40, 50, 60, 70 or 80 mg every other week, for the treatment of psoriasis.

In one embodiment, a first induction dose of 160 mg of adalimumab or a biosimilar thereof (e.g. 2×80 mg dose in 0.80 ml of 100 mg/ml), is administered to a human subject initially at day 1, followed two weeks later (e.g. Day 15) by administration of a treatment does of 20, 40, 50, 60, 70 or 80 mg every other week, for the treatment of psoriasis.

In one embodiment the treatment dose for psoriasis is 40 mg (e.g. 1×40 mg doses in 0.40 ml of 100 mg/ml).

In an alternative embodiment the multiple variable dose methods of the invention are used to treat psoriasis according to a dosing scheme comprising a first induction dose of 161, 170, 180, 190, 200, 210, 220, 230, 240, 250, 260, 270, 280, 290, 300, 310 or 320 mg of adalimumab or a biosimilar thereof, administered to a human subject initially at day 1, followed by a second induction dose of 80, 90, 100, 110, 120, 130, 140, 150 or 160 mg of the antibody two weeks later, followed by administration of a treatment does of 20, 40, 50, 60, 70, 80, 90, 100, 110, 120 or 160 mg every other week for the treatment of Psoriasis. In one embodiment, the formulation is administered subcutaneously.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 90 mg of the antibody (e.g. 1×90 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 210 mg of adalimumab or a biosimilar thereof (e.g 3×70 mg doses in 0.7 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 1000, 110, 120 or 160 mg every other week, for the treatment of Psoriasis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 90 mg of the antibody (e.g. 1×90 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 280 mg of adalimumab or a biosimilar thereof (e.g. 2×140 mg doses in 1.4 ml of 100 mg/ml or. 4×70 mg doses in 0.7 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Psoriasis.

In one embodiment, the multiple variable dose methods of the invention are used to treat uveitis. The anti-TNF alpha antibody, or antigen-binding portion thereof, (e.g., adalimumab), may be administered to a human subject according to a dosing scheme and dose amount effective for treating psoriasis. In one embodiment, a first induction dose of 90, 100, 110, 120, 130, 140, 150 or 160 mg of a human TNF alpha antibody, or antigen-binding portion thereof, (e.g., adalimumab) is administered to a human subject, followed by a treatment dose of of 20, 40, 50, 60, 70 or 80 mg of the antibody every other week starting one week after the initial dose. In one embodiment, the formulation is administered subcutaneously.

In one embodiment, a first induction dose of 90 mg of adalimumab or a biosimilar thereof (e.g. 1×90 mg dose in 0.9 ml of 100 mg/ml), is administered to a human subject initially at day 1, followed two weeks later (e.g. Day 15) by administration of a treatment does of 20, 40, 50, 60, 70 or 80 mg every other week, for the treatment of uveitis.

In one embodiment, a first induction dose of 100 mg of adalimumab or a biosimilar thereof (e.g. 1×100 mg dose in 1.0 ml of 100 mg/ml), is administered to a human subject initially at day 1, followed two weeks later (e.g. Day 15) by administration of a treatment does of 20, 40, 50, 60, 70 or 80 mg every other week, for the treatment of uveitis.

In one embodiment, a first induction dose of 110 mg of adalimumab or a biosimilar thereof (e.g. 1×110 mg dose in 1.0 ml of 100 mg/ml or 2×55 mg dose in 0.55 ml of 100 mg/ml), is administered to a human subject initially at day 1, followed two weeks later (e.g. Day 15) by administration of a treatment does of 20, 40, 50, 60, 70 or 80 mg every other week, for the treatment of uveitis.

In one embodiment, a first induction dose of 120 mg of adalimumab or a biosimilar thereof (e.g. 1×120 mg dose in 1.0 ml of 100 mg/ml or 2×60 mg dose in 0.60 ml of 100 mg/ml), is administered to a human subject initially at day 1, followed two weeks later (e.g. Day 15) by administration of a treatment does of 20, 40, 50, 60, 70 or 80 mg every other week, for the treatment of uveitis.

In one embodiment, a first induction dose of 130 mg of adalimumab or a biosimilar thereof (e.g. 1×130 mg dose in 1.0 ml of 100 mg/ml or 2×65 mg dose in 0.65 ml of 100 mg/ml), is administered to a human subject initially at day 1, followed two weeks later (e.g. Day 15) by administration of a treatment does of 20, 40, 50, 60, 70 or 80 mg every other week, for the treatment of uveitis.

In one embodiment, a first induction dose of 140 mg of adalimumab or a biosimilar thereof (e.g. 2×70 mg dose in 0.70 ml of 100 mg/ml), is administered to a human subject initially at day 1, followed two weeks later (e.g. Day 15) by administration of a treatment does of 20, 40, 50, 60, 70 or 80 mg every other week, for the treatment of uveitis.

In one embodiment, a first induction dose of 150 mg of adalimumab or a biosimilar thereof (e.g. 2×75 mg dose in 0.75 ml of 100 mg/ml), is administered to a human subject initially at day 1, followed two weeks later (e.g. Day 15) by administration of a treatment does of 20, 40, 50, 60, 70 or 80 mg every other week, for the treatment of uveitis.

In one embodiment, a first induction dose of 160 mg of adalimumab or a biosimilar thereof (e.g. 2×80 mg dose in 0.80 ml of 100 mg/ml), is administered to a human subject initially at day 1, followed two weeks later (e.g. Day 15) by administration of a treatment does of 20, 40, 50, 60, 70 or 80 mg every other week, for the treatment of uveitis.

In one embodiment the treatment dose for uveitis is 40 mg (e.g. 1×40 mg doses in 0.40 ml of 100 mg/ml).

In one embodiment, the multiple variable dose methods of the invention are used to treat Chronic Pouchitis or Behcet's Disease. The anti-TNF alpha antibody, or antigen-binding portion thereof, (e.g. adalimumab), may be administered to a human subject according to a dosing scheme and dose amount effective for treating Chronic Pouchitis or Behcet's Disease. In one embodiment, a first induction dose of 170, 180, 190, 200, 210, 220, 230, 240, 250, 260, 270, 280, 290, 300, 310 or 320 mg of adalimumab or a biosimilar thereof, in is administered to a human subject initially at day 1, followed by a second induction dose of 80, 90, 100, 110, 120, 130, 140, 150 or 160 mg of the antibody two weeks later, followed by administration of a treatment does of 20, 40, 50, 60, 70, 80, 90, 100, 110, 120 or 160 mg every other week for the treatment of Chronic Pouchitis or Behcet's Disease. In one embodiment, the formulation is administered subcutaneously.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 210 mg of adalimumab or a biosimilar thereof (e.g 3×70 mg doses in 0.7 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g.

Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 280 mg of adalimumab or a biosimilar thereof (e.g. 2×140 mg doses in 1.4 ml of 100 mg/ml or. 4×70 mg doses in 0.7 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Chronic Pouchitis or Behcet's Disease.

In one embodiment the dosage regimen is for the treatment of Chronic Pouchitis and the treatment dose is 40 mg (e.g. 1×40 mg doses in 0.40 ml of 100 mg/ml).

In one embodiment the dosage regimen is for the treatment of Behcet's Disease and the treatment dose is 40 mg (e.g. 1×40 mg doses in 0.40 ml of 100 mg/ml).

In one embodiment, the multiple variable dose methods of the invention are used to treat Psoriatic Arthritis, Ankylosing Spondylitis, Axial Spondyloarthritis, Spondyloarthritis, Sarcoidosis, Hidradenitis Suppurativa, Giant Cell Arteritis (Temporal Arteritis) or Asthma. The anti-TNF alpha antibody, or antigen-binding portion thereof, (e.g. adalimumab), may be administered to a human subject according to a dosing scheme and dose amount effective for treating Psoriatic Arthritis, Ankylosing Spondylitis, Axial Spondyloarthritis, Spondyloarthritis, Sarcoidosis, Hidradenitis Suppurativa, Giant Cell Arteritis (Temporal Arteritis), Heart Disease or Asthma. In one embodiment, a first induction dose of 170, 180, 190, 200, 210, 220, 230, 240, 250, 260, 270, 280, 290, 300, 310 or 320 mg of adalimumab or a biosimilar thereof, in is administered to a human subject initially at day 1, followed by a second induction dose of 80, 90, 100, 110, 120, 130, 140, 150 or 160 mg of the antibody two weeks later, followed by administration of a treatment does of 20, 40, 50, 60, 70, 80, 90, 100, 110, 120 or 160 mg every other week for the treatment of Psoriatic Arthritis, Ankylosing Spondylitis, Axial Spondyloarthritis, Spondyloarthritis, Sarcoidosis, Hidradenitis Suppurativa, Giant Cell Arteritis (Temporal Arteritis), Heart Disease or Asthma. In one embodiment, the formulation is administered subcutaneously.

In one embodiment, the multiple variable dose methods of the invention are used to Psoriatic Arthritis, Ankylosing Spondylitis, Axial Spondyloarthritis, Spondyloarthritis, Sarcoidosis, Hidradenitis Suppurativa, Giant Cell Arteritis (Temporal Arteritis) or Asthma. The anti-TNF alpha antibody, or antigen-binding portion thereof, (e.g., adalimumab), may be administered to a human subject according to a dosing scheme and dose amount effective for treating Psoriatic Arthritis, Ankylosing Spondylitis, Axial Spondyloarthritis, Spondyloarthritis, Sarcoidosis, Hidradenitis Suppurativa, Giant Cell Arteritis (Temporal Arteritis), Heart Disease or Asthma. In one embodiment, a first induction dose of 90, 100, 110, 120, 130, 140, 150 or 160 mg of a human TNF alpha antibody, or antigen-binding portion thereof, (e.g., adalimumab) is administered to a human subject, followed by a treatment dose of 20, 40, 50, 60, 70 or 80 mg of the antibody every other week starting one week after the initial dose. In one embodiment, the formulation is administered subcutaneously.

In one embodiment, the multiple variable dose methods of the invention are used to treat rheumatoid arthritis. The anti-TNF alpha antibody, or antigen-binding portion thereof, (e.g., adalimumab), may be administered to a human subject according to a dosing scheme and dose amount effective for treating rheumatoid arthritis. In one embodiment, a first induction dose of 90, 100, 110, 120, 130, 140, 150 or 160 mg of a human TNF alpha antibody, or antigen-binding portion thereof, (e.g., adalimumab) is administered to a human subject, followed by a treatment dose of 20, 40, 50, 60, 70 or 80 mg of the antibody every other week starting one week after the initial dose. In one embodiment, the formulation is administered subcutaneously.

In one embodiment, a first induction dose of 90 mg of adalimumab or a biosimilar thereof (e.g. 1×90 mg dose in 0.9 ml of 100 mg/ml), is administered to a human subject initially at day 1, followed two weeks later (e.g. Day 15) by administration of a treatment does of 20, 40, 50, 60, 70 or 80 mg every other week, for the treatment of rheumatoid arthritis.

In one embodiment, a first induction dose of 100 mg of adalimumab or a biosimilar thereof (e.g. 1×100 mg dose in 1.0 ml of 100 mg/ml), is administered to a human subject initially at day 1, followed two weeks later (e.g. Day 15) by administration of a treatment does of 20, 40, 50, 60, 70 or 80 mg every other week, for the treatment of rheumatoid arthritis.

In one embodiment, a first induction dose of 110 mg of adalimumab or a biosimilar thereof (e.g. 1×110 mg dose in 1.0 ml of 100 mg/ml or 2×55 mg dose in 0.55 ml of 100 mg/ml), is administered to a human subject initially at day 1, followed two weeks later (e.g. Day 15) by administration of a treatment does of 20, 40, 50, 60, 70 or 80 mg every other week, for the treatment of rheumatoid arthritis.

In one embodiment, a first induction dose of 120 mg of adalimumab or a biosimilar thereof (e.g. 1×120 mg dose in 1.0 ml of 100 mg/ml or 2×60 mg dose in 0.60 ml of 100 mg/ml), is administered to a human subject initially at day 1, followed two weeks later (e.g. Day 15) by administration of a treatment does of 20, 40, 50, 60, 70 or 80 mg every other week, for the treatment of rheumatoid arthritis.

In one embodiment, a first induction dose of 130 mg of adalimumab or a biosimilar thereof (e.g. 1×130 mg dose in 1.0 ml of 100 mg/ml or 2×65 mg dose in 0.65 ml of 100 mg/ml), is administered to a human subject initially at day 1, followed two weeks later (e.g. Day 15) by administration of a treatment does of 20, 40, 50, 60, 70 or 80 mg every other week, for the treatment of rheumatoid arthritis.

In one embodiment, a first induction dose of 140 mg of adalimumab or a biosimilar thereof (e.g. 2×70 mg dose in 0.70 ml of 100 mg/ml), is administered to a human subject initially at day 1, followed two weeks later (e.g. Day 15) by administration of a treatment does of 20, 40, 50, 60, 70 or 80 mg every other week, for the treatment of rheumatoid arthritis.

In one embodiment, a first induction dose of 150 mg of adalimumab or a biosimilar thereof (e.g. 2×75 mg dose in 0.75 ml of 100 mg/ml), is administered to a human subject initially at day 1, followed two weeks later (e.g. Day 15) by administration of a treatment does of 20, 40, 50, 60, 70 or 80 mg every other week, for the treatment of rheumatoid arthritis.

In one embodiment, a first induction dose of 160 mg of adalimumab or a biosimilar thereof (e.g. 2×80 mg dose in 0.80 ml of 100 mg/ml), is administered to a human subject initially at day 1, followed two weeks later (e.g. Day 15) by administration of a treatment does of 20, 40, 50, 60, 70 or 80 mg every other week, for the treatment of rheumatoid arthritis.

In one embodiment the treatment dose for rheumatoid arthritis is 40 mg (e.g. 1×40 mg doses in 0.40 ml of 100 mg/ml).

In an alternative embodiment the multiple variable dose methods of the invention are used to treat rheumatoid arthritis according to a dosing scheme comprising a first induction dose of 161, 170, 180, 190, 200, 210, 220, 230, 240, 250, 260, 270, 280, 290, 300, 310 or 320 mg of adalimumab or a biosimilar thereof, administered to a human subject initially at day 1, followed by a second induction dose of 80, 90, 100, 110, 120, 130, 140, 150 or 160 mg of the antibody two weeks later, followed by administration of a treatment does of 20, 40, 50, 60, 70, 80, 90, 100, 110, 120 or 160 mg every other week for the treatment of Rheumatoid arthritis. In one embodiment, the formulation is administered subcutaneously.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 200 mg of adalimumab or a biosimilar thereof (e.g. 2×100 mg doses in 1 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 210 mg of adalimumab or a biosimilar thereof (e.g 3×70 mg doses in 0.7 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 1000, 110, 120 or 160 mg every other week, for the treatment of Rheumatoid arthritis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 210 mg of adalimumab or a biosimilar thereof (e.g. 3×70 mg doses in 0.7 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 220 mg of adalimumab or a biosimilar thereof (e.g. 2×110 mg doses in 1.1 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 230 mg of adalimumab or a biosimilar thereof (e.g. 2×115 mg doses in 1.15 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 240 mg of adalimumab or a biosimilar thereof (e.g. 3×80 mg doses in 0.8 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 90 mg of the antibody (e.g. 1×90 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 280 mg of adalimumab or a biosimilar thereof (e.g. 2×140 mg doses in 1.4 ml of 100 mg/ml or 4×70 mg doses in 0.7 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 280 mg of adalimumab or a biosimilar thereof (e.g. 2×140 mg doses in 1.4 ml of 100 mg/ml or. 4×70 mg doses in 0.7 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 80 mg of the antibody (e.g. 1×80 mg doses in 0.8 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 90 mg of the antibody (e.g. 1×890 mg doses in 0.9 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 100 mg of the antibody (e.g. 1×100 mg doses in 1 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 110 mg of the antibody (e.g. 2×55 mg doses in 0.55 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 120 mg of the antibody (e.g. 2×60 mg doses in 0.60 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 130 mg of the antibody (e.g. 2×65 mg doses in 0.65 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 140 mg of the antibody (e.g. 2×70 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 150 mg of the antibody (e.g. 2×75 mg doses in 0.70 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, a first induction dose of 320 mg of adalimumab or a biosimilar thereof (e.g. 4×80 mg doses in 0.8 ml of 100 mg/ml), is administered to a human subject initially at day 1, followed by a second induction dose of 160 mg of the antibody (e.g. 2×80 mg doses in 0.80 ml of 100 mg/ml) two weeks later (e.g. Day 15), followed two weeks later (e.g. Day 29) by administration of a treatment does of 20, 40, 50, 60, 70, 80, 90, 100, 110, 120 or 160 mg every other week, for the treatment of Rheumatoid arthritis.

In one embodiment, the multiple variable dose methods of the invention are used to treat Juvenile Idiopathic Arthritis. The anti-TNF alpha antibody, or antigen-binding portion thereof, (e.g. adalimumab), may be administered to a human subject according to a dosing scheme and dose amount effective for treating Juvenile Idiopathic Arthritis. In one embodiment, a first induction dose of 90, 100, 110, 120, 130, 140, 150 or 160 mg of adalimumab or a biosimilar thereof, in is administered to a human pediatric subject initially at day 1, followed by a second induction dose of 40, 50, 60, 70, 80 mg of the antibody two weeks later, followed by administration of a treatment does of 10, 20, 30 40, 60 or 80 mg every other week for the treatment of Juvenile Idiopathic Arthritis. In one embodiment, the formulation is administered subcutaneously.

In one embodiment, the multiple variable dose methods of the invention are used to treat Juvenile Idiopathic Arthritis. The anti-TNF alpha antibody, or antigen-binding portion thereof, (e.g. adalimumab), may be administered to a human subject according to a dosing scheme and dose amount effective for treating Juvenile Idiopathic Arthritis. In one embodiment, a first induction dose of 90, 100, 110, 120, 130, 140, 150 or 160 mg of adalimumab or a biosimilar thereof, in is administered to a human pediatric subject initially at day 1, followed two weeks later by administration of a treatment does of 10, 20, 30 40, 60 or 80 mg every other week for the treatment of Juvenile Idiopathic Arthritis. In one embodiment, the formulation is administered subcutaneously.

B. Compositions

Anti-TNFα antibodies, such as adalimumab or a biosimilar thereof, and antibody-portions thereof, for use in the multiple variable dose methods of the invention, can be incorporated into pharmaceutical compositions suitable for administration to a subject.

Typically, the pharmaceutical composition comprises an anti-TNFα antibody, such as adalimumab or a biosimilar thereof and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the anti-TNFα antibody, such as adalimumab or a biosimilar thereof.

The compositions for use in the methods of the invention may be in a variety of forms. These include, for example, liquid, semi-solid and solid dosage forms, such as liquid solutions (e. g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e. g., intravenous, subcutaneous, intraperitoneal, intramuscular). In a preferred embodiment, the anti-TNFα antibody, such as adalimumab or a biosimilar thereof, is administered by intravenous infusion or injection. In another preferred embodiment, the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e. an anti-TNFα antibody, such as adalimumab or a biosimilar thereof) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought by including in the composition an agent that delays absorption, for example, monostearate salts and gelatin.

Supplementary active compounds can also be incorporated into the compositions.

In certain embodiments, anti-TNFα antibodies, such as adalimumab or a biosimilar thereof for use in the methods of the invention are coformulated with and/or coadministered with one or more additional therapeutic agents. For example, an anti-hTNFα antibody or antibody portion of the invention may be coformulated and/or coadministered with one or more DMARD or one or more NSAID or one or more additional antibodies that bind other targets (e.g., antibodies that bind other cytokines or that bind cell surface molecules), one or more cytokines, soluble TNFα receptor (see e. g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

In one embodiment, the invention includes pharmaceutical compositions comprising an effective amount of an anti-TNFα antibody, such as adalimumab or a biosimilar thereo, and a pharmaceutically acceptable carrier, wherein the effective amount of the anit-TNFα antibody may be effective to treat a TNFα-related disorder, including, for example, Crohn's disease, in a multiple variable dose regimen.

In one embodiment, the antibody or antibody portion for use in the multiple variable dose methods of the invention is incorporated into a pharmaceutical formulation as described in PCT/IB03/04502 and U.S. application Ser. No. 10/222,140, incorporated by reference herein. This formulation includes a concentration 50 mg/ml of the antibody adalimumab, wherein one pre-filled syringe contains 40 mg of antibody for subcutaneous injection.

In one embodiment an anti-TNFα antibody, such as adalimumab or a biosimilar thereof for use in the multiple variable dose methods of the invention is adalimumab and provided in the form of the commercial adalimumab formulation described in US20060153846, and the formulation described in US20100278822, each of which is incorporated by reference herein.

In one embodiment an anti-TNFα antibody, such as adalimumab or a biosimilar thereof for use in the multiple variable dose methods of the invention is incorporated into is formulated as a high-concentration formulations. Such formulations of provide a number of surprising characteristics given the high concentration of the therapeutic antibody. Specifically, the pharmaceutical formulations comprising human anti-TNFα antibodies, which have improved bioavailability or decreased pain upon subcutaneous injection, as described in WO2012065072, WO2010129469 and WO2009073569, incorporated by reference herein.

In one embodiment an anti-TNFα antibody, such as adalimumab or a biosimilar thereof for use in the multiple variable dose methods of the invention is incorporated into formulations comprising a combination of only one or two excipients, i.e., a surfactant and a polyol or, alternatively, a surfactant alone. Despite having few excipients, these formulations can contain a high concentration of the antibody, e.g. 90-110 mg/ml, and are stable.

In one embodiment an anti-TNFα antibody, such as adalimumab or a biosimilar thereof for use in the multiple variable dose methods of the invention is incorporated into a formulation containing an antibody concentration of more than 50 mg/ml (e.g., 90-110 mg/ml) of anti-TNFα antibody, less than 50 mg/ml of a polyol, (such as mannitol), and a surfactant, (such as a polysorbate), and having no buffer or salt. By removing or excluding salt (e.g., NaCl) and/or a buffer (e.g., a phosphate/citrate buffer) the concentration of a human anti-TNF alpha antibody in a formulation can be increased, e.g., to 100 mg/mL, while decreasing pain upon delivery to a patient.

High-concentration formulations containing a polyol preferably contain less than 50 mg of the polyol. In one embodiment, the formulations contain less than 45 mg/mL of the polyol. In another embodiment, the high-concentration formulations contain 38-46 mg/mL of the polyol (e.g., mannitol), e.g., 35, 36, 37, 38, 39, 40, 41, 42, 43, 44, 45, 46, 47, 48, 49, 50, 51, 52, 53, 54, or 55 mg/mL of the polyol. In addition, ranges of values using a combination of any of the above recited values as upper and/or lower limits are intended to be included, e.g., 39-45 mg/ml, 40-44 mg/ml, or 37-47 mg/ml. In one embodiment, the high-concentration formulations contain 12-72 mg/ml of polyol, e.g., mannitol. In one embodiment, suitable polyols for use in the formulations and methods of the invention are mannitol or sorbitol.

In one embodiment an anti-TNFα antibody, such as adalimumab or a biosimilar thereof for use in the multiple variable dose methods of the invention is incorporated into a high concentration formulation comprising adalimumab (or a biosimilar thereof), polysorbate 80, mannitol, and water for injection. In one embodiment, the formulation contains 80 mg of adalimumab, water for injection, 42 mg/ml of mannitol, and 1 mg/ml of polysorbate 80. In one embodiment, the formulation may contain 20-110 mg, alternatively 20-90 mg of adalimumab or, alternatively, 30-80 mg of the antibody. In one embodiment, the formulation contains 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, or 110 mg of the antibody. Ranges including the aforementioned numbers are also included in the invention, e.g., 70-90 mg, 65-95, or 60-85 mg.

The high antibody concentration formulations include for example, an antibody concentration of 50 mg/mL, 55 mg/mL, 60 mg/mL. 65 mg/mL, 70 mg/mL, 75 mg/ml, 80 mg/mL, 85 mg/mL, 90 mg/mL, 95 mg/mL 100 mg/mL, 105 mg/mL, 110 mg/mL, 115 mg/mL (or higher) of a human anti-TNF-alpha antibody or antigen-binding fragment thereof. Accordingly, in one embodiment an anti-TNFα antibody, such as adalimumab or a biosimilar thereof for use in the multiple variable dose methods of the invention is incorporated into a high concentration liquid pharmaceutical formulations containing the human anti-TNF alpha antibody concentration of 50-100 mg/mL or greater. In one embodiment, the high concentration formulations may comprise an antibody concentration between 1 mg/mL-150 mg/mL or 40 mg/mL-125 mg/mL. In one embodiment, the antibody concentration of the high concentration formulation is 50-150 mg/ml, 55-150 mg/ml, 60-150 mg/ml, 65-150 mg/ml, 70-150 mg/ml, 75-150 mg/ml, 80-150 mg/ml, 85-150 mg/ml, 90-150 mg/ml, 90-110 mg/ml, 95-105 mg/ml, 95-150 mg/ml, 100-150 mg/ml, 105-150 mg/ml, 110-150 mg/ml, 115-150 mg/ml, 120-150 mg/ml, 125-150 mg/ml, 50-130 mg/ml, 75-125 mg/ml, etc. Concentrations and ranges intermediate to the above recited concentrations are also intended to be part of this invention (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 mg/mL).

An important aspect of the high concentration formulations is the omission of a buffer and salt. Thus, in one embodiment, an anti-TNFα antibody, such as adalimumab or a biosimilar thereof for use in the multiple variable dose methods of the invention is incorporated into a high concentration formulation that does not contain any buffer(s) (e.g., citrate and phosphate) and salts. It should be noted, however, that although the preferred high concentration formulations do not contain buffers or salts (e.g., NaCl), a small amount of buffer and/or salt may be present in the formulations. Thus, in one embodiment, an anti-TNFα antibody, such as adalimumab or a biosimilar thereof for use in the multiple variable dose methods of the invention is incorporated into a high concentration formulation that does not contain detectable levels of a buffer(s) and/or a salt.

In one embodiment, an anti-TNFα antibody, such as adalimumab or a biosimilar thereof for use in the multiple variable dose methods of the invention is incorporated into a high concentration formulation that contains the human anti-TNF alpha antibody, or antigen binding portion thereof, at a concentration of 100 mg/mL (or 75-125 mg/mL), a surfactant (e.g., polysorbate 80), a polyol (e.g., sorbitol or mannitol), and has a conductivity of less than 2 mS/cm. In one embodiment, the formulation contains of a human anti-TNF alpha antibody, or antigen binding portion thereof, at a concentration of 100 mg/mL (or 75-125 mg/mL), 0.8-1.3 mg/ml of a surfactant (e.g., polysorbate 80), less than 50 mg/ml of a polyol (e.g., sorbitol or mannitol), and has a conductivity of less than 2 mS/cm. In one embodiment, the formulation contains of a human anti-TNF alpha antibody, or antigen binding portion thereof, at a concentration of 100 mg/mL (or 75-125 mg/mL), a surfactant (e.g., polysorbate 80), and has a conductivity of less than 2 mS/cm. In one embodiment, the formulation contains of a human anti-TNF alpha antibody, or antigen binding portion thereof, at a concentration of 100 mg/mL (or 75-125 mg/mL), 0.8-1.3 mg/ml of a surfactant (e.g., polysorbate 80), and has a conductivity of less than 2 mS/cm.

In one embodiment, an anti-TNFα antibody, such as adalimumab or a biosimilar thereof for use in the multiple variable dose methods of the invention is incorporated into a high concentration formulation that contains the human anti-TNF alpha antibody, or antigen binding portion thereof, at a concentration of 100 mg/mL (or 75-125 mg/mL), a surfactant (e.g., polysorbate 80), a polyol (e.g., sorbitol or mannitol), and has a hydrodynamic diameter of less than 4 nm. In one embodiment, the formulation contains of a human anti-TNF alpha antibody, or antigen binding portion thereof, at a concentration of 100 mg/mL (or 75-125 mg/mL), 0.8-1.3 mg/ml of a surfactant (e.g., polysorbate 80), less than 50 mg/ml of a polyol (e.g., sorbitol or mannitol), and has a hydrodynamic diameter of less than 4 nm.

In one embodiment, an anti-TNFα antibody, such as adalimumab or a biosimilar thereof for use in the multiple variable dose methods of the invention is incorporated into a high concentration formulation that contain the human anti-TNF alpha antibody, or antigen binding portion thereof, at a concentration of 100 mg/mL (or 75-125 mg/mL), a surfactant (e.g., polysorbate 80), and has a hydrodynamic diameter of less than 4 nm. In one embodiment, the formulation contains of a human anti-TNF alpha antibody, or antigen binding portion thereof, at a concentration of 100 mg/mL (or 75-125 mg/mL), 0.8-1.3 mg/ml of a surfactant (e.g., polysorbate 80), and has a hydrodynamic diameter of less than 4 nm.

In one embodiment, an anti-TNFα antibody, such as adalimumab or a biosimilar thereof for use in the multiple variable dose methods of the invention is incorporated into a high concentration formulation that consists essentially of a human anti-TNF alpha antibody, or antigen binding portion thereof, at a concentration of 100 mg/mL (or 75-125 mg/mL), a surfactant (e.g., polysorbate 80), a polyol (e.g., sorbitol or mannitol), does not contain a buffer(s) (e.g., citric acid monohydrate, sodium citrate, disodium phosphate dihydrate, and/or sodium dihydrogen phosphate dihydrate), and does not contain a salt (e.g., NaCl).

The antibodies and antibody-portions of the present invention can be administered by a variety of methods known in the art, although for many therapeutic applications, the preferred route/mode of administration is subcutaneous injection. In another embodiment, administration is via intravenous injection or infusion.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

The TNFα antibodies of the invention can also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. application Ser. No. 10/222,140, incorporated by reference herein, are used to treat a TNFα-related disorder using the multiple-variable dose methods of the invention.

In certain embodiments, an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

The invention also pertains to packaged pharmaceutical compositions or kits for administering the multiple-variable dose regimen of the invention. In one embodiment of the invention, the kit comprises a anti-TNFα antibody (e.g. adalimumab or a biosimilar thereof), and administration instructions according to the multiple-variable dose method for treatment. In one embodiment, the kit of the invention comprises an induction dose and/or a treatment dose for treatment of a particular disorder in which TNFα activity is detrimental. The kit may also include instructions relating to administration of the induction and/or treatment doses.

The instructions may describe how, e. g., subcutaneously, and when, e. g., at week 0 and week 2, the different doses of anti TNF antibody shall be administered to a subject for treatment. The instructions may also describe the administration of the anti TNFα antibody during the induction and the treatment phases of the multiple-variable dose treatment.

Kits to be used for the methods of the invention may include individual doses of an anti-TNFα antibody which can be used in part, in whole, or in combination with one another to achieve the multiple-variable dose regimen. For example, the kit may include a number of prefilled syringes containing the anti TNFα antibody adalimumab or a biosimilar thereof, wherein each syringe contains a 170, 180, 190, 200, 210, 220, 230, 240, 250, 260, 270, 280, 290, 300, 310 or 320 mg dose of the anti TNFα antibody. A kit of the invention for the treatment of Crohn's may also include a dose or doses of methotrexate for administration in combination with adalimumab.

In another example, the kit of the invention may include doses of adalimumab or a biosimilar for multiple-variable dose treatment of Chron's Disease. In one embodiment, the kit may contain at least one induction dose of 200 mg of adalimumab, and at least one maintenance dose of 40 mg of adalimumab. Instructions for administration of adalimumab for the treatment of psoriasis may include, for example, directions for administering one 200 mg dose, a second 100 mg dose a week later, and a 40 mg dose a week later and subsequently every other week. In an alternative embodiment the instructions for administration of adalimumab may recite any one of the specific multiple-variable dose regimen disclosed herein in respect of Chron's Disease.

In another example, the kit of the invention may include doses of adalimumab or a biosimilar for multiple-variable dose treatment of psoriasis. In one embodiment, the kit may contain at least one induction dose of 200 mg of adalimumab, and at least one maintenance dose of 50 mg of adalimumab. Instructions for administration of adalimumab for the treatment of psoriasis may include, for example, directions for administering one 200 mg dose, a second 100 mg dose a week later, and a 50 mg dose a week later and subsequently every other week. In an alternative embodiment the instructions for administration of adalimumab may recite any one of the specific multiple-variable dose regimen disclosed herein in respect of psoriasis.

Alternatively, the kit comprises a single pharmaceutical composition comprising an anti-TNFα antibody, one or more drugs useful for treating a TNFα-related disorder and a pharmaceutically acceptable carrier. The kits contain instructions for dosing of the pharmaceutical compositions for the treatment of a TNFα-related disorder in which the administration of an anti-TNFα antibody is beneficial, such as Crohn's disease or psoriasis.

The package or kit alternatively can contain the TNFα inhibitor and it can be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

C. Additional Therapeutic Agents

The invention pertains to pharmaceutical compositions and methods of use thereof for the treatment of a TNFα-related disorder using a multiple-variable dose regimen. The pharmaceutical compositions comprise a first agent that prevents or inhibits a TNFα-related disorder. The pharmaceutical composition and methods of use may comprise a second agent that is an active pharmaceutical ingredient; that is, the second agent is therapeutic and its function is beyond that of an inactive ingredient, such as a pharmaceutical carrier, preservative, diluent, or buffer. The second agent may be useful in treating or preventing TNFα-related disorders. The second agent may diminish or treat at least one symptom (s) with the targeted disease. The first and second agents may exert their biological effects by similar or unrelated mechanisms of action; or either one or both of the first and second agents may exert their biological effects by a multiplicity of mechanisms of action. A pharmaceutical composition may also comprise a third compound, or even more yet, wherein the third (and fourth, etc.) compound has the same characteristics of a second agent.

It should be understood that the pharmaceutical compositions described herein may have the first and second, third, or additional agents in the same pharmaceutically acceptable carrier or in a different pharmaceutically acceptable carrier for each described embodiment. It further should be understood that the first, second, third and additional agent may be administered simultaneously or sequentially within described embodiments. Alternatively, a first and second agent may be administered simultaneously, and a third or additional agent may be administered before or after the first two agents.

The combination of agents used within the methods and pharmaceutical compositions described herein may have a therapeutic additive or synergistic effect on the condition (s) disease (s) for treatment. The combination of agents used within the methods or pharmaceutical compositions described herein also may reduce a detrimental effect associated with at least one of the agents when administered alone or without the other agent (s) particular pharmaceutical composition. For example, the toxicity of side effects of one agent may be attenuated by another agent of the composition, thus allowing a higher dosage, improving patient compliance, and improving therapeutic outcome. The additive or synergistic effects, benefits, and advantages of the compositions apply to classes of therapeutic agents, either structural or functional classes, or to individual compounds themselves.

Supplementary active compounds can also be incorporated into the compositions.

In certain embodiments, an antibody or antibody portion of the invention is coformulated with and/or coadministered with one or more additional therapeutic agents that are useful for treating TNFα-related disorder in which TNFα activity is detrimental. For example, an anti-hTNFα antibody, antibody portion, or other TNFα inhibitor of the invention may be coformulated and/or coadministered with one or more additional antibodies that bind other targets (e.g., antibodies that bind other cytokines or that bind cell surface molecules), one or more cytokines, soluble TNFα receptor (see e. g., PCT Publication No. WO 94/06476) and/or one or more chemical agents that inhibit hTNFα production or activity (such as cyclohexane-ylidene derivatives as described in PCT Publication No. WO 93/19751). Furthermore, one or more antibodies or other TNFα inhibitors of the invention may be used in combination with two or more of the foregoing therapeutic agents. Such combination therapies may advantageously utilize lower dosages of the administered therapeutic agents, thus avoiding possible toxicities or complications associated with the various monotherapies. Specific therapeutic agent(s) are generally selected based on the particular TNFα-related disorder being treated, as discussed below.

Nonlimiting examples of therapeutic agents with which an antibody, antibody portion, or other TNFα inhibitor can be combined in a multiple variable dose method of treatment of the invention include the following: non-steroidal anti-inflammatory drug(s) (NSAIDs); cytokine suppressive anti-inflammatory drug (s) (CSAIDs); CDP-571/BAY-10-3356 (humanized anti-TNFα antibody; Celltech/Bayer); cA2/infliximab (chimeric anti-TNFα antibody; Centocor); 75 kdT-NFR-IgG/etanercept (75 kD TNF receptor-IgG fusion protein; Immunex; see e.g., Arthritis & Rheumatism (1994) Vol. 37, S295; J. Invest. Med. (1996) Vol. 44, 235A); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., Arthritis & Rheumatism (1995) Vol. 38, S 185); DAB 486-IL-2 and/or DAB 389-IL-2 (IL-2 fusion proteins; Seragen; see e.g., Arthritis & Rheumatism (1993) Vol. 36, 1223); Anti-Tac (humanized anti-IL-2Ra; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e. g., agonist antibodies); IL-1 RA (IL-1 receptor antagonist; Synergen/Amgen); anakinra (Kineret@/Amgen); TNF-bp/s-TNF (soluble TNF binding protein; see e.g., Arthritis & Rheumatism (1996) Vol. 39, No. 9 (supplement), S284; Amer. J Physiol.—Heart and Circulatory Physiology (1995) Vol. 268, pp. 37-42); R973401 (phosphodiesterase Type IV inhibitor; see e.g., Arthritis & Rheumatism (1996) Vol. 39, No. 9 (supplement), S282); MK-966 (COX-2 Inhibitor; see e.g., Arthritis & Rheumatism (1996) Vol. 39, No. 9 (supplement), S81); Iloprost (see e.g., Arthritis & Rheumatism (1996) Vol. 39, No. 9 (supplement), S82); methotrexate; thalidomide (see e.g., Arthritis & Rheumatism (1996) Vol. 39, No. 9 (supplement), S282) and thalidomide-related drugs (e.g., Celgen); leflunomide (anti-inflammatory and cytokine inhibitor; see e.g., Arthritis & Rheumatism (1996) Vol. 39, No. 9 (supplement), S131; Inflammation Research (1996) Vol. 45, pp. 103-107); tranexamic acid (inhibitor of plasminogen activation; see e.g., Arthritis & Rheumatism (1996) Vol. 39 No. 9 (supplement), S284); T-614 (cytokine inhibitor; see e.g., Arthritis & Rheumatism (1996) Vol. 39, No. 9 (supplement), S282; prostaglandin El (see e.g., Arthritis & Rheumatism (1996) Vol. 39 No. 9 (supplement), S282); Tenidap (non-steroidal anti-inflammatory drug; see e.g., Arthritis & Rheumatism (1996) Vol. 39, No. 9 (supplement), S280); Naproxen (non-steroidal anti-inflammatory drug; see e. g., Neuro Report (1996) Vol. 7, pp. 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., Arthritis & Rheumatism (1996) Vol. 39, No. 9 (supplement), S281); Azathioprine (see e.g., Arthritis & Rheumatism (1996) Vol. 39, No. 9 (supplement), S281); ICE inhibitor (inhibitor of the enzyme interleukin-1 [3 converting enzyme); zap-70 and/or Ick inhibitor (inhibitor of the tyrosine kinase zap-70 or Ick); VEGF inhibitor and/or VEGF-R inhibitor (inhibitos of vascular endothelial cell growth factor or vascular endothelial cell growth factor receptor; inhibitors of angiogenesis); corticosteroid anti-inflammatory drugs (e. g., SB203580); TNF-convertase inhibitors; anti-IL-12 antibodies; anti-IL-18 antibodies; interleukin-11 (see e.g., Arthritis & Rheumatism (1996) Vol. 39, No. 9 (supplement), S296); interleukin-13 (see e.g., Arthritis & Rheumatism (1996) Vol. 39, No. 9 (supplement), S308); interleukin-17 inhibitors (see e.g., Arthritis & Rheumatism (1996) Vol. 39, No. 9 (supplement), S120); gold; penicillamine; chloroquine; hydroxychloroquine; chlorambucil; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e. g., DeLuca et al. (1995) Rheum. Dis. Clin. North Am. 21:759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; antivirals; and immune modulating agents. Any of the above-mentioned agents can be administered in combination with the TNFα antibody of the invention to treat an TNFα-related disorder using the multiple variable dose or single dose method of treatments of the invention.

In one embodiment, the TNFα antibody of the invention is administered in combination with one of the following agents for the treatment of rheumatoid arthritis using the multiple variable dose method of treatment of the invention: small molecule inhibitor of KDR (ABT-123), small molecule inhibitor of Tie-2; methotrexate; prednisone; celecoxib; folic acid; hydroxychloroquine sulfate; rofecoxib; etanercept; infliximab; anakinra (Kineret #/Amgen); leflunomide; naproxen; valdecoxib; sulfasalazine; ibuprofen; methylprednisolone; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; sulfadiazine; amitriptyline hcl; oxycodone hcl/acetaminophen; olopatadine hcl; misoprostol; naproxen sodium; omeprazole; mycophenolate mofetil; cyclophosphamide; rituximab; IL-1 TRAP; MRA; CTLA4-IG; IL-18 BP; ABT-874; ABT-325 (anti-IL 18); anti-IL 15; BIRB-796; SCIO-469; VX-702; AMG-548; VX-740; Roflumilast; IC-485; CDC-801; and mesopram. In another embodiment, the TNFα antibody of the invention is administered using a multiple-variable dose method for the treatment of a TNFα related disorder in combination with one of the above mentioned agents for the treatment of rheumatoid arthritis. In another embodiment, the above-mentioned additional agents are used in combination with a TNFα antibody in the single dose method of treatment of the invention.

In one embodiment, the TNFα antibody of the invention is administered using the multiple variable dose regimen in combination with one of the following agents for the treatment of a TNFα-related disorder in which TNFα activity is detrimental: anti-IL12 antibody (ABT 874); anti-ILI 8 antibody (ABT 325); small molecule inhibitor of LCK; small molecule inhibitor of COT; anti-IL antibody; small molecule inhibitor of MK2; anti-CD19 antibody; small molecule inhibitor of CXCR3; small molecule inhibitor of CCR5; small molecule inhibitor of CCRII anti-E/L selectin antibody; small molecule inhibitor of P2X7; small molecule inhibitor of IRAK-4; small molecule agonist of glucocorticoid receptor; anti-C5a receptor antibody; small molecule inhibitor of C5a receptor; anti-CD32 antibody; and CD32 as a therapeutic protein.

In yet another embodiment, the TNFα antibody of the invention is administered using the multiple variable dose regimen in combination with an antibiotic or antiinfective agent. Antiinfective agents include those agents known in the art to treat viral, fungal, parasitic or bacterial infections. The term, "antibiotic" as used herein, refers to a chemical substance that inhibits the growth of, or kills, microorganisms.

Encompassed by this term are antibiotic produced by a microorganism, as well as synthetic antibiotics (e. g., analogs) known in the art. Antibiotics include, but are not limited to, clarithromycin (Biaxin), ciprofloxacin (Cipro®), and metronidazole (Flagyl®).

In another embodiment, the TNFα antibody of the invention is administered using the multiple variable dose regimen in combination with an additional therapeutic agent to treat sciatica or pain. Examples of agents which can be used to reduce or inhibit the symptoms of sciatica or pain include hydrocodone bitartrate/apap, rofecoxib, cyclobenzaprine hcl, methylprednisolone, naproxen, ibuprofen, oxycodone hcl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone hcl, tizanidine hcl, diclofenac sodium/misoprostol, propoxyphene napsylate/apap, asa/oxycod/oxycodone ter, ibuprofen/hydrocodone bit, tramadol hcl, etodolac, propoxyphene hcl, amitriptyline hcl, carisoprodol/codeine phos/asa, morphine sulfate, multivitamins, naproxen sodium, orphenadrine citrate, and temazepam.

In yet another embodiment, the TNFα-related disorder is treated using the multiple variable dose regimen with the TNFα antibody of the invention in combination with hemodialysis.

In another embodiment, a TNFα antibody of the invention is used in combination with a drug used to treat Crohn's disease or a Crohn's-related disorder in the multiple variable dose regimen of the invention. Examples of therapeutic agents which can be used to treat Crohn's include mesalamine, prednisone, azathioprine, mercaptopurine, infliximab, budesonide, sulfasalazine, methylprednisolone sod succ, diphenoxylate/atrop sulf, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, hyoscyamine sulfate, cholestyramine/sucrose, ciprofloxacin hydrochloride, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, natalizumab, methylprednisolone, interferon-gamma, and sargramostim (GM-CSF). In one embodiment, methotrexate is administered for the treatment of Crohn's disease at a dose of 2.5 mg to 30 mg per week.

In another embodiment, a TNFα antibody is administered in combination with an additional therapeutic agent to treat asthma in the multiple variable dose regimen of the invention. Examples of agents which can be used to reduce or inhibit the symptoms of asthma include the following: albuterol; salmeterol/fluticasone; sodium; fluticasone propionate; budesonide; prednisone; salmeterol xinafoate; levalbuterol hcl; sulfate/ipratropium; prednisolone sodium phosphate; triamcinolone acetonide; beclomethasone dipropionate; ipratropium bromide; Azithromycin; pirbuterol acetate; prednisolone; theophylline anhydrous; zafirlukast; methylprednisolone sod succ; clarithromycin; formoterol fumarate; influenza virus vaccine; methylprednisolone; trihydrate; allergy injection; cromolyn sodium; cefprozil; fexofenadine hydrochloride; flunisolide/menthol; levofloxacin; amoxicillin/clavulanate, inhaler assist device, guaifenesin, dexamethasone sod phosphate; moxifloxacin hcl; hyclate; guaifenesin/d-methorphan; gatifloxacin; pephedrine/cod/chlorphenir; cetirizine hydrochloride; mometasone furoate; salmeterol xinafoate; benzonatate; cephalexin; pe/hydrocodone/chlorphenir; cetirizine hcl/pseudoephed; phenylephrine/cod/promethazine; codeine/promethazine; flunisolide; dexamethasone; guaifenesin/pseudoephedrine; chlorpheniramine/hydrocodone; nedocromil sodium; terbutaline sulfate; epinephrine and methylprednisolone, metaproterenol sulfate.

In another embodiment, the TNFα antibody of the invention is administered in combination with an additional therapeutic agent to treat COPD in the multiple variable dose regimen of the invention. Examples of agents which can be used to reduce or inhibit the symptoms of COPD include, albuterol sulfate/ipratropium; ipratropium bromide; salmeterol/fluticasone; albuterol; salmeterol; xinafoate; fluticasone propionate; prednisone; theophylline anhydrous; levofloxacin; methylprednisolone sod succ; montelukast sodium; budesonide; formoterol fumarate; triamcinolone acetonide; guaifenesin; azithromycin; beclomethasone; dipropionate; levalbuterol hcl; flunisolide; sodium; trihydrate; gatifloxacin; zafirlukast; furoate; amoxicillin/clavulanate; flunisolide/menthol; chlorpheniramine/hydrocodone; metaproterenol sulfate; methylprednisolone; ephedrine/cod/chlorphenir; pirbuterol acetate; -ephedrine/loratadine; terbutaline-sulfate; tiotropium bromide; (R,R)-formoterol; TgAAT; Cilomilast and Roflumilast.

In another embodiment, the TNFα antibody of the invention is administered in combination with an additional therapeutic agent to treat IPF in the multiple variable dose regimen of the invention. Examples of agents which can be used to reduce or inhibit the symptoms of IPF include prednisone; azathioprine; albuterol; colchicines; sulfate; digoxin; gamma interferon; methylprednisolone sod succ; furosemide; lisinopril; nitroglycerin; spironolactone; cyclophosphamide; ipratropium bromide; actinomycin d; alteplase; fluticasone propionate; levofloxacin; metaproterenol sulfate; morphine sulfate; oxycodone hcl; potassium chloride; triamcinolone acetonide; tacrolimus anhydrous; calcium; interferon-alpha; methotrexate; mycophenolate mofetil.

In one embodiment of the invention, a TNFα antibody is administered in combination with an agent which is commonly used to treat spondyloarthropathies in the multiple variable dose regimen of the invention. Examples of such agents include nonsteroidal, anti-inflammatory drugs (NSAIDs), COX 2 inhibitors, including Celebrex®, Vioxx®, and Bextra®, aand etoricoxib. Physiotherapy is also commonly used to treat spondyloarthropathies, usually in conjunction with non-steoidal inflammatory drugs.

In another embodiment, the TNFα antibody of the invention is administered in combination with an additional therapeutic agent to treat ankylosing spondylitis in the multiple variable dose regimen of the invention. Examples of agents which can be used to reduce or inhibit the symptoms of ankylosing spondylitis include ibuprofen, diclofenac and misoprostol, naproxen, meloxicam, indomethacin, diclofenac, celecoxib, rofecoxib, sulfasalazine, prednisone, methotrexate, azathioprine, minocyclin, prednisone, etanercept, and infliximab.

In another embodiment, the TNFα antibody of the invention is administered in combination with an additional therapeutic agent to treat psoriatic arthritis in the multiple variable dose regimen of the invention. Examples of agents which can be used to reduce or inhibit the symptoms of psoriatic arthritis include methotrexate; etanercept; rofecoxib; celecoxib; folic acid; sulfasalazine; naproxen; leflunomide; methylprednisolone acetate; indomethacin; hydroxychloroquine sulfate; sulindac; prednisone; betamethasone diprop augmented; infliximab; methotrexate; folate; triamcinolone acetonide; diclofenac; dimethylsulfoxide; piroxicam; diclofenac sodium; ketoprofen; meloxicam; prednisone; methylprednisolone; nabumetone; tolmetin sodium; calcipotriene; cyclosporine; diclofenac; sodium/misoprostol; fluocinonide; glucosamine sulfate; gold sodium thiomalate; hydrocodone; bitartrate/apap; ibuprofen; risedronate sodium; sulfadiazine; thioguanine; valdecoxib; alefacept; and efalizumab.

In one embodiment the TNFα inhibitor is administered following an initial procedure for treating coronary heart disease in the multiple variable dose regimen of the invention. Examples of such procedures include, but are not limited to coronary artery bypass grafting (CABG) and Percutaneous transluminal coronary balloon angioplasty (PTCA) or angioplasty. In one embodiment, the TNFα inhibitor is administered in order to prevent stenosis from re-occurring. In another embodiment of the invention, the TNFα inhibitor is administered in order to prevent or treat restenosis. The invention also provides a method of treatment, wherein the TNFα inhibitor is administered prior to, in conjunction with, or following the insertion of a stent in the artery of a subject receiving a procedure for treating coronary heart disease. In one embodiment the stent is administered following CABG or PTCA.

A wide variety of stent grafts may be utilized within the context of the present invention, depending on the site and nature of treatment desired. Stent grafts may be, for example, bifurcated or tube grafts, cylindrical or tapered, self-expandable or balloon-expandable, unibody, or, modular. Moreover, the stent graft may be adapted to release the drug at only the distal ends, or along the entire body of the stent graft. The TNFα inhibitor of the invention can also be administered on a stent. In one embodiment, the TNFα antibody of the invention, including, for example, D2E7/HUMIRA® is administered by a drug-eluting stent.

The TNFα antibody can be administered in combination with an additional therapeutic agent to treat restenosis in the multiple variable dose regimen of the invention. Examples of agents which can be used to treat or prevent restenosis include sirolimus, paclitaxel, everolimus, tacrolimus, ABT-578, and acetaminophen.

The TNFα antibody of the invention can be administered in combination with an additional therapeutic agent to treat myocardial infarction in the multiple variable dose regimen of the invention. Examples of agents which can be used to treat or prevent myocardial infarction include aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hcl/mag carb, bumetanide, alteplase, enalaprilat, amiodarone hydrochloride, tirofiban hcl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine hcl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, abciximab, and cariporide.

The TNFα antibody of the invention can be administered in combination with an additional therapeutic agent to treat angina in the multiple variable dose regimen of the invention. Examples of agents which can be used to treat or prevent angina include: aspirin; nitroglycerin; isosorbide mononitrate; atenolol; metoprolol succinate; metoprolol tartrate; amlodipine besylate; digoxin; dilitiazem hydropchloride; isosorbide dinitrate; clopidogrel bisulfate; nifedipine; atorvastatin calcium; potassium chloride; simvastatin; verapamil hcl; furosemide; propranolol hcl; carvedilo; lisinopril; sprionolactone; hydrochlorothiazide; enalapril maleate; madolol; ramipril; enoxaparin sodium; heparin sodium; valsartan; sotalol hydrochloride; fenofibrate; ezetimibe;

bumetanide; losartan potassium; lisinopril/hydrochlorothiazide; felodipine; captopril; and bisoprolol fumarate.

In one embodiment of the invention, a TNFα antibody is administered in combination with an agent which is commonly used to treat hepatitis C virus in the multiple variable dose regimen of the invention. Examples of such agents include Interferon-aplha-2a, Interferon-alpha-2b, Interferon-alpha con1, Interfero-aopha-n1, Pegylated interferon-alpha-2a, Pegylated interferon-alpha-2b, Ribavirin, Peginterferon alfa-2b and ribavirin, Ursodeoxycholic Acid, Glycyrrhizic Acid, Thymalfasin, Maxamine, and VX-497.

The TNFα antibody of the invention is administered in combination with topical corticosteroids, vitamin D analogs, and topical or oral retinoids, or combinations thereof, for the treatment of psoriasis in the multiple variable dose regimen of the invention. In addition, the TNFα antibody of the invention is administered in combination with one of the following agents for the treatment of psoriasis: small molecule inhibitor of KDR (ABT-123), small molecule inhibitor of Tie-2, calcipotriene, clobetasol propionate, triamcinolone acetonide, halobetasol propionate, tazarotene, methotrexate, fluocinonide, betamethasone diprop augmented, fluocinolone, acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, coal tar, diflorasone diacetate, etanercept, folate, lactic acid, methoxsalen, hc/bismuth subgal/znox/resor, methylprednisolone acetate, prednisone, sunscreen, salicylic acid, halcinonide, anthralin, clocortolone pivalate, coal extract, coal tar/salicylic acid, coal tar/salicylic acid/sulfur, desoximetasone, diazepam, emollient, pimecrolimus emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, alefacept, efalizumab, tacrolimus, pimecrolimus, PUVA, UVB and other phototherapy, and sulfasalazine.

An antibody, antibody portion, or other TNFα inhibitor of the invention can be used in combination with other agents to treat skin conditions in the multiple variable dose regimen of the invention. For example, an antibody, antibody portion, or other TNFα inhibitor of the invention is combined with PUVA therapy. PUVA is a combination of psoralen (P) and long-wave ultraviolet radiation (UVA) that is used to treat many different skin conditions. The antibodies, antibody portions, or other TNFα inhibitors of the invention can also be combined with pimecrolimus. In another embodiment, the antibodies of the invention are used to treat psoriasis, wherein the antibodies are administered in combination with tacrolimus. In a further embodiment, tacrolimus and TNFα inhibitors are administered in combination with methotrexate and/or cyclosporine. In still another embodiment, the TNFα inhibitor of the invention is administered with excimer laser treatment for treating psoriasis.

Nonlimiting examples of other therapeutic agents with which a TNFα inhibitor can be combined to treat a skin or nail disorder include UVA and UVB phototherapy in the multiple variable dose regimen of the invention. Other nonlimiting examples which can be used in combination with a TNFα inhibitor include anti-IL-12 and anti-IL-18 therapeutic agents, including antibodies.

In one embodiment, the TNFα antibody of the invention is administered in combination with an additional therapeutic agent in the treatment of Behcet's disease in the multiple variable dose regimen of the invention. Additional therapeutic agents which can be used to treat Behcet's disease include, but are not limited to, prednisone, cyclophosphamide (Cytoxan), Azathioprine (also called imuran, methotrexate, timethoprim/sulfamethoxazole (also called bactrim or septra) and folic acid.

Any one of the above-mentioned therapeutic agents, alone or in combination therewith, can be administered to a subject suffering from a TNFα-related disorder in which TNFα is detrimental, in combination with the TNFα antibody using a multiple variable dose treatment regimen of the invention. In one embodiment, any one of the above-mentioned therapeutic agents, alone or in combination therewith, can be administered to a subject suffering from rheumatoid arthritis in addition to a TNFα antibody to treat a TNFα-related disorder. It should be understood that the additional therapeutic agents can be used in combination therapy as described above, but also may be used in other indications described herein wherein a beneficial effect is desired.

It also is understood that the above-mentioned additional agents can also be used in combination with a TNFα inhibitor, e. g., a TNFα antibody, to treat a TNFα-related disorder using the single dose treatment method of the invention.

This invention is further illustrated by the following examples which should not be construed as limiting. The contents of all references, patents and published patent applications cited throughout this application are incorporated herein by reference

EXAMPLES

Example 1

As described in the HUMIRA® FDA label, September 2014:

"The safety and efficacy of multiple doses of HUMIRA were assessed in adult patients with moderately to severely active Crohn's disease, CD, (Crohn's Disease Activity Index (CDAI)≥220 and ≤450) in randomized, double-blind, placebo-controlled studies. Concomitant stable doses of aminosalicylates, corticosteroids, and/or immunomodulatory agents were permitted, and 79% of patients continued to receive at least one of these medications.

Induction of clinical remission (defined as CDAI<150) was evaluated in two studies. In Study CD-I, 299 TNF-blocker naïve patients were randomized to one of four treatment groups: the placebo group received placebo at Weeks 0 and 2, the 160/80 group received 160 mg HUMIRA at Week 0 and 80 mg at Week 2, the 80/40 group received 80 mg at Week 0 and 40 mg at Week 2, and the 40/20 group received 40 mg at Week 0 and 20 mg at Week 2. Clinical results were assessed at Week 4.

In the second induction study, Study CD-II, 325 patients who had lost response to, or were intolerant to, previous infliximab therapy were randomized to receive either 160 mg HUMIRA at Week 0 and 80 mg at Week 2, or placebo at Weeks 0 and 2. Clinical results were assessed at Week 4.

Maintenance of clinical remission was evaluated in Study CD-III. In this study, 854 patients with active disease received open-label HUMIRA, 80 mg at week 0 and 40 mg at Week 2. Patients were then randomized at Week 4 to 40 mg HUMIRA every other week, 40 mg HUMIRA every week, or placebo. The total study duration was 56 weeks. Patients in clinical response (decrease in CDAI≥70) at Week 4 were stratified and analyzed separately from those not in clinical response at Week 4.

Induction of Clinical Remission

A greater percentage of the patients treated with 160/80 mg HUMIRA achieved induction of clinical remission versus placebo at Week 4 regardless of whether the patients were TNF blocker naïve (CD-I), or had lost response to or were intolerant to infliximab (CD-II)".

"Maintenance of Clinical Remission

In Study CD-III at Week 4, 58% (499/854) of patients were in clinical response and were assessed in the primary analysis. At Weeks 26 and 56, greater proportions of patients who were in clinical response at Week 4 achieved clinical remission in the HUMIRA 40 mg every other week maintenance group compared to patients in the placebo maintenance group. The group that received HUMIRA therapy every week did not demonstrate significantly higher remission rates compared to the group that received HUMIRA every other week.

Of those in response at Week 4 who attained remission during the study, patients in the HUMIRA every other week group maintained remission for a longer time than patients in the placebo maintenance group. Among patients who were not in response by Week 12, therapy continued beyond 12 weeks did not result in significantly more responses."

Example 2

As described in the HUMIRA® FDA label, September 2014:

"A randomized, double-blind, 52-week clinical study of 2 dose levels of HUMIRA (Study PCD-I) was conducted in 192 pediatric patients (6 to 17 years of age) with moderately to severely active Crohn's disease (defined as Pediatric Crohn's Disease Activity Index (PCDAI) score >30).[2] Enrolled patients had over the previous two year period an inadequate response to corticosteroids or an immunomodulator (i.e., azathioprine, 6-mercaptopurine, or methotrexate). Patients who had previously received a TNF blocker were allowed to enroll if they had previously had loss of response or intolerance to that TNF blocker".

Patients received open-label induction therapy at a dose based on their body weight (≥40 kg and <40 kg). Patients weighing ≥40 kg received 160 mg (at Week 0) and 80 mg (at Week 2). Patients weighing <40 kg received 80 mg (at Week 0) and 40 mg (at Week 2). At Week 4, patients within each body weight category (≥40 kg and <40 kg) were randomized 1:1 to one of two maintenance dose regimens (high dose and low dose). The high dose was 40 mg every other week for patients weighing ≥40 kg and 20 mg every other week for patients weighing <40 kg. The low dose was 20 mg every other week for patients weighing ≥40 kg and 10 mg every other week for patients weighing <40 kg.

Concomitant stable dosages of corticosteroids (prednisone dosage ≤40 mg/day or equivalent) and immunomodulators (azathioprine, 6-mercaptopurine, or methotrexate) were permitted throughout the study. At Week 12, patients who experienced a disease flare (increase in PCDAI of ≥15 from Week 4 and absolute PCDAI >30) or who were non-responders (did not achieve a decrease in the PCDAI of ≥15 from baseline for 2 consecutive visits at least 2 weeks apart) were allowed to dose-escalate (i.e., switch from blinded every other week dosing to blinded every week dosing); patients who dose-escalated were considered treatment failures.

At baseline, 38% of patients were receiving corticosteroids, and 62% of patients were receiving an immunomodulator. Forty-four percent (44%) of patients had previously lost response or were intolerant to a TNF blocker. The median baseline PCDAI score was 40.

Of the 192 patients total, 188 patients completed the 4 week induction period, 152 patients completed 26 weeks of treatment, and 124 patients completed 52 weeks of treatment. Fifty-one percent (51%) (48/95) of patients in the low maintenance dose group dose-escalated, and 38% (35/93) of patients in the high maintenance dose group dose-escalated.

At Week 4, 28% (52/188) of patients were in clinical remission (defined as PCDAI ≤10). The proportions of patients in clinical remission (defined as PCDAI ≤10) and clinical response (defined as reduction in PCDAI of at least 15 points from baseline) were assessed at Weeks 26 and 52. At both Weeks 26 and 52, the proportion of patients in clinical remission and clinical response was numerically higher in the high dose group compared to the low dose group (Table 13). The recommended maintenance regimen is 20 mg every other week for patients weighing <40 kg and 40 mg every other week for patients weighing ≥40 kg. Every week dosing is not the recommended maintenance dosing regimen."

Example 3

The safety and efficacy of HUMIRA were assessed in adult patients with moderately to severely active ulcerative colitis (Mayo score 6 to 12 on a 12 point scale, with an endoscopy subscore of 2 to 3 on a scale of 0 to 3) despite concurrent or prior treatment with immunosuppressants such as corticosteroids, azathioprine, or 6-MP in two randomized, double-blind, placebo-controlled clinical studies (Studies UC-I and UC-II). Both studies enrolled TNF-blocker naïve patients, but Study UC-II also allowed entry of patients who lost response to or were intolerant to TNF-blockers. Forty percent (40%) of patients enrolled in Study UC-II had previously used another TNF-blocker.

Concomitant stable doses of aminosalicylates and immunosuppressants were permitted. In Studies UC-I and II, patients were receiving aminosalicylates (69%), corticosteroids (59%) and/or azathioprine or 6-MP (37%) at baseline. In both studies, 92% of patients received at least one of these medications.

Induction of clinical remission (defined as Mayo score ≤2 with no individual subscores >1) at Week 8 was evaluated in both studies. Clinical remission at Week 52 and sustained clinical remission (defined as clinical remission at both Weeks 8 and 52) were evaluated in Study UC-II.

In Study UC-I, 390 TNF-blocker naïve patients were randomized to one of three treatment groups for the primary efficacy analysis. The placebo group received placebo at Weeks 0, 2, 4 and 6. The 160/80 group received 160 mg HUMIRA at Week 0 and 80 mg at Week 2, and the 80/40 group received 80 mg HUMIRA at Week 0 and 40 mg at Week 2. After Week 2, patients in both HUMIRA treatment groups received 40 mg every other week (eow).

In Study UC-II, 518 patients were randomized to receive either HUMIRA 160 mg at Week 0, 80 mg at Week 2, and 40 mg eow starting at Week 4 through Week 50, or placebo starting at Week 0 and eow through Week 50. Corticosteroid taper was permitted starting at Week 8. "In both Studies UC-I and UC-II, a greater percentage of the patients treated with 160/80 mg of HUMIRA compared to patients treated with placebo achieved induction of clinical remission. In Study UC-II, a greater percentage of the patients treated with 160/80 mg of HUMIRA compared to patients treated with placebo achieved sustained clinic remission".

In Study UC-I, there was no statistically significant difference in clinical remission observed between the HUMIRA 80/40 mg group and the placebo group at Week 8.

In Study UC-II, 17.3% (43/248) in the HUMIRA group were in clinical remission at Week 52 compared to 8.5% (21/246) in the placebo group (treatment difference: 8.8%; 95% confidence interval (CI): [2.8%, 14.5%]; p<0.05).

In the subgroup of patients in Study UC-II with prior TNF-blocker use, the treatment difference for induction of clinical remission appeared to be lower than that seen in the whole study population, and the treatment differences for sustained clinical remission and clinical remission at Week 52 appeared to be similar to those seen in the whole study population. The subgroup of patients with prior TNF-blocker use achieved induction of clinical remission at 9% (9/98) in the HUMIRA group versus 7% (7/101) in the placebo group, and sustained clinical remission at 5% (5/98) in the HUMIRA group versus 1% (1/101) in the placebo group. In the subgroup of patients with prior TNF-blocker use, 10% (10/98) were in clinical remission at Week 52 in the HUMIRA group versus 3% (3/101) in the placebo group."

Example 4

This following evaluates the efficacy and safety of two adalimumab induction regimens in subjects with moderately to severely active Crohn's disease and evidence of mucosal ulceration.

The trial evaluates the Efficacy and Safety of Two Adalimumab Induction Regimens in Subjects With Moderately to Severely Active Crohn's Disease and Evidence of Mucosal Ulceration.

Arm 1: Subjects are randomized to receive a higher induction regimen of adalimumab. After the induction regimen is provided, subjects in this arm will receive blinded adalimumab until Week 12. No placebo arm is planned Arm 2: Subjects are randomized to receive a standard induction regimen of adalimumab. After the induction regimen is provided, subjects in this arm will receive blinded adalimumab until Week 12. No placebo arm is planned.

Inclusion Criteria:
1. Diagnosis of Crohn's disease (CD) for at least 90 days, confirmed by endoscopy during the Screening Period.
2. Active CD with a Crohn's Disease Activity Index (CDAI) despite treatment with oral corticosteroids and/or immunosuppressants.
3. Mucosal ulceration on endoscopy.

Exclusion Criteria:
1. Subject with ulcerative colitis or indeterminate colitis.
2. Subject who has had surgical bowel resections in the past 6 months or is planning resection.
3. Subjects with an ostomy or ileoanal pouch.
4. Subject with symptomatic bowel stricture or abdominal or peri-anal abcess.
5. Subject who has short bowel syndrome.
6. Chronic recurring infections or active Tuberculosis (TB).

Primary Outcome Measures:
Proportion of subject who achieve clinical remission [Time Frame: At Week 4]
[Designated as safety issue: No]
Clinical remission will be scored using Crohn's Disease Activity Index (CDAI).
Proportion of subjects who achieve endoscopic improvement [Time Frame: At Week 12][Designated as safety issue: No]
Endoscopic improvement will be scored using Simplified Endoscopic Score for Crohn's Disease (SES CD).

Secondary Outcome Measures:
Proportion of subjects who achieve clinical remission [Time Frame: At Week 12][Designated as safety issue: No]
Clinical remission will be scored using Crohn's Disease Activity Index (CDAI).
Proportion of subjects who achieve clinical remission and endoscopic improvement
[Time Frame: Clinical remission at Week 4 and endoscopic improvement at Week 12][Designated as safety issue: No]
Clinical remission will be scored using Crohn's Disease Activity Index (CDAI) and endoscopic improvement will be scored using Simplified Endoscopic Score for Crohn's Disease (SES-CD).
Proportion of subjects who discontinued corticosteroid use and achieved clinical remission
[Time Frame: At Week 12] [Designated as safety issue: No]
Clinical remission will be scored using Crohn's Disease Activity Index (CDAI).
Proportion of subjects with endoscopic response [Time Frame: At Week 12]
[Designated as safety issue: No]
Endoscopic improvement will be scored using Simplified Endoscopic Score for Crohn's Disease (SES CD).
Change in fecal calprotectin level [Time Frame: From Week 0 to Week 12]
[Designated as safety issue: No Example 5

This following evaluates the safety and efficacy of two dosing regimens in achieving clinical remission at Week 8 in subjects with moderately to severely active Ulcerative Colitis The trail evaluates higher versus standard adalimumab dosing regimens for induction and maintenance therapy in subjects with moderately to severely active ulcerative colitis.

Arm 1: Active Comparator: Standard Induction Dose
Standard Induction Dose Adalimumab (e.g. 160 mg)
Arm 2: Experimental: Higher Induction Dose
Higher Induction Dose Adalimumab (e.g. 170, 180, 190, 200, 210, 220, 230, 240, 250, 260, 270, 280, 290, 300, 310 or 320 mg)
Arm 3: Active Comparator: Standard Maintenance Dose
Standard Maintenance Dose Adalimumab (e.g. 80 mg)
Arm 4: Experimental: Higher Maintenance Dose
Higher Maintenance Dose Adalimumab (e.g. 80, 90, 100, 110, 120, 130, 140, 150 or 160 mg)
Arm 5: Experimental: Experimental Maintenance Dose
Experimental Maintenance Dose (e.g. 20, 50, 60, 70, 80, 90, 100, 110, 120 or 160 mg)

Inclusion Criteria:
1. Diagnosis of Ulcerative Colitis (UC) for at least 90 days, confirmed by endoscopy during Screening period.
2. Active UC with Mayo Score of 6 to 12 points and endoscopy subscore of 2 to 3 despite concurrent or prior treatment with a full and adequate course, in the opinion of the Investigator, with oral corticosteroids or immunosuppressants or both.

Exclusion Criteria:
1. Subject with Crohn's disease (CD) or indeterminate colitis (IC).
2. Current diagnosis of fulminant colitis and/or toxic megacolon.
3. Subjects with disease limited to the rectum (ulcerative proctitis) during the screening endoscopy.
4. Chronic recurring infections or active Tuberculosis (TB).

Primary Outcome Measures:
Proportion of subjects achieving clinical remission (per full Mayo Score) [Time Frame: Week 8] [Designated as safety issue: No]

Secondary Outcome Measures:
Proportion of subjects achieving endoscopic improvement (endoscopic subscore of 0 or 1) [Time Frame: Week 8] [Designated as safety issue: No]
Proportion of Week 8 responders (per full Mayo Score) achieving clinical remission (per full Mayo Score) [Time Frame: Week 52] [Designated as safety issue: No]
Proportion of Week 8 responders (per full Mayo Score) achieving endoscopic improvement (endoscopic subscore of 0 or 1) [Time Frame: Week 52] [Designated as safety issue: No]

Example 6

This following evaluates the efficacy, safety, and pharmacokinetics in Chinese subjects with Crohn's disease.

The trail evaluates Evaluate the Pharmacokinetics, Safety, and Efficacy of Two Adalimumab Dosing Regimens in Chinese Subjects With Moderately to Severely Active Crohn's Disease and Elevated High-Sensitivity C-reactive Protein.

Arm A: Experimental: Standard induction dose.

Subjects will be given the standard loading dose (160 mg) of adalimumab at Weeks 0 and 2 followed by the standard maintenance dose (80 mg) beginning at week 4. (Subjects will be given subcutaneous injections of adalimumab.)

Arm B: Low induction dose

Subjects will be given a low loading dose (150 mg, 140 mg, 130 mg, 120 mg, 110 mg, 100 mg, 90 mg, 80 mg, 70 mg, 60 mg, 50 mg) of adalimumab at Weeks 0 and 2 followed by the standard maintenance (80 mg) dose beginning at week 4. (Subjects will be given subcutaneous injections of adalimumab).

Inclusion Criteria:
1. Subjects of Chinese decent with full Chinese parentage.
2. Diagnosis of Crohn's disease (CD) for at least 3 months prior to Week 0 confirmed by endoscopy, radiologic evaluation, and/or histology during the Screening Period.
3. Crohn's Disease Activity Index (CDAI) ≥220 and ≤450 despite treatment with oral corticosteroids and/or immunosuppressants.
4. Subject has a negative Tuberculosis (TB) Screening Assessment.

Exclusion Criteria:
1. Subject with ulcerative colitis or indeterminate colitis.
2. Subject who has had a surgical bowel resection within the past 6 months or who is planning any resection at any time point in the future.
3. Subject with an ostomy or ileoanal pouch.
4. Subject who has short bowel syndrome.
5. Subject with symptomatic known obstructive strictures.
6. Subject with an internal or external fistula (with the exception of an anal fistula without abscess).
7. Chronic recurring infections or active TB.

Primary Outcome Measures:
To characterize the pharmacokinetics of two dosing regimens of adalimumab
[Time Frame: At Week 8] [Designated as safety issue: No]. Adalimumab serum concentrations will be measured.

Secondary Outcome Measures:
Change in Laboratory Test Variables [Time Frame: From Week 0 to Week 26]
[Designated as safety issue: Yes] Hematology, Chemistry, and Urinalysis.
Change in Vital Sign Variables [Time Frame: From Week 0 to Week 26]
[Designated as safety issue: Yes] Blood Pressure, heart rate, respiratory rate, and body temperature.
Number of subjects with adverse events [Time Frame: Up to 70 days after Week 26]
[Designated as safety issue: Yes]

Other Outcome Measures:
Presence of anti-adalimumab antibody (AAA) [Time Frame: Up to Week 8]
[Designated as safety issue: No] AAA concentrations will be measured.

SEQUENCES

SEQ ID NO:1 Adalimumab (D2E7) light chain variable region amino acid sequence
DIQMTQSPSSLSASVGDRVTITCRASQGIR-NYLAWYQQKPGKAPKLLIYAASTLQSGVPS
RFSGSGSGTDFTLTISSLQPEDVATYYCQRYNRAPYT-FGQGTKVEIK SEQ ID NO:2 Adalimumab (D2E7) heavy chain variable region amino acid sequence
EVQLVESGGGLVQPGRSLRLSCAASGFTFDDYAM-HWVRQAPGKGLEWVSAITWNSGHID YADSVEGR-
FTISRDNAKNSLYLQMNSLRAEDTAVYYCAKVSYL-STASSLDYWGQGTLVTVS S SEQ ID NO:3 Adalimumab (D2E7) light chain variable region CDR3 amino acid sequence
QRYNRAPYX (X can be any naturally occuring amino acid)

SEQ ID NO:4 Adalimumab (D2E7) heavy chain variable region CDR3 amino acid sequence
VSYLSTASSLDX (X can be any naturally occuring amino acid)

SEQ ID NO:5 Adalimumab (D2E7) light chain variable region CDR2 amino acid sequence
AASTLQS SEQ ID NO:6 Adalimumab (D2E7) heavy chain variable region CDR2 amino acid sequence
AITWNSGHIDYADSVEG SEQ ID NO:7 Adalimumab (D2E7) light chain variable region CDR1 amino acid sequence
RASQGIRNYLA SEQ ID NO:8 Adalimumab (D2E7) heavy chain variable region CDR1 amino acid sequence
DYAMH SEQ ID NO:9 Adalimumab (D2E7) light chain variable region DNA sequence
GACATCCAGATGACCCAGTCTCCATCCTCCCT-GTCTGCATCTGTAGGGGACAGAGTCA CCATCACTT-
GTCGGGCAAGTCAGGGCATCAGAAATTACTTAGC-CTGGTATCAGCAAAAA CCAGGGAAAGCCCCTAAGCTCCTGATCTATGCTG-CATCCACTTTGCAATCAGGGGTCC CATCTCGGT-TCAGTGGCAGTGGATCTGGGACAGATTTCACTCT-CACCATCAGCAGCCTA CAGCCTGAAGATGTTGCAACTTATTACTGT-CAAAGGTATAACCGTGCACCGTATACTTTT GGCCA-GGGGACCAAGGTGGAAATCAAA SEQ ID NO:10 Adalimumab (D2E7) heavy chain variable region DNA sequence GAGGTGCAGCTGGTGGAGTCTGGGGGAGGCT-TGGTACAGCCCGGCAGGTCCCTGAGACTCTCCTGT-GCGGCCTCTGGATTCACCTTTGATGATTATGCCATG-CACTGGGTCCGGCA AGCTCCAGGGAAGGGCCTGGAATGGGTCTCAGC-TATCACTTGGAATAGTGGTCACATA GACTATGCG-GACTCTGTGGAGGGCCGATTCACCATCTCCAGA-GACAACGCCAAGAACT CCCTGTATCTGCAAATGAACAGTCTGAGAGCTGAG-GATACGGCCGTATATTACTGTGCG AAAGTCTCG-TACCTTAGCACCGCGTCCTCCCTTGACTAT-TGGGGCCAAGGTACCCTGG TCACCGTCTCGAGT

---

The invention claimed is:

1. A method of treating a disorder in which TNFα activity is detrimental, the method comprising administering a multiple-variable dose of adalimumab to a subject in need thereof, wherein the multiple-variable dose comprises administering a first induction dose of adalimumab and administering a second induction dose of adalimumab that is 40-60% of the first induction dose, such that a threshold level of the adalimumab is achieved within an induction phase, and administering at least one treatment dose comprising 80 mg adalimumab within a treatment phase subsequent to the induction phase, such that treatment of the disorder occurs, wherein the adalimumab is administered subcutaneously in a liquid formulation containing 100 mg/mL of adalimumab.

2. The method of claim 1, wherein the disorder in which TNF activity is detrimental is selected from the group consisting of an autoimmune disease, an infectious disease, transplant rejection or graft-versus-host disease, malignancy, a pulmonary disorder, an intestinal disorder, a cardiac disorder, sepsis, a spondyloarthropathy, a metabolic disorder, anemia, pain, a hepatic disorder, a skin disorder, a nail disorder, vasculitis, rheumatoid arthritis, rheumatoid spondylitis, osteoarthritis, gouty arthritis, allergy, multiple sclerosis, autoimmune diabetes, autoimmune uveitis, nephrotic syndrome, inflammatory bone disorders, bone resorption disease, alcoholic hepatitis, viral hepatitis, fulminant hepatitis, coagulation disturbances, burns, reperfusion injury, keloid formation, scar tissue formation, pyrexia, periodontal disease, obesity, radiation toxicity, Behcet's disease, ankylosing spondylitis, asthma, chronic obstructive pulmonary disorder (COPD), idiopathic pulmonary fibrosis (IPF), restenosis, diabetes, a Crohn's disease-related disorder, juvenile rheumatoid arthritis (JRA), a hepatitis C virus infection, psoriatic arthritis, chronic plaque psoriasis, Crohn's disease, ulcerative colitis, psoriasis, psoriasis in combination with psoriatic arthritis (PsA) and rheumatoid arthritis.

3. The method of claim 1, wherein the second induction dose is administered 2 weeks following the first induction dose.

4. The method of claim 1, wherein the second induction dose ranges from 80 to 160 mg.

5. The method of claim 4, wherein the second induction dose comprises 80 mg.

6. The method of claim 1, wherein the first induction dose comprises 200 mg.

7. The method of claim 1, wherein the treatment dose is administered 2 weeks following the induction dose and biweekly thereafter.

8. The method of claim 1, wherein the adalimumab is administered in combination with methotrexate.

9. The method of claim 1, wherein the adalimumab is administered by injection through a needle with an outer diameter between 0.1 and 0.5 mm.

10. The method of claim 9, wherein the adalimumab is administered by injection through a needle with an outer diameter between 0.25 and 0.5 mm.

11. The method of claim 1, wherein the disorder in which TNFα activity is detrimental is Crohn's disease or ulcerative colitis.

12. A method of treating Crohn's disease or ulcerative colitis, the method comprising administering a multiple-variable dose of adalimumab to a subject in need thereof, the multiple variable dose comprising a first induction dose of adalimumab, followed by a second induction dose of adalimumab two weeks later that is 40-60% of the first induction dose, followed by a treatment dose of two weeks after the second induction dose, wherein the adalimumab is administered subcutaneously in a liquid formulation containing 100 mg/mL of adalimumab.

13. The method of claim 12, wherein the treatment dose is administered biweekly.

* * * * *